(12) United States Patent
Barnscheid

(10) Patent No.: US 10,300,141 B2
(45) Date of Patent: May 28, 2019

(54) TAMPER RESISTANT DOSAGE FORM COMPRISING INORGANIC SALT

(71) Applicant: GRÜNENTHAL GMBH, Aachen (DE)

(72) Inventor: Lutz Barnscheid, Mönchengladbach (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 14/979,888

(22) Filed: Dec. 28, 2015

(65) Prior Publication Data

US 2016/0106839 A1    Apr. 21, 2016

Related U.S. Application Data

(63) Continuation of application No. 13/781,957, filed on Mar. 1, 2013, now abandoned, which is a continuation of application No. PCT/EP2011/004406, filed on Sep. 1, 2011.

(30) Foreign Application Priority Data

Sep. 2, 2010 (EP) .................................... 10009121

(51) Int. Cl.
| | |
|---|---|
| A61K 9/20 | (2006.01) |
| A61K 47/02 | (2006.01) |
| A61K 47/10 | (2017.01) |
| A61K 31/135 | (2006.01) |
| A61K 31/485 | (2006.01) |

(52) U.S. Cl.
CPC ............ *A61K 47/02* (2013.01); *A61K 9/2009* (2013.01); *A61K 9/2031* (2013.01); *A61K 31/135* (2013.01); *A61K 31/485* (2013.01); *A61K 47/10* (2013.01)

(58) Field of Classification Search
CPC .... A61K 31/135; A61K 31/485; A61K 47/02; A61K 47/10; A61K 9/2009; A61K 9/2031
See application file for complete search history.

(56) References Cited

U.S. PATENT DOCUMENTS

| | | | |
|---|---|---|---|
| 2,524,855 A | 10/1950 | Schnider et al. | |
| 2,806,033 A | 9/1957 | Lewenstein et al. | |
| 2,987,445 A | 6/1961 | Levesque | |
| 3,332,950 A | 7/1967 | Blumberg et al. | |
| 3,370,035 A | 2/1968 | Ogura et al. | |
| 3,652,589 A | 3/1972 | Flick et al. | |
| 3,658,259 A | 4/1972 | Ledergerber et al. | |
| 3,806,603 A | 4/1974 | Gaunt et al. | |
| 3,865,108 A | 2/1975 | Hartop | |
| 3,941,865 A | 3/1976 | Miller et al. | |
| 3,966,747 A | 6/1976 | Monkovic et al. | |
| 3,980,766 A | 9/1976 | Shaw et al. | |
| 4,002,173 A | 1/1977 | Manning et al. | |
| 4,014,965 A | 3/1977 | Stube et al. | |
| 4,070,494 A | 1/1978 | Hoffmeister et al. | |
| 4,070,497 A | 1/1978 | Wismer et al. | |
| 4,175,119 A | 11/1979 | Porter | |
| 4,200,704 A | 4/1980 | Stanley et al. | |
| 4,207,893 A | 6/1980 | Michaels | |
| 4,262,017 A | 4/1981 | Kuipers et al. | |
| 4,343,789 A | 8/1982 | Kawata et al. | |
| 4,353,887 A | 10/1982 | Hess et al. | |
| 4,404,183 A | 9/1983 | Kawata et al. | |
| 4,427,681 A | 1/1984 | Munshi et al. | |
| 4,427,778 A | 1/1984 | Zabriskie | |
| 4,457,933 A | 7/1984 | Gordon et al. | |
| 4,462,941 A | 7/1984 | Lee et al. | |
| 4,473,640 A | 9/1984 | Combie et al. | |
| 4,483,847 A | 11/1984 | Augart | |
| 4,485,211 A | 11/1984 | Okamoto | |
| 4,529,583 A | 7/1985 | Porter | |
| 4,599,342 A | 7/1986 | La Hann | |
| 4,603,143 A | 7/1986 | Schmidt | |

(Continued)

FOREIGN PATENT DOCUMENTS

| | | |
|---|---|---|
| AR | 046994 A1 | 12/2004 |
| AR | 045353 A1 | 10/2005 |

(Continued)

OTHER PUBLICATIONS

Bauer, Kurt H., et al., Coated Pharmaceutical Dosage Forms—Fundamentals, Manufacturing Techniques, Biopharmaceutical Aspects, Test Methods and Raw Materials, 1st edition, 1998, CRC Press, Medpharm Scientific Publishers, (Preface, Table of Content, List of Abbreviations, Explanation of Terms only).
Baum et al.,"The impact of the addition of naloxone on the use and abuse of pentazocine", Public Health Reports, Jul.-Aug., 1987, vol. 102 No, 4, p. 426-429.
Block, Lawrence. Medicated Applications, Chapter 88. In Remington's Pharmaceutical Sciences, 17th Ed, 1985.
Braun, et al. A study of Bite Force. Part 2: Relationship to Various cephalometric Measurements. Angel Orthodontist, vol. 65 (5) pp. 373-377, 1995.
Brown, The Dissolution Procedure: Development and Validation, heading "Study Design", "Time Points" US Pharmacopoeia (USP), vol. 31(5), General Chapter 1092, pp. 1-15, 2006.

(Continued)

*Primary Examiner* — Michael B. Pallay
(74) *Attorney, Agent, or Firm* — Norris McLaughlin, P.A.

(57) ABSTRACT

A pharmaceutical dosage form exhibiting a breaking strength of at least 500 N, wherein the dosage form contains a pharmacologically active ingredient (A); an inorganic salt (B); and a polyalkylene oxide (C) having a weight average molecular weight of at least 200,000 g/mol, wherein the content of the polyalkylene oxide (C) is at least 20 wt.-%, based on the total weight of the dosage form; wherein the pharmacologically active ingredient (A) is present in a controlled-release matrix comprising the inorganic salt (B) and the polyalkylene oxide (C) and wherein, under in vitro conditions, the release profile of the pharmacologically active ingredient (A) from the matrix comprises at least a time interval during which the release follows zero order kinetics.

22 Claims, 5 Drawing Sheets

(56) References Cited

U.S. PATENT DOCUMENTS

| | | |
|---|---|---|
| 4,612,008 A | 9/1986 | Wong et al. |
| 4,629,621 A | 12/1986 | Snipes |
| 4,667,013 A | 5/1987 | Reichle |
| 4,690,822 A | 9/1987 | Uemura |
| 4,711,894 A | 12/1987 | Wenzel et al. |
| 4,713,243 A | 12/1987 | Schiraldi et al. |
| 4,744,976 A | 5/1988 | Snipes et al. |
| 4,764,378 A | 8/1988 | Keitn et al. |
| 4,765,989 A | 8/1988 | Wong et al. |
| 4,774,074 A | 9/1988 | Snipes |
| 4,774,092 A | 9/1988 | Hamilton |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,954,346 A | 9/1990 | Sparta et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinty |
| 5,073,379 A | 12/1991 | Klimesch et al. |
| 5,082,668 A | 1/1992 | Wong et al. |
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,194 A | 4/1993 | Edgren et al. |
| 5,200,197 A | 4/1993 | Wright et al. |
| 5,211,892 A | 5/1993 | Gueret |
| 5,225,417 A | 7/1993 | Dappen |
| 5,227,157 A | 7/1993 | Mc Ginity et al. |
| 5,229,164 A | 7/1993 | Pins et al. |
| 5,273,758 A | 12/1993 | Royce |
| 5,326,852 A | 7/1994 | Fujikake |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,679,685 A | 10/1997 | Cincotta et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Gradums et al. |
| 5,811,126 A | 9/1998 | Krishanamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,914,132 A | 6/1999 | Kelm et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A * | 7/2000 | Pillay .................. A61K 9/0065 424/468 |
| 6,093,420 A | 7/2000 | Baichwal |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,228,863 B1 | 5/2001 | Palermo et al. |
| 6,235,825 B1 | 5/2001 | Yoshida et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,251,430 B1 | 6/2001 | Zhang et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,322,811 B1 | 11/2001 | Verma et al. |
| 6,322,819 B1 | 11/2001 | Burnside et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,387,995 B1 | 5/2002 | Sojka |
| 6,399,100 B1 | 6/2002 | Clancy et al. |
| 6,419,954 B1 | 7/2002 | Chu et al. |
| 6,436,441 B1 | 8/2002 | Sako et al. |
| 6,455,052 B1 | 9/2002 | Marcussen et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breitenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer et al. |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,332,182 B2 | 2/2008 | Sackler |

(56) References Cited

U.S. PATENT DOCUMENTS

| | | |
|---|---|---|
| 7,388,068 B2 | 6/2008 | Falk et al. |
| 7,399,488 B2 | 7/2008 | Hirsh et al. |
| 7,510,726 B2 | 3/2009 | Kumar et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |
| 7,842,307 B2 | 11/2010 | Oshlack et al. |
| 7,851,482 B2 | 12/2010 | Dung et al. |
| 7,932,258 B2 | 4/2011 | Petereit et al. |
| 7,939,543 B2 | 5/2011 | Kupper |
| 7,968,119 B2 | 6/2011 | Farrell |
| 7,994,364 B2 | 8/2011 | Fischer et al. |
| 8,075,872 B2 | 12/2011 | Arkenau-Maric |
| 8,101,630 B2 | 1/2012 | Kumar et al. |
| 8,114,383 B2 | 2/2012 | Bartholomaeus et al. |
| 8,114,384 B2 | 2/2012 | Arkenau et al. |
| 8,114,838 B2 | 2/2012 | Marchionni |
| 8,192,722 B2 | 6/2012 | Arkenau-Maric et al. |
| 8,202,542 B1 | 6/2012 | Mehta et al. |
| 8,309,060 B2 | 11/2012 | Bartholomeus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Arkenau-Maric et al. |
| 8,858,963 B1 | 10/2014 | Devarakonda et al. |
| 8,901,113 B2 | 12/2014 | Leech et al. |
| 9,044,758 B2 | 6/2015 | Niwa et al. |
| 9,192,578 B2 | 11/2015 | McGinity et al. |
| 9,463,165 B2 | 10/2016 | Shimatani et al. |
| 9,629,807 B2 | 4/2017 | Arkenau-Maric et al. |
| 9,675,610 B2 | 6/2017 | Bartholomaeus et al. |
| 9,737,490 B2 | 8/2017 | Barnscheid et al. |
| 9,855,263 B2 | 1/2018 | Wening et al. |
| 9,884,022 B2 | 2/2018 | Deshmukh et al. |
| 9,925,146 B2 | 3/2018 | Barnscheid et al. |
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0187192 A1 | 2/2002 | Josh et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0132395 A1 | 9/2002 | Iyer et al. |
| 2002/0176888 A1 | 11/2002 | Bartholomaeus et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0044458 A1 | 3/2003 | Wright et al. |
| 2003/0044464 A1 | 3/2003 | Ziegler et al. |
| 2003/0059397 A1 | 3/2003 | Hughes |
| 2003/0064099 A1 | 4/2003 | Oshlack et al. |
| 2003/0068276 A1 | 4/2003 | Hughes et al. |
| 2003/0068370 A1 | 4/2003 | Sackler et al. |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1 | 4/2003 | Chen et al. |
| 2003/0077327 A1 | 4/2003 | Durig et al. |
| 2003/0091630 A1 | 5/2003 | Louie-Helm et al. |
| 2003/0092724 A1 | 5/2003 | Huaihung et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1 | 7/2003 | Oshlack et al. |
| 2003/0152622 A1 | 8/2003 | Louie-Helm et al. |
| 2003/0158242 A1 | 8/2003 | Kugelmann |
| 2003/0158265 A1 | 8/2003 | Radhakrishnan et al. |
| 2003/0175326 A1 | 9/2003 | Thombre |
| 2003/0198677 A1 | 10/2003 | Pryce Lewis et al. |
| 2003/0215508 A1 | 11/2003 | Davis et al. |
| 2003/0224051 A1 | 12/2003 | Fink et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0049079 A1 | 3/2004 | Murray et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0170680 A1 | 9/2004 | Oshlack et al. |
| 2004/0185105 A1 | 9/2004 | Berner et al. |
| 2004/0213845 A1 | 10/2004 | Sugihara |
| 2004/0213848 A1 | 10/2004 | Li et al. |
| 2004/0253310 A1* | 12/2004 | Fischer ............... A61K 9/0092 424/472 |
| 2005/0015730 A1 | 1/2005 | Gunturi et al. |
| 2005/0031546 A1 | 2/2005 | Bartholomaeus et al. |
| 2005/0058706 A1 | 3/2005 | Bartholomaeus et al. |
| 2005/0063214 A1 | 3/2005 | Takashima |
| 2005/0079138 A1 | 4/2005 | Chickering III, et al. |
| 2005/0089475 A1 | 4/2005 | Gruber |
| 2005/0089569 A1 | 4/2005 | Bar-Shalom |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaeus et al. |
| 2005/0181046 A1 | 8/2005 | Oshlack et al. |
| 2005/0186139 A1 | 8/2005 | Bartholomaeus et al. |
| 2005/0191244 A1 | 9/2005 | Bartholomaeus et al. |
| 2005/0191352 A1 | 9/2005 | Hayes |
| 2005/0192333 A1 | 9/2005 | Hinze et al. |
| 2005/0214223 A1 | 9/2005 | Bartholomaeus et al. |
| 2005/0220877 A1 | 10/2005 | Patel |
| 2005/0222188 A1 | 10/2005 | Chapman et al. |
| 2005/0236741 A1 | 10/2005 | Arkenau et al. |
| 2005/0245556 A1 | 11/2005 | Brogman et al. |
| 2005/0266084 A1 | 12/2005 | Li et al. |
| 2005/0271594 A1 | 12/2005 | Groenewoud |
| 2006/0002859 A1 | 1/2006 | Arkenau et al. |
| 2006/0002860 A1 | 1/2006 | Bartholomaus et al. |
| 2006/0004034 A1 | 1/2006 | Hinze et al. |
| 2006/0009478 A1 | 1/2006 | Friedman et al. |
| 2006/0017916 A1 | 1/2006 | Clarke et al. |
| 2006/0039864 A1 | 2/2006 | Bartholomaus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi |
| 2006/0182801 A1 | 8/2006 | Breder et al. |
| 2006/0188447 A1 | 8/2006 | Arkenau-Maric et al. |
| 2006/0193782 A1 | 8/2006 | Bartholomeus et al. |
| 2006/0193914 A1 | 8/2006 | Ashworth et al. |
| 2006/0194759 A1 | 8/2006 | Eidelson |
| 2006/0194826 A1 | 8/2006 | Oshlack et al. |
| 2006/0240105 A1 | 10/2006 | Devane et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0042044 A1 | 2/2007 | Fischer et al. |
| 2007/0048228 A1 | 3/2007 | Arkenau-Maric et al. |
| 2007/0048373 A1 | 3/2007 | Chastain et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |

(56) References Cited

U.S. PATENT DOCUMENTS

| | | |
|---|---|---|
| 2007/0184117 A1 | 8/2007 | Gregory et al. |
| 2007/0190142 A1 | 8/2007 | Breitenbach et al. |
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1 | 10/2007 | Emigh et al. |
| 2007/0259045 A1 | 11/2007 | Mannion et al. |
| 2007/0264327 A1 | 11/2007 | Kumar et al. |
| 2007/0269505 A1 | 11/2007 | Flath et al. |
| 2007/0292508 A1 | 12/2007 | Szamosi et al. |
| 2008/0020032 A1 | 1/2008 | Crowley et al. |
| 2008/0063725 A1 | 3/2008 | Guimberteau et al. |
| 2008/0069871 A1 | 3/2008 | Vaughn et al. |
| 2008/0075669 A1 | 3/2008 | Soscia et al. |
| 2008/0075768 A1 | 3/2008 | Vaughn et al. |
| 2008/0081290 A1 | 3/2008 | Wada et al. |
| 2008/0085304 A1 | 4/2008 | Baichwal et al. |
| 2008/0131503 A1 | 6/2008 | Holm et al. |
| 2008/0145429 A1 | 6/2008 | Leyenecker et al. |
| 2008/0152595 A1 | 6/2008 | Emigh et al. |
| 2008/0181932 A1 | 7/2008 | Bortz et al. |
| 2008/0220079 A1 | 9/2008 | Chen |
| 2008/0233178 A1 | 9/2008 | Reidenberg et al. |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0260836 A1 | 10/2008 | Boyd |
| 2008/0280975 A1 | 11/2008 | Badul |
| 2008/0311049 A1 | 12/2008 | Arkenau-Maric et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |
| 2008/0317695 A1 | 12/2008 | Everaert et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |
| 2009/0081290 A1 | 3/2009 | McKenna et al. |
| 2009/0087486 A1 | 4/2009 | Krumme |
| 2009/0117191 A1 | 5/2009 | Brown Miller et al. |
| 2009/0143478 A1 | 6/2009 | Richardson et al. |
| 2009/0202634 A1* | 8/2009 | Jans .................. A61K 9/2018 424/468 |
| 2009/0215808 A1 | 8/2009 | Yum et al. |
| 2009/0232887 A1 | 9/2009 | Odidi et al. |
| 2009/0253730 A1 | 10/2009 | Kumar et al. |
| 2009/0317355 A1 | 12/2009 | Roth et al. |
| 2009/0318395 A1 | 12/2009 | Schramm et al. |
| 2010/0015223 A1 | 1/2010 | Cailly-Deufestel et al. |
| 2010/0035886 A1 | 2/2010 | Cincotta et al. |
| 2010/0047345 A1 | 2/2010 | Crowley et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Andersen et al. |
| 2010/0221322 A1 | 9/2010 | Bartholomaus et al. |
| 2010/0239667 A1 | 9/2010 | Hemmingsen et al. |
| 2010/0249045 A1 | 9/2010 | Babul |
| 2010/0260833 A1 | 10/2010 | Bartholomaus et al. |
| 2010/0280047 A1 | 11/2010 | Kolter et al. |
| 2010/0291205 A1 | 11/2010 | Downie et al. |
| 2010/0297229 A1 | 11/2010 | Sesha |
| 2010/0316712 A1 | 12/2010 | Nangia et al. |
| 2011/0020451 A1 | 1/2011 | Bartholomaus et al. |
| 2011/0020454 A1 | 1/2011 | Lamarca Casado |
| 2011/0038930 A1 | 2/2011 | Barnscheib et al. |
| 2011/0082214 A1 | 4/2011 | Faure et al. |
| 2011/0092515 A1 | 4/2011 | Qiu et al. |
| 2011/0097404 A1 | 4/2011 | Oshlack et al. |
| 2011/0129535 A1 | 6/2011 | Mantelle |
| 2011/0159100 A1 | 6/2011 | Anderson et al. |
| 2011/0187017 A1 | 8/2011 | Haupts |
| 2011/0223244 A1 | 9/2011 | Liversidge et al. |
| 2011/0245783 A1 | 10/2011 | Stinchcomb |
| 2011/0262496 A1 | 10/2011 | Desai |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholomaus et al. |
| 2012/0108622 A1 | 5/2012 | Wright et al. |
| 2012/0135071 A1 | 5/2012 | Bartholomaus et al. |
| 2012/0136021 A1 | 5/2012 | Barnscheid et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0321716 A1 | 12/2012 | Vachon et al. |
| 2013/0017262 A1 | 1/2013 | Mullen et al. |
| 2013/0028970 A1 | 1/2013 | Schwier et al. |
| 2013/0028972 A1 | 1/2013 | Schwier et al. |
| 2013/0059010 A1 | 3/2013 | Herry et al. |
| 2013/0090349 A1 | 4/2013 | Gei Ler et al. |
| 2013/0129825 A1 | 5/2013 | Billoet et al. |
| 2013/0129826 A1 | 5/2013 | Gei Ler et al. |
| 2013/0171075 A1 | 7/2013 | Arkenau-Maric et al. |
| 2013/0209557 A1 | 8/2013 | Barnscheid et al. |
| 2013/0225625 A1 | 8/2013 | Barnscheid et al. |
| 2013/0251643 A1 | 9/2013 | Bartholomäus et al. |
| 2013/0289062 A1 | 10/2013 | Kumar et al. |
| 2013/0303623 A1 | 11/2013 | Barnscheid et al. |
| 2013/0330409 A1 | 12/2013 | Mohammad |
| 2014/0010874 A1 | 1/2014 | Sackler |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau Maric et al. |
| 2014/0112989 A1 | 4/2014 | Bartholomäus et al. |
| 2014/0170079 A1 | 6/2014 | Arkenau Maric et al. |
| 2014/0186440 A1 | 7/2014 | Han et al. |
| 2014/0275143 A1 | 9/2014 | Devarakonda et al. |
| 2014/0356426 A1 | 12/2014 | Barnscheid et al. |
| 2014/0356428 A1 | 12/2014 | Barnscheid et al. |
| 2014/0378498 A1 | 12/2014 | Devarakonda et al. |
| 2015/0017250 A1 | 1/2015 | Wenig et al. |
| 2015/0030677 A1 | 1/2015 | Adjei et al. |
| 2015/0064250 A1 | 3/2015 | Ghebre-Sellassie et al. |
| 2015/0079150 A1 | 3/2015 | Fischer et al. |
| 2015/0118300 A1 | 4/2015 | Haswani et al. |
| 2015/0118302 A1 | 4/2015 | Haswani et al. |
| 2015/0118303 A1 | 4/2015 | Haswani et al. |
| 2015/0190348 A1 | 7/2015 | Haksar et al. |
| 2015/0374630 A1 | 12/2015 | Arkenau Maric et al. |
| 2016/0089439 A1 | 3/2016 | Rajagopalan |
| 2016/0175256 A1 | 6/2016 | Bartholomaeus et al. |
| 2016/0184297 A1 | 6/2016 | Arkenau-Maric et al. |
| 2016/0256456 A1 | 9/2016 | Caruso et al. |
| 2016/0263037 A1 | 9/2016 | Arkenau-Maric et al. |
| 2016/0361308 A1 | 12/2016 | Bartholomaeus et al. |
| 2016/0367549 A1 | 12/2016 | Bartholomaeus et al. |
| 2017/0027886 A1 | 2/2017 | Bartholomaeus et al. |

FOREIGN PATENT DOCUMENTS

| | | |
|---|---|---|
| AR | 049562 A1 | 8/2006 |
| AR | 049839 A1 | 9/2006 |
| AR | 053304 A1 | 5/2007 |
| AR | 054222 A1 | 6/2007 |
| AR | 054328 A1 | 6/2007 |
| AU | 769807 B2 | 3/2001 |
| AU | 2003237944 A1 | 12/2003 |
| AU | 2003274071 A1 | 5/2004 |
| AU | 2003278133 A1 | 5/2004 |
| AU | 2003279317 A1 | 5/2004 |

(56) References Cited

FOREIGN PATENT DOCUMENTS

| | | |
|---|---|---|
| AU | 2004264666 B2 | 2/2005 |
| AU | 2004264667 A1 | 2/2005 |
| AU | 2004308653 B2 | 4/2005 |
| AU | 2005259476 B2 | 1/2006 |
| AU | 2005259478 B2 | 1/2006 |
| AU | 2006210145 A1 | 8/2006 |
| AU | 2006210145 B2 | 8/2006 |
| AU | 2009207796 A1 | 7/2009 |
| AU | 2009243681 A1 | 11/2009 |
| AU | 2009299810 B2 | 4/2010 |
| AU | 2006311116 B2 | 1/2013 |
| BR | PI0413318 A | 10/2006 |
| BR | PI0413361 A | 10/2006 |
| BR | PI0513300 A | 5/2008 |
| BR | PI0606145 A2 | 2/2009 |
| CA | 0722109 A | 11/1965 |
| CA | 2082573 C | 5/1993 |
| CA | 2577233 A1 | 10/1997 |
| CA | 2650637 A1 | 10/1997 |
| CA | 2229621 A1 | 3/1998 |
| CA | 2317747 A1 | 7/1999 |
| CA | 2343234 A1 | 3/2000 |
| CA | 2352874 A1 | 6/2000 |
| CA | 2414349 A1 | 1/2002 |
| CA | 2456322 A1 | 2/2003 |
| CA | 2502965 A1 | 5/2004 |
| CA | 2503155 A1 | 5/2004 |
| CA | 2534925 A1 | 2/2005 |
| CA | 2534932 A1 | 2/2005 |
| CA | 2489855 A1 | 4/2005 |
| CA | 2551231 A1 | 7/2005 |
| CA | 2572352 A1 | 1/2006 |
| CA | 2572491 A1 | 1/2006 |
| CA | 2595954 A1 | 7/2006 |
| CA | 2229650 C | 8/2006 |
| CA | 2594713 A1 | 8/2006 |
| CA | 2595979 A1 | 8/2006 |
| CA | 2625055 A1 | 4/2007 |
| CA | 2713128 A1 | 7/2009 |
| CA | 2723438 A1 | 11/2009 |
| CA | 2595954 C | 1/2011 |
| CH | 689109 A5 | 10/1998 |
| CL | 20162004 | 5/2005 |
| CL | 20172004 A1 | 5/2005 |
| CL | 200403308 A1 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |
| CN | 87102755 A | 10/1987 |
| CN | 1135175 A | 11/1996 |
| CN | 1473562 A | 2/2004 |
| CN | 1980643 A | 4/2005 |
| CN | 101010071 A | 6/2005 |
| CN | 1671475 A | 9/2005 |
| CN | 101022787 A | 1/2006 |
| CN | 1863513 A | 11/2006 |
| CN | 1863514 A | 11/2006 |
| CN | 1917862 A | 2/2007 |
| CN | 1942174 A | 4/2007 |
| CN | 101011395 A | 8/2007 |
| CN | 101027044 A | 8/2007 |
| CN | 101057849 A | 10/2007 |
| CN | 101484135 A | 11/2007 |
| CN | 101091721 | 12/2007 |
| CN | 101111232 A | 1/2008 |
| CN | 101175482 A | 2/2008 |
| CN | 101370485 A | 2/2009 |
| CN | 101394839 A | 3/2009 |
| CN | 101578096 A | 11/2009 |
| CN | 101652128 A | 2/2010 |
| CN | 102413835 A | 4/2012 |
| CN | 102821757 A | 12/2012 |
| DE | 2530563 A1 | 1/1977 |
| DE | 4229085 A1 | 3/1994 |
| DE | 4309528 A1 | 9/1994 |
| DE | 4446470 A1 | 6/1996 |
| DE | 69400215 T2 | 10/1996 |
| DE | 19522899 C1 | 12/1996 |
| DE | 2808505 A1 | 1/1997 |
| DE | 19753534 A1 | 6/1999 |
| DE | 19800689 C1 | 7/1999 |
| DE | 19800698 A1 | 7/1999 |
| DE | 19822979 A1 | 12/1999 |
| DE | 69229881 T2 | 12/1999 |
| DE | 19855440 A1 | 6/2000 |
| DE | 19856147 A1 | 6/2000 |
| DE | 19940740 A1 | 3/2001 |
| DE | 19960494 A1 | 6/2001 |
| DE | 10036400 A1 | 6/2002 |
| DE | 69429710 T2 | 8/2002 |
| DE | 10250083 A1 | 12/2003 |
| DE | 10250084 A1 | 5/2004 |
| DE | 10250087 A1 | 5/2004 |
| DE | 10250088 A1 | 5/2004 |
| DE | 10336400 A1 | 3/2005 |
| DE | 10361596 A1 | 9/2005 |
| DE | 102004019916 A1 | 11/2005 |
| DE | 102004020220 A1 | 11/2005 |
| DE | 102004032049 A1 | 1/2006 |
| DE | 102004032051 A1 | 1/2006 |
| DE | 102004032103 A | 1/2006 |
| DE | 102005005446 A1 | 8/2006 |
| DE | 102005005449 A1 | 8/2006 |
| DE | 102007011485 A1 | 9/2008 |
| DK | 1658055 T3 | 7/2007 |
| DK | 1658084 T3 | 10/2007 |
| DK | 1515702 T2 | 1/2009 |
| EC | SP066345 A | 8/2006 |
| EP | 0008131 A1 | 2/1980 |
| EP | 0043254 A1 | 1/1982 |
| EP | 0008131 B1 | 12/1982 |
| EP | 0177893 A2 | 4/1986 |
| EP | 0216453 A2 | 4/1987 |
| EP | 0226061 A2 | 6/1987 |
| EP | 0228417 A1 | 7/1987 |
| EP | 0229652 A2 | 7/1987 |
| EP | 0232877 A1 | 8/1987 |
| EP | 0239973 A2 | 10/1987 |
| EP | 0240906 A2 | 10/1987 |
| EP | 0261616 A2 | 3/1988 |
| EP | 0261616 A3 | 3/1988 |
| EP | 0270954 A1 | 6/1988 |
| EP | 0277289 A1 | 8/1988 |
| EP | 0293066 A2 | 11/1988 |
| EP | 0328775 A1 | 8/1989 |
| EP | 0358105 A1 | 3/1990 |
| EP | 0228417 B1 | 9/1990 |
| EP | 0229652 B1 | 10/1991 |
| EP | 0477135 A1 | 3/1992 |
| EP | 0277289 B1 | 4/1992 |
| EP | 0293066 B1 | 4/1993 |
| EP | 0270954 B1 | 5/1993 |
| EP | 0544144 A1 | 6/1993 |
| EP | 0583726 A2 | 2/1994 |
| EP | 0598606 A1 | 5/1994 |
| EP | 0636370 A1 | 2/1995 |
| EP | 0641195 A1 | 3/1995 |
| EP | 0647448 A1 | 4/1995 |
| EP | 0654263 A1 | 5/1995 |
| EP | 0661045 A1 | 7/1995 |
| EP | 0675710 A1 | 10/1995 |
| EP | 0682945 A2 | 11/1995 |
| EP | 0693475 A1 | 1/1996 |
| EP | 0820693 A1 | 1/1996 |
| EP | 0696598 A1 | 2/1996 |
| EP | 0216453 B1 | 3/1996 |
| EP | 0583726 B1 | 11/1996 |
| EP | 0756480 A1 | 2/1997 |
| EP | 0760654 A1 | 3/1997 |
| EP | 0761211 A1 | 3/1997 |
| EP | 0780369 A1 | 6/1997 |
| EP | 0785775 A1 | 7/1997 |

(56) References Cited

FOREIGN PATENT DOCUMENTS

| | | |
|---|---|---|
| EP | 0809488 A1 | 12/1997 |
| EP | 0820698 A1 | 1/1998 |
| EP | 0820753 A2 | 1/1998 |
| EP | 0857062 A2 | 8/1998 |
| EP | 0864324 A2 | 9/1998 |
| EP | 0864326 A2 | 9/1998 |
| EP | 0598606 B1 | 6/1999 |
| EP | 0675710 B1 | 8/1999 |
| EP | 0980894 A1 | 2/2000 |
| EP | 0988106 A1 | 3/2000 |
| EP | 1014941 A1 | 7/2000 |
| EP | 1070504 A1 | 1/2001 |
| EP | 1127871 A1 | 8/2001 |
| EP | 1138321 A2 | 10/2001 |
| EP | 1152026 A1 | 11/2001 |
| EP | 1138321 A3 | 1/2002 |
| EP | 1166776 A2 | 1/2002 |
| EP | 1201233 A1 | 5/2002 |
| EP | 0661045 B1 | 7/2002 |
| EP | 1250045 A2 | 10/2002 |
| EP | 1251120 A1 | 10/2002 |
| EP | 1293127 A2 | 3/2003 |
| EP | 1293195 A1 | 3/2003 |
| EP | 1293196 A2 | 3/2003 |
| EP | 1127871 B1 | 9/2003 |
| EP | 1201233 B1 | 12/2004 |
| EP | 1251120 B1 | 12/2004 |
| EP | 1492506 B1 | 1/2005 |
| EP | 1166776 B1 | 2/2005 |
| EP | 1502592 A1 | 2/2005 |
| EP | 1658054 A1 | 2/2005 |
| EP | 1658055 A1 | 2/2005 |
| EP | 1515702 B1 | 3/2005 |
| EP | 1527775 A1 | 4/2005 |
| EP | 1558221 A1 | 8/2005 |
| EP | 1558257 A1 | 8/2005 |
| EP | 1560585 B1 | 8/2005 |
| EP | 1611880 A2 | 1/2006 |
| EP | 1658054 B1 | 5/2006 |
| EP | 1138321 B1 | 1/2007 |
| EP | 1740161 A2 | 1/2007 |
| EP | 1658055 B1 | 3/2007 |
| EP | 1765303 A1 | 3/2007 |
| EP | 1786403 A1 | 5/2007 |
| EP | 1558221 B1 | 6/2007 |
| EP | 1813276 A1 | 8/2007 |
| EP | 1842533 A2 | 10/2007 |
| EP | 1845955 A1 | 10/2007 |
| EP | 1845956 A1 | 10/2007 |
| EP | 1859789 A1 | 11/2007 |
| EP | 1980245 A1 | 10/2008 |
| EP | 1897545 A1 | 12/2008 |
| EP | 2131830 A2 | 12/2009 |
| EP | 2246063 A1 | 11/2010 |
| EP | 2249811 A1 | 11/2010 |
| EP | 2273983 A1 | 1/2011 |
| EP | 2402004 A2 | 1/2012 |
| ES | 2336571 T3 | 12/2004 |
| ES | 2260042 T3 | 11/2006 |
| ES | 2285497 T3 | 11/2007 |
| ES | 2288621 T3 | 1/2008 |
| ES | 2289542 T3 | 2/2008 |
| ES | 2315505 T3 | 4/2009 |
| GB | 1147210 A | 4/1969 |
| GB | 1567727 A | 5/1980 |
| GB | 2047095 A | 11/1980 |
| GB | 2057878 A | 4/1981 |
| GB | 2238478 A | 6/1991 |
| HR | 20070456 T3 | 6/2007 |
| HR | 20070272 T3 | 11/2007 |
| JP | S36-022895 | 11/1961 |
| JP | S55162714 A | 12/1980 |
| JP | S5659708 A | 5/1981 |
| JP | S56169622 A | 12/1981 |
| JP | S62240061 A | 10/1987 |
| JP | H0249719 A | 2/1990 |
| JP | 03-501737 A | 4/1991 |
| JP | H0517566 A | 1/1993 |
| JP | H06507645 A | 9/1994 |
| JP | 08053331 A | 2/1996 |
| JP | 8-505076 A | 6/1996 |
| JP | H09508410 A | 8/1997 |
| JP | H1057450 A | 3/1998 |
| JP | H10251149 A | 9/1998 |
| JP | 2000513333 A | 10/2000 |
| JP | 2002524150 A | 8/2002 |
| JP | 2002-275175 A | 9/2002 |
| JP | 2003113119 A | 4/2003 |
| JP | 2003125706 A | 5/2003 |
| JP | 2003526598 A | 9/2003 |
| JP | 2004143071 A | 5/2004 |
| JP | 2005506965 A | 3/2005 |
| JP | 2005515152 A | 5/2005 |
| JP | 2005534664 A | 11/2005 |
| JP | 2007501201 A | 1/2007 |
| JP | 2007501202 A | 1/2007 |
| JP | 2007513147 A | 5/2007 |
| JP | 2007533692 A | 11/2007 |
| JP | 2008024603 A | 2/2008 |
| JP | 2008504327 A | 2/2008 |
| JP | 2008528654 A | 7/2008 |
| JP | 2009523833 A | 6/2009 |
| JP | 2009524626 A | 7/2009 |
| JP | 2009531453 A | 9/2009 |
| JP | 2009536927 A | 10/2009 |
| JP | 2009537456 A | 10/2009 |
| JP | 2010534204 A | 11/2010 |
| JP | 2011504455 A | 2/2011 |
| JP | 2011506493 A | 3/2011 |
| JP | 2011510034 A | 3/2011 |
| JP | WO 2011/059074 A1 | 5/2011 |
| JP | 2012515735 A | 7/2012 |
| JP | 2012528845 A | 11/2012 |
| JP | 2013523804 A | 6/2013 |
| JP | 2013155124 A | 8/2013 |
| JP | 2013536810 A | 9/2013 |
| JP | 2014505736 A | 3/2014 |
| JP | 2014528437 A | 10/2014 |
| JP | 6085307 B2 | 2/2017 |
| JP | 2013523780 A | 6/2017 |
| KR | 1020060069832 A | 6/2006 |
| KR | 20070039041 A | 4/2007 |
| KR | 20070111510 A | 11/2007 |
| KR | 20090085312 A | 8/2009 |
| KR | 20100111303 A | 10/2010 |
| KR | 20110016921 A | 2/2011 |
| MX | 2007000008 A | 3/2007 |
| MX | 2007000009 A | 3/2007 |
| MX | 2007009393 A | 8/2007 |
| MX | 2010008138 A | 8/2010 |
| MX | 2010012039 A | 11/2010 |
| NO | 20061054 A | 3/2006 |
| NO | 20070578 A | 1/2007 |
| NO | 20074412 A | 11/2007 |
| NZ | 528302 A | 2/2007 |
| PT | 1699440 E | 12/2004 |
| PT | 1658054 E | 5/2006 |
| PT | 1658055 E | 7/2007 |
| PT | 1515702 E | 12/2008 |
| RU | 2131244 C1 | 6/1999 |
| RU | 2198197 C2 | 2/2003 |
| RU | 2220715 C2 | 1/2004 |
| RU | 2328275 C2 | 5/2004 |
| RU | 2396944 C2 | 7/2004 |
| RU | 2326654 C2 | 9/2005 |
| RU | 2339365 C2 | 12/2007 |
| RU | 2354357 C2 | 12/2007 |
| RU | 2007103712 A | 9/2008 |
| RU | 2007103707 A | 11/2008 |
| RU | 2007132975 A | 4/2009 |
| RU | 2567723 C2 | 11/2015 |
| SI | 1515702 T1 | 4/2009 |
| SI | 1699440 T1 | 11/2009 |
| SK | 10612003 A3 | 1/2004 |

(56) References Cited

FOREIGN PATENT DOCUMENTS

| | | |
|---|---|---|
| SU | 1759445 A1 | 9/1992 |
| TW | 1254634 B | 5/2006 |
| WO | WO 1980/000841 A1 | 5/1980 |
| WO | WO 1989/005624 A1 | 6/1989 |
| WO | WO 1900/003776 A1 | 4/1990 |
| WO | WO 1993/006723 A1 | 4/1993 |
| WO | WO 93/10765 A1 | 6/1993 |
| WO | WO 1993/011749 A1 | 6/1993 |
| WO | WO 1993/919758 A1 | 6/1993 |
| WO | WO 1993/023017 A1 | 11/1993 |
| WO | WO 1994/006414 A1 | 3/1994 |
| WO | WO 1994/008567 A1 | 4/1994 |
| WO | WO 1995/017174 A1 | 6/1995 |
| WO | WO 1995/020947 A1 | 8/1995 |
| WO | WO 1995/022319 A1 | 8/1995 |
| WO | WO 1995/030422 A1 | 11/1995 |
| WO | WO 1996/000066 A1 | 1/1996 |
| WO | WO 1996/003979 A1 | 2/1996 |
| WO | WO 1996/014058 A1 | 5/1996 |
| WO | WO 1997/000673 A1 | 1/1997 |
| WO | WO 1997/033566 A2 | 9/1997 |
| WO | WO 1997/049384 A1 | 12/1997 |
| WO | WO 1998/035655 A3 | 2/1998 |
| WO | WO 1998/020073 A2 | 5/1998 |
| WO | WO 1998/028698 A1 | 7/1998 |
| WO | WO 1998/035655 A2 | 8/1998 |
| WO | WO 1998/051758 A1 | 11/1998 |
| WO | WO 1999/012864 A1 | 3/1999 |
| WO | WO 1999/032120 A1 | 7/1999 |
| WO | WO 1999/044591 A1 | 9/1999 |
| WO | WO 1999/045887 A2 | 9/1999 |
| WO | WO 1999/048481 A1 | 9/1999 |
| WO | WO 2000/013647 A1 | 3/2000 |
| WO | WO 2000/033835 A1 | 6/2000 |
| WO | WO 2000/040205 A2 | 7/2000 |
| WO | WO 2001/008661 A2 | 2/2001 |
| WO | WO 2001/012230 A1 | 2/2001 |
| WO | WO 2001/015667 A1 | 3/2001 |
| WO | WO 2001/052651 A2 | 7/2001 |
| WO | WO 2001/058451 A1 | 8/2001 |
| WO | WO 2001/097783 A1 | 12/2001 |
| WO | WO 2002/026061 A1 | 4/2002 |
| WO | WO 2002/026262 A2 | 4/2002 |
| WO | WO 2002/026928 A1 | 4/2002 |
| WO | WO 2002/035991 A2 | 5/2002 |
| WO | WO 2002/071860 A1 | 9/2002 |
| WO | WO 2002/088217 A1 | 11/2002 |
| WO | WO 2002/094254 A2 | 11/2002 |
| WO | WO 2003/006723 A1 | 1/2003 |
| WO | WO 2003/007802 A2 | 1/2003 |
| WO | WO 2003/013433 A2 | 2/2003 |
| WO | WO 2003/013476 A1 | 2/2003 |
| WO | WO 2003/013479 A1 | 2/2003 |
| WO | WO 2003/013538 A1 | 2/2003 |
| WO | WO 2003/015531 A2 | 2/2003 |
| WO | WO 2003/018015 A1 | 3/2003 |
| WO | WO 2003/024426 A1 | 3/2003 |
| WO | WO 2003/024430 A1 | 3/2003 |
| WO | WO 2003/026624 A1 | 4/2003 |
| WO | WO 2003/026743 A2 | 4/2003 |
| WO | WO 2003/028698 A1 | 4/2003 |
| WO | WO 2003/028990 A1 | 4/2003 |
| WO | WO 2003/031546 A1 | 4/2003 |
| WO | WO 2003/035029 A1 | 5/2003 |
| WO | WO 2003/035053 A1 | 5/2003 |
| WO | WO 2003/035054 A1 | 5/2003 |
| WO | WO 2003/035177 A2 | 5/2003 |
| WO | WO 2003/039561 A1 | 5/2003 |
| WO | WO 2003/049689 A2 | 6/2003 |
| WO | WO 2003/053417 A2 | 7/2003 |
| WO | WO 2003/068392 A1 | 8/2003 |
| WO | WO 2003/070191 A1 | 8/2003 |
| WO | WO 2003/092648 A1 | 11/2003 |
| WO | WO 2003/094812 A1 | 11/2003 |
| WO | WO 2003/105808 A1 | 12/2003 |
| WO | WO 2004/004693 A1 | 1/2004 |
| WO | WO 2004/043967 A1 | 2/2004 |
| WO | WO 2004/026262 A2 | 4/2004 |
| WO | WO 2004/026263 A2 | 4/2004 |
| WO | WO 2004/026280 A2 | 4/2004 |
| WO | WO 2004/037222 A2 | 5/2004 |
| WO | WO 2004/037230 A1 | 5/2004 |
| WO | WO 2004/037259 A1 | 5/2004 |
| WO | WO 2004/037260 A1 | 5/2004 |
| WO | WO 2004/043449 A1 | 5/2004 |
| WO | WO 2004/066910 A2 | 8/2004 |
| WO | WO 2004/078212 A1 | 9/2004 |
| WO | WO 2004/084869 A1 | 10/2004 |
| WO | WO 2004/093801 A2 | 11/2004 |
| WO | WO 2004/093819 A2 | 11/2004 |
| WO | WO 2004/098567 A2 | 11/2004 |
| WO | WO 2004/100894 A2 | 11/2004 |
| WO | WO 2005/016313 A1 | 2/2005 |
| WO | WO 2005/016314 A1 | 2/2005 |
| WO | WO 2005/032524 A2 | 4/2005 |
| WO | WO 2005/041968 A2 | 5/2005 |
| WO | WO 2005/053587 A1 | 6/2005 |
| WO | WO 2005/053656 A1 | 6/2005 |
| WO | WO 2005/055981 A2 | 6/2005 |
| WO | WO 2005/060942 A1 | 7/2005 |
| WO | WO 2005/063214 A1 | 7/2005 |
| WO | WO 2005/065646 A2 | 7/2005 |
| WO | WO 2005/066183 A1 | 7/2005 |
| WO | WO 2005/079760 A1 | 9/2005 |
| WO | WO 2003/102286 A1 | 11/2005 |
| WO | WO 2005/102286 A1 | 11/2005 |
| WO | WO 2005/102294 A2 | 11/2005 |
| WO | WO 2005/102294 A3 | 11/2005 |
| WO | WO 2005/105036 A1 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/002884 B1 | 3/2006 |
| WO | WO 2006/039692 A2 | 4/2006 |
| WO | WO 2006/058249 A2 | 6/2006 |
| WO | WO 2006/082097 A1 | 8/2006 |
| WO | WO 2006/082099 A1 | 8/2006 |
| WO | WO 2006/105615 A1 | 10/2006 |
| WO | WO 2006/128471 A2 | 12/2006 |
| WO | WO 2007/005716 A2 | 1/2007 |
| WO | WO 2007/008752 A2 | 1/2007 |
| WO | WO 2007/014061 A2 | 2/2007 |
| WO | WO 2007/048233 A1 | 5/2007 |
| WO | WO 2007/053698 A2 | 5/2007 |
| WO | WO 2007/085024 A2 | 7/2007 |
| WO | WO 2007/085024 A3 | 7/2007 |
| WO | WO 2007/093642 A2 | 8/2007 |
| WO | WO 2007/103105 A2 | 9/2007 |
| WO | WO 2007/103286 A2 | 9/2007 |
| WO | WO 2007/112273 A2 | 10/2007 |
| WO | WO 2007/112285 A2 | 10/2007 |
| WO | WO 2007/112286 A2 | 10/2007 |
| WO | WO 2007/131357 A1 | 11/2007 |
| WO | WO 2008/023261 A1 | 2/2008 |
| WO | WO 2008/033523 A1 | 3/2008 |
| WO | WO 2008/045060 A1 | 4/2008 |
| WO | WO 2008/069941 A2 | 6/2008 |
| WO | WO 2008/086804 A2 | 7/2008 |
| WO | WO 2008/107149 A2 | 9/2008 |
| WO | WO 2008/107149 A3 | 9/2008 |
| WO | WO 2008/109462 A2 | 9/2008 |
| WO | WO 2008/132707 A1 | 11/2008 |
| WO | WO 2008/142627 A2 | 11/2008 |
| WO | WO 2008/148798 A2 | 12/2008 |
| WO | WO 2009/005803 A1 | 1/2009 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | WO 2009/092601 A1 | 7/2009 |
| WO | WO 2009/110005 A2 | 9/2009 |

(56) References Cited

FOREIGN PATENT DOCUMENTS

| | | |
|---|---|---|
| WO | WO 2009/112273 A2 | 9/2009 |
| WO | WO 2009/135680 A1 | 11/2009 |
| WO | WO 2010/022193 A2 | 2/2010 |
| WO | WO 2010/037854 A2 | 4/2010 |
| WO | WO 2010/044842 A1 | 4/2010 |
| WO | WO 2010/057036 A2 | 5/2010 |
| WO | WO 2010/066034 A1 | 6/2010 |
| WO | WO 2010/069050 A1 | 6/2010 |
| WO | WO 2010/083843 A1 | 7/2010 |
| WO | WO 2010/083894 A1 | 7/2010 |
| WO | WO 2010/088911 A1 | 8/2010 |
| WO | WO 2010/105672 A1 | 9/2010 |
| WO | WO 2010/140007 A2 | 12/2010 |
| WO | WO 2010/140007 A9 | 12/2010 |
| WO | WO 2010/149169 A2 | 12/2010 |
| WO | WO 2011/008298 A2 | 1/2011 |
| WO | WO 2011/009602 A1 | 1/2011 |
| WO | WO 2011/009603 A1 | 1/2011 |
| WO | WO 2011/009604 A1 | 1/2011 |
| WO | WO 2011/095314 A2 | 8/2011 |
| WO | WO 2011/095314 A3 | 8/2011 |
| WO | WO 2011/124953 A2 | 10/2011 |
| WO | WO 2011/124953 A3 | 10/2011 |
| WO | WO 2011/128630 A2 | 10/2011 |
| WO | WO 2011/141241 A1 | 11/2011 |
| WO | WO 2011/154414 A1 | 12/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/061779 A1 | 5/2012 |
| WO | WO 2012/076907 A2 | 6/2012 |
| WO | WO 2012/085657 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A1 | 2/2013 |
| WO | WO 2013/017242 A1 | 2/2013 |
| WO | WO 2013/025449 A1 | 3/2013 |
| WO | WO 2013/030177 A1 | 3/2013 |
| WO | WO 2013/050539 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 2013/156453 A1 | 10/2013 |
| WO | WO 2013/167735 A1 | 11/2013 |
| WO | WO 2014/032741 A1 | 3/2014 |
| WO | WO 2014/059512 A1 | 4/2014 |
| WO | WO 2014/140231 A1 | 9/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/004245 A1 | 1/2015 |
| WO | WO 2015/103379 | 7/2015 |
| WO | WO 2015/120201 A1 | 8/2015 |
| WO | WO 2017/178658 A1 | 10/2017 |

OTHER PUBLICATIONS

Bruce et al, Properties of hot-melt extuded tablet formulations for the colonic delivery of 5-aminosalicylic acid, European Journal of Pharmaceutics and Biopharmaceutics, 59 (2005) 85-97.
Caraballo, Journal of Controlled Release, vol. 69, pp. 345-355, 2000.
Carbopol 71G, retrieved Mar. 10, 2014 from http://www.lubrizol.com/LifeScience/Products/Carbopol71G-NF.html.
Cawello, "Parameters for Compartment-free Pharmacokinetics—Standardization of Study Design, Data Analysis and Reporting" 1999, pp. XI-XIII (table of contents).
Committee for Proprietary Medicinal Products. Note for Guidance on the Investigation of Bioavailability and Bioequivalence. 2001. pp. 1-18.
Coppens et al , "Hypromellose, Ethylcellulose, and Polyethylene Oxide Use in Hot Melt Extrusion," Pharmaceutical Technology, 62-70, Jan. 2005.
Cornish, P. "Avoid the Crush": hazards of medication administration in patients with dysphagia or a feeding tube, CMA Media Inc., CMAJ. 172(7), pp. 871-872, 2005.
Costa et al. "Modeling and comparison of dissolution profiles"; European Journal of Pharmaceutical Sciences 13 (2001) 123-33.
Crowley M.M. et al., "Stability of polyethylene oxide in matrix tablets prepared by hot-melt extrusion," Biomaterials 23, 2002, pp. 4241-4248.
Crowley MM, Drug Dev Ind Pharm. Sep. 2007; 33(9):909-26. (Abstract only).
Dachille et al., "High-pressure Phase Transformations in Laboratory Mechanical Mixers and Mortars", Nature, vol. 186, Apr. 2, 1960, pp. 34 and 71.
Dachille, F. et al., "High-Pressure Phase Transformation in Laboratory Mechanical Mixers and Mortars", 1960., Nature, vol. 186, pp. 1-2 (abstract).
Davies, et al; European Journal of Pharmaceutics and Biopharmaceutics, 67, 2007, pp. 268-276.
Dean, D.A., E.R. Evans, I.H. Hall, Pharmaceutical Packaging Technology, Taylor & Francis, 1st Edition, Nov. 30, 2000 (Publisher description dated Oct. 22, 2010).
Deighan, C.J. et al., Rhabdomyolysis and acute renal failure resulting from alcohol and drug abuse, Q.J. Med. vol. 93, 2000, pp. 29-33.
Dejong (Pharmaceutisch Weekblad Scientific Edition) 1987, p. 24-28.
Dexheimer, Terahertz Spectroscopy: Principles and Applications (Optical Science and Engineering Series), CRC; 1 edition 2007. (Table of content only).
Dierickx et al., "Co-extrusion as manufacturing technique for fixed-dose combination mini-matrices," European Journal of Pharmaceutics and Biopharmaceutics 81 (2012), 683-689.
Disanto, Anthony. Bioavailability and Bioequivalency Testing. Chapter 77. In Remington's Pharmaceutical Sciences, 17th Ed. 1985.
Dow Chemical Company, "Using Dow Excipients for Controlled Release of Drugs in Hydrophilic Matrix Systems", Sep. 2006, pp. 1-36.
Dow Excipients Chem. of Poly. Water Soluble-Resin 2004, pp. 1-2.
Dow Technical Data, Polyox WSR Solid Dosage Formulation via Melt Extrusion, Feb. 2003, pp. 1-3.
Efentakis M et al. "Evaluation of High Molecular Weight Poly(Oxyethylene) (Polyox) Polymer: Studies of Flow Properties and Release Rates of Furosemide and Captopril from controlled-Release hard Gelatin Capsules", Pharmaceutical Development and Technology, 5 (3), pp. 339-346, 2000.
Eggleston, "The seat of the emetic action of various drugs," J. Pharmacol. Exp. Ther. 7, 225-253 (1915).
El-Egakey, Adel et al, "Hot extruded dosage forms Part I Technology and dissolution kinetics of polymeric matrices" Pharmacerutica Acta Helvetiae, vol. 46, pp. 31-53,Mar. 19, 1970.
El-Sherbiny I.M. et al "Preparation, characterization, swelling and in vitro drug release behavior of poly[N-acryloylglycine-chitosan] interplymeric pH and thermally-resposive hydrogels", European Polymer Journal, vol. 41, pp. 2584-2591, 2005.
Encyclopedia of Pharmaceutical Technology, Third Edition, vol. 1, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 2, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 3 edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 4, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 5, edited by James Swarbrick PharmaceuTech, Inc., Pinehurst, North Carolinia, USA (Table of Contents only), Oct. 25, 2006.

(56) References Cited

OTHER PUBLICATIONS

Encyclopedia of Pharmaceutical Technology, Third Edition, vol. 6, edited by James Swarbrick PharmaceuTech, Inc., Pinehurst, North Carolinia, USA (Table of Contents only), Oct. 25, 2006.
Encyclopedia of Pharmacological Technology, Informs Healthcare, 1st Ed., 1996, vol. 14 (Table of Content only).
Erskine, Jr., Clyde. Quality Assurance and Control. Chapter 83. pp. 1487-1491 In Remington's Pharmaceutical Sciences, 17th Ed. 1985.
Eudragit NE40D web page from Evonik website; downloaded Feb. 24, 2015.
Eudragit RS PO web page from Evonik website; downloaded Feb. 24, 2015.
2.9 Methoden der pharmazeutischen Technologie, European Pharmacopeia, 143-144, 1997 (Full English translation attached).
Albertini, B. "New spray congealing atomizer for the microencapsulation of highly concentrated solid and liquid substances" European Journal of Pharmaceutics and Biopharmaceutics 69 (2008) 348-357.
Almeida, A. et al., Ethylene vinyl acetate as matrix for oral sustained release dosage forms produced via hot-melt extrusion, European Journal of Pharmaceutics and Biopharmaceutics 77 (2011) 297-305.
Almeida, A. et al., Sustained release from hot-melt extruded matrices based on ethylene vinyl acetate and polyethylene oxide, European Journal of Pharmaceutics and Biopharmaceutics 82 (2012) 526-533.
Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.
Apicella A. et al., Biomaterials, vol. 14, No. 2, pp. 83-90, 1993.
Application of a modelling system in the formulation of extended release hydrophilic matrices, Reprinted from Pharmaceutical Technology. Europe, Jul. 2006.
Application of Opadry II, complete film coating system, on metformin HCl extended release matrices containing Polyox water soluble resin, Colorcon Apr. 2009.
Arnold C., "Teen Abuse of Painkiller OxyContin on the Rise," www.npr.org, Dec. 19, 2005.
Augustine, R.L., "Catalytic Hydrogenation of a, B-Unsaturated Ketones. III The Effect of Quantity and Type of Catalysts," J.Org Chem. 28(1): pp. 152-155: Abstract 1963.
Avis, Kenneth, Parenteral Preparations. Chapter 85. pp. 1518-1541In Remington's Pharmaceutical Sciences, 17th Ed. 1985.
Bailey, F.E., et al., "Some properties of poly(ethylene oxide)' in aqueous solution," Journal of Applied Polymer Science, vol. 1, Issue No. 1, pp. 56-62, 1959.
Bauer et al. Lehrbuch der Pharmazeutischen Technologie. Eight Edition 2006. Stuttgart, pp. 343-352.
Bauer et al. Lehrbuch der Pharmazeutischen Technologie, Sixth Edition 1999. Stuttgart, pp. IX-XV, Table of contents. (Full English translation attached).
James, A. "The legal and clinical implications of crushing tablet medication", Nurse Times 100(50), 28-33, 2004.
Janicki S. et al. "Slow-Release Microballs: Method of Preparation", Acta Pharm. Technol, 33(3) 154-155, 1987.
Jannetto, P. et al, "Oxycodone: Recognition and Pharmacogenomics" Toxicology News, Mar. 2003, 1-7.
Kalant H. et al., Death in Amphetamine Users: Caues and Rates, CMA Journal, vol. 112 (Feb. 8, 1975): 299-304.
Katz N. et al. "Challenges in the development of prescription opioid abuse-deterrent formulations", Clin. J. Pain, 23(8): 648-660 (Oct. 2007).
Kim C.-J. et al. "Drug Release from Compressed Hydrophilic Polyox-WSR Tablets" J Pharm. Sciences 1995, 84(3): pp. 303-306.
Kim N et al. "Preparation and Evaluation of Eudragit Gels. V. Rectal Gel Preparations for Sustained Release and Avoidance of First-Pass Metabolism of Lidocaine", Chem. Pharm Bull. 1992, 40(10), 2800-2804.
King et al. Oral Solid Dosage Forms. Chapter 90. pp. 163-1632 in Remington's Pharmaceutica Sciences, 17th Ed, 1985.
King, R, "Tablets, Capsules, and Pills" Remington's Pharmaceutical Sciences, pp. 1553-1593, Ch. 89, 1980, 16$^{th}$ Edition.
King, Remington 's Pharmaceutical Sciences 17th ed., Chapter 78, p. 1418 (1985).
Knevel, Adelbert, Separation. Chapter 78. pp. 1432-1442 in Remington's Pharmaceutical Sciences, 17th Ed, 1985.
Kolter, K., "Compression Behaviour of Kollidon SR," APV/ APGI 2002, Florence, Apr. 11, 2002.
Kondrat, T. , "Technology dosage forms" Moscow 1991, p. 96.
Lee, Y.-S. et al., Principles of Terahertz Science and Technology (Lecture Notes in Physics), Springer: 1 edition 2008. (Table of Contents Only).
Lenindzer, A., "The molecular basis of the structure and functions of cells" Moscow 1974, p. 68.
Levina et al., "The Effect of Ultrasonic Vibration on the Compaction Characteristics of Ibuprofen" Drug Development and Industrial Pharmacy, vol. 28, No. 5, pp. 495-514, 2002.
Levina M. et al "The Effect of Ultrasonic Vibration on the Compaction Characteristics of Paracetamol", Journal of Pharmaceutical Sciences, vol. 89, No. 6, pp. 705-723, Jun. 2000.
Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.
Lieberman, Herbert A., Pharmaceutical Dosage Forms, Tablets, Second Edition, Revised and Expanded 1990. vol. 2 (Cover and Table of Content only).
Lintner, Carl. Stability of Pharmaceutical Products. Chapter 82. pp. 1478-1486 in Remington's Pharmaceutical Sciences, 17th Ed, 1985.
Liu J. et al., "Properties of Lipophilic Matrix Tables Containing Phenylpropanolamine Hydrochloride Prepared by Hot-Melt Extrusion", EJPB, 52 (2001), pp. 181-190.
Lockhart H. et al, "Packaging of Pharmaceuticals and Health Care Products"; Blackie Academic & Professional: First Edition 1996, (Table of contents only).
Longer et al. Sustained-Release Drug Delivery Systems. Chapter 92. pp. 1611-1661 in Remington's Pharmaceutical Sciences, 17th Ed 1985.
Madorsky S.L. "Thermal degradation of Polyethylene Oxide and Polypropylene Oxide", Journal of Polymer Science, pp. 183-194 vol. 36, No. 3, Mar. 1959.
Maggi et al., "Dossolution behavior of hydrophilic matrix tablets containing two different polyethylene oxides (PEOs) for the controlled release of a water-soluble drug. Dimensionality study" Biomaterials, 2002, 23, 1113-1119.
Maggi L.et al, "High molecular weight polyethylene oxides (PEOs) as an alternative to HPMC in controlled release dosage form", 2000, International Journal of Pharmaceutics, 195 pp. 229-238.
Maggi, C., Therapeutic Potential of Capsaicin-like Molecules. Life Sciences, vol. 51, pp. 1777-1781, 1992.
Mank R. et al., "Darstellung wirkstoffhaltiger Extrusionsformlinge auf der Basis von Thermoplasten. Teil 1: Untersuchung zur Wirkstoffliberation" Pharmazie 44, H. 11, pp. 773-776, 1989. English language translation of relevant paragraph provided.
Mank R., "Darstellung wirkstoffhaltiger Extrusionsformlinge auf der Basis von Thermoplasten. Teil 2: Unersuchungen zur Optimierung der Wirkstofffreigabe" Pharmazie 45, H. 8, pp. 592-593 1990. English language translation of relevant paragraph provided.
Marques, Tablet breaking force, 2008.
Matos, Dr. Rick, Ph.D—Letter Jan. 6, 2011.
McGary, C.W., Jr. "Degradation of Poly(ethylene Oxide)", Journal of Polymer Science vol. XLVI,1960, pp. 51-57.
McGinty et al., Hot-Melt Extrusion as a Pharmaceutical Process, American Pharmaceutical Review, vol. 4 (2), pp. 25-36, 2001.
McGinity, J.W.—Letter of Jan. 26, 2009, pp. 1-4.
McNeill M. et al. Properties controlling the diffusion and release of water-soluble solutes from poly(ethylene oxide) hydrogels. 4. Extended constant rate release from partly-coated spheres. Journal Biomat, Sci. Polymer, Ed. 1996, vol. 7, pp. 953-963.
Mesiha M.S. et al "A Screening Study of Lubricants in Wet Powder Passes Suitable for extrusio-spheronization", Drug Development and Industrial Pharmacy, 19(8), pp. 943-959, 1993.

(56) References Cited

OTHER PUBLICATIONS

Metformin Hydrochloride 1000 mg Extended Release Tablets, Lubrizol Advanced Materials, Inc., Nov. 20, 2009, Previous Edition Dec. 19, 2008.
Metformin Hydrochloride 750 mg Extended Release Tablets, Lubrizol Advanced Materials, Inc., Sep. 2010.
Miles, R.E. et al., Terahertz Frequency Detection and Identification of Materials and Objects (NATO Science for Peace and Security Series B: Physics and Biophysics), Springer; 1 edition 2007, (Table of contents).
Miller "To crush or not to crush? What to consider before giving medications to a patent with a tube or who has trouble swallowing", Nursing, pp. 50-52, Feb. 2000.
Mises à jour cumulatives, Vidal, Jan./Oct. 2002 (full translation attached).
Mitchell, "Oral Dosage Forms That Should Not Be Crushed: 2000 Update" Hospital Pharmacy 35(5), 553-557, 2000.
Moorman-Li, R, et al, "A Review of Abuse-Deterrent Opioids for Chronic Nonmalignant Pain." Pharmacy and Therapeutics, vol. 37 No. 7, Jul. 2012, pp. 412-421.
Morissette et al. Advanced Drug Delivery Review 26 (2004), 275-300.
Moroni A. et al, "Application of Poly(Oxyethylene) Homopolymers in Sustained release Solid formulations" Drug Development and Industrial Pharmacy, 21(12) pp. 1411-1428, 1995.
European Pharmacopeia 5.0; Glyceryl behenate monograph; dated Jan. 2005; downloaded Feb. 24, 2015.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
European Pharmacopoeia, Third Edition Supplement 2000, Council of Europe, Strasbourg, 2000, pp. 85-107.
European Pharmacopoeia, Third Edition, Council of Europe, Strasbourg, 1997, pp. 127-152.
European Search Report and Opinion Application No. 12002708.1-1219, dated Sep. 24, 2012.
European Search Report and Opinion Application No. 14176277.3-1460, dated Dec. 15, 2014.
European Search Report and Opinion, Application No, 11006253.6-2112, dated Dec. 16, 2011.
European Search Report and Opinion, Application No. 11006254.4-2112, dated Dec. 16, 2011.
European Search Report and Opinion, Application No. 11008131.2-1219, dated Feb. 24, 2012.
European Search Report and Opinion, Application No. 11009129.5-2112, dated Apr. 10, 2012.
European Search Report and Opinion, Application No. 12001296.6-1219, dated Jun. 26, 2012.
European Search Report and Opinion, Application No. 12001301.7-1219, dated Jun. 26, 2012.
European Search Report and Opinion, Application No. 12003743.7-1219, dated Sep. 24, 2012.
European Search Report and Written Opinion for EP Application No. 13176309.9-1460, dated Oct. 9, 2013.
European Search Report and Written Opinion for EP Application No. 13169658.5, dated Aug. 6, 2013.
European Search Report and Written Opinion for EP Application No. 13169659.3, dated Aug. 6, 2013.
European Search Report and Written Opinion for EP Application No. 13197503.9-1460, dated Feb. 18, 2014.
European Search Report and Written Opinion for EP Application No. 13425151.1-1460, dated Mar. 11, 2014.
European Search Report and Written Opinion for EP Application No. 14169801.9-1455 dated Oct. 20, 2014.
Evaluation of Verapamil HCl (240 mg) Extended Release Matrix Formulation Using USP Apparatus III in Biorelevant Dissolution Media, Jul. 2009.
Evonik Industries, Eudragit Application Guidelines, 10th Edition, 2008, (Table of Contents only).
Evonik Rohm GmbH product brochure: Eudragit acrylic polymers for solid oral dosage forms (2009).
Fell J.T., et al, "Determinination of Tablet Strength by the Diametral-Compression Test" Journal of Pharmaceutical Sciences, vol. 59, No. 5, May 1970, pp. 688-691.
Follonier N. et al., "Evaluation of hot-melt extrusion as a new technique for the production of polymer-based pellets for sustained release capsules containing high loadings of freely soluble drugs," Drug Development and Industrial Pharmacy, 20(8), pp. 1323-1339, 1994.
Follonier, N. et al., "Various ways of modulating the release of dltiazem hydrochloride from hot-melt extruded sustained release pellets prepared using polymeric materials" Journal of Controlled Release 36, pp. 243-250, 1995.
Formulation of Polyox ER Matrices for a Highly Soluble Active, Colorcon Jul. 2009.
Foye, W., Principles of Medicinal Chemistry; Analgesics pp. 241-242, at 241 (1989).
Foye, W., Principles of Medicinal Chemistry; Structural Features and Pharmacologic Activity, pp. 63-66 at 65 (1989).
Freed et al., "pH Control of Nucleophilic/electrophilic oxidation", International Journal of Pharmaceutics, vol. 357, pp. 180-188 (2008).
Giles R. et al. Plastic Packaging Materials, Chapter 81. pp. 1473-1477 in Remington's Pharmaceutical Sciences, 17th Ed, 1985.
Goodman and Gilman, "The Pharmacological Basis of Therapeutics, Seventh Edition", MacMillan Publishing Company, Table of Contents, 1985.
Goodman and Gilman, 1985, 7th edition, chapter 22, 491-530.
Goodman and Gilman, 1985, 7th edition, chapter 23, 533-579.
Graham N.B., Poly(Ethylene Glycol) Chemistry: Biotechnical and Biomedical Applications, p. 263-291 Chapter 17, 1992.
Griffin W, "Classification of Surface-Active Agents by HLB" Journal of the Society of Cosmetic Chemists, Atlas Powder Company, 1949, pp. 311-326.
Griffith, et al. "Tablet Crushing and the Law: The Implications for Nursing" Professional Nurse 19(1), pp. 41-42, 2003.
Gryczke et al, "Development and evaluation of orally disintegrating tablets (ODTs) containing Ibuprofen granules prepared by hot melt extrusion", Colloids and surfaces., B, Biointerfaces, Elsevier, Amsteram, NL, vol. 86, No. 2, Apr. 5, 2011, pp. 275-284.
Guidance for Industry—Bioavailability and Bioequivalence—Studies for Orally Administered Drug Products—General Considerations, FDA, BP, Announced in the Federal Register: vol. 68, No. 53/Mar. 19, 2003.
Guidance for Industry—Statistical Approaches to Establishing Bioequivalence, FDA, BP, Jan. 2001.
Handbook of Pharmaceutical Excipients, 1986, American Pharmaceutical Association, Washington, DC and London (Table of Content Only).
Handbuch der Kunststoff-Extrusionstechnik 1, "Grundlagen" in Chapter 1.2 Klassifizierung von Extrudern, pp. 3-7. 1989. (Full english translation attached).
Hanning C,D.et al. "The Morphone Hydrogel Suppository. A New Sustained release Rectal Preparation", British Journal of Anaesthesia, 61, pp. 221-227, 1988.
Hartauer, Kerry J. "Influence of Peroxide Impurities in Povidone and Crospovidone on the Stability of Raloxife" Pharma. Dev. & Tech, 5 (3) 303-310 (2000).
Henriest D. et al. In vitro and in vivo evaluation of starch-based hot stage extruded double matrix systems. Journal of Controlled Release, 2001, vol. 75, pp. 391-400.
Hoepfner et al. Fiedler Encyclopedia of Excipients. Sixth Edition, 2007, Aulendorf, Germany: Table of Contents only.
Hong S. et al. Dissolution kinetics and physical characterization of three-layered tablet with poly(ethylene oxide) core matrix capped by Carbopol. Int .J. Pharmacol. 2008, vol. 356, pp. 121-129.
Inert gas—Wikipedia, Dec. 2009, pp. 1-3.
Investigation of a Directly Compressible Metformin HCl 500mg Extended Release Formulation Based on Hypromellose, Colorcon Jul. 2009.

(56) References Cited

OTHER PUBLICATIONS

Quintavalle et al., "Preparation of sustained release co-extrudates by hot-melt extrusion and mathematical modelling of in vitro/in vivo drug release profiles," European Journal of Pharmaceutical Sciences 33 (2008), 282-293.
Radko S.et al., Applied ad Theoretical Electrophoresis 5, pp. 79-88, 1995.
Ravin, L. Preformulation. Chapter 76, pp. 1409-1423, In Remington's Pharmaceutical Sciences, 17th Ed, 1985.
Remington, The Science and Practice of Pharmacy, 19th ed., vol. II, p. 1457 (1995) (providing a table of DFA-approved commercially marketed salts).
Repka M et al., Bioadhesive Properties of Hydroxypropylcellulose Topical Films Produced by Hot-Melt Extrusion, Journal of Controlled Release, 70 (2001), pp. 341-351.
Repka MA, Drug Dev Ind Pharm. Oct. 2007; 33(10):1043. (Abstract).
Riippi M. et al., The effect of compression force on surface structure, crushing strength, friability and disintegration time of erythromycin acistrate tablets, Eur J Pharm Biopharm, vol. 46, 1998, pp. 339-345.
Rippie E.G. et al, "Regulation of Dissolution Rate by Pellet Geometry" Journal of Pharmaceutical Sciences, vol. 58, No. 4, pp. 428-431, Apr. 1969.
Rippe, E. Powders. Chapter 89, pp. 1585-1602, In Remington's Pharmaceutical Sciences, 17th Ed, 1985.
Ritschel et al. Die Tablette: Handbuch der Entwicklung, Herstellung und Qualitatssicherung, 2nd Edition, 2002, Ch 6, pp. 515-519. (Full English translation attached).
Ritschel et al. Die Tablette: Handbuch der Entwicklung, Herstellung und Qualitatssicherung, 2nd Edition 2002, Ch 6, pp. 69-82 and 115-136.
Ritschel et al. Die Tablette: Handbuch der Entwicklung, Herstellung und Qualitatssicherung 2nd Edition, 2002, Table of content.
Rosiaux et al. "Ethanol-resistant ethylcellulose/guar gum coatings—Importance for formulation parameters" European Journal of Pharmaceutics and Biohamarceutics, vol. 85, No. 3, (Jul. 25, 2013), pp. 1250-1258.
Rowe C et al. Handbook of Pharmaceutical Excipients. Sixth Edition. 2009, Edition Cantor Verlag Aulendorf, pp. V-IX, Table of Contents.
Rowe C et al., Handbook of Pharmaceutical Excipients, 7th Edition, 2012, Table of Contents.
Salomies et al., "Determination of Oxycodone Hydrochloride in Oral Solutions by High-Performance Thin-Layer Chromatography/ Densitometry," Journal of AOAC International, 83: 1497-1501 (2000).
Sax et al., Hawley's Condensed Chemical Dictionary, 11th ed., 1987, p. 1233, definition of "wax".
Scheirs J., et al, "Characterizing the Solid-State Thermal Oxidation of Poly (ethylene oxide) Powder", pp. 2014-2019, Polymer, vol. 32, No. 11, 1991.
Schier et al. "Fatality from Administration of Labetalol and Crushed Extended Release Nifedipine" The Annals of Pharmacotherapy vol. 37, 1420-1423, Oct. 2003.
Schroeder J., et al. Granulierung hydrophober Wirkstoffe im Planetwalzenextruder, Pharm. Ind. 2003, vol. 65, No. 4, 367-372. (Full English translation attached).
Sciarra et al. Aerosols. Chapter 93., pp. 1662-1677, In Remington's Pharmaceutical Sciences, 17th Ed, 1985.
Search result conducted on http://www.unitconversion.org/force/ newtons-to-kiloponds-convresion.html, on Jul. 5, 2011 (Conversion of 18.8 kiloponds to newtons).
Shivanand P et al., "Factors Affecting Release of KCI From Melt extruded Polyethylene Disks", Pharmaceutical Research, Oct. 1991, vol. 8, No. 10, p. S-192.
Siegel, P. Tonicity, Osmoticity, Osmolality, and Osmolarity. Chapter 80. pp. 1454-1472 In Remington's Pharmaceutical Sciences, 17th Ed. 1985.
Silver, J. "Painkiller OxyContin" most commonly abused prescription drug on the streets of Western Pennsylvania, Pittsburg Post-Gazette, Apr. 8, 2001.
Spassov et al., Stereochemistry of Diastereomeric 3-Dialkylaminopropanols and O-Derivatices, J.f. prakt. Chemie, 323:5, 793-800 (1981).
Sprockel O.L et al. "Permeability of Cellulose Polymers: Water Vapour Transmission Rates"., J. Pharma. Pharmacol. 42, pp. 152-157, 1990.
Sreenivasa, B. et al, Design and Evaluation of Ethylene Vinyl Acetate Sintered Matrix Tablets, Indian Journal of Pharmaceutical Science, Sep.-Oct. 2003, 65(5): 496-502.
Stafford J., überzogene feste Formen, 1991, 347-68. (English translation attached).
Strang, Abuse of buprenorphie (Temgesic) by snorting, Letter to the editor, British Med. J., 302: 969 (1991).
Stringer J.L., et al "Diffusion of small molecular weight drugs in radiation-crosslinked poly(ethylene oxide) hydrogels", Journal of Controlled Release 42, pp. 195-202, 1996.
Summers et al; "Influence of Crystal Form on Tensile Strength of Compacts of Pharmaceutical Materials" Journal of Pharmaceutical Sciences, vol. 66, No. 8, Aug. 1977, pp. 1172-1175.
Swarbrick, Encyclopedia of Pharmaceutical Technology, Informa Healthcare, 1988, 1st edition, vol. 1, table of contents.
Swarbrick, Encyclopedia of Pharmaceutical Technology, Informa Healthcare, 1088, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Svvarbrick, Encyclopedia of Pharmaceutical Technology, Informa Healthcare 1988, 1st edition, vol. 19, table of contents.
Swarbrick, Encyclopedia of Pharmaceutical Technology, Informa Healthcare, 1988, 1st edition, vol. 2, table of contents.
Swarbrick, Encyclopedia of Pharmaceutical Technology, Informa Healthcare, 1988, 1st edition, vol. 20, table of contents.
Swarbrick, Encyclopedia of Pharmaceutical Technology, Informa Healthcare, 1988, 1st edition, vol. 3, table of contents.
Mullins, John. Ophthalmic Preparations. Chapter 87, pp. 1553-1563; In Remington's Pharmaceutical Sciences, 17th Ed, 1985.
Munjal M. et al., "Polymeric Systems for Amorphous Delta9—Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munsell Book of Color: Glossy Collection", X-Rite, Originally published in 1966, pp. 1-7.
Nairn, J.G., Solutions, Emulsion, Suspensions and Extractives. Chapter 84. pp. 1492-1517, In Remington's Pharmaceutical Sciences, 17th Ed, 1985.
Note for Guidance on Stability Testing, EMEA, Aug. 2003, pp. 1-20.
Note for Guidance on the Investigation of Bioavailability and Bioequivalence, EMEA, London, Jul. 26, 2001 (CPMP/EWP/QWP/ 1401/98).
Ohnishi N. et al., Effect of the Molecular Weight of Polyethylene Glycol on the Bioavailability of Indomethacin Sustained-Release suppositories Prepared with Solid Dispersion, Chem. Pharm. Bull, 35(8), pp. 3511-3515, 1987.
Oliveira et al., "Production and characterization of laminar coextrudates at room temperature in the absence of solvents," AAPS Annual Meeting and Exposition, Oct. 14-18, 2012, Chicago, USA.

(56) References Cited

OTHER PUBLICATIONS

Oxicotin: Balancing Risks and Benefits, United States Senate, Hearing, Feb. 12, 2002.
Oxycodon (Oxygesic): Missbrauch, Abhaengigkeit und toedliche Folgen durch Injection zerstossener Retardtabletten, Deutsches Ärzteblatt, vol. 36, A2326-A2326, Sep. 5, 2003.
Ozeki T. et al. "Control of Medicine Release From Solid Dispersion Through Poly(ethylene oxide)-Carboxyvinylpolymer Interaction", International Journal of Pharmaceutics, 165, 1998, pp. 239-244.
Ozeki T. et al. "Controlled Release From Solid Dispersion Composed of Poly(ethylene oxide)-Carbopol Interpolymer Complex With Various Cross-Linking Degrees of Carbopol", Journal of Controlled Release. 63, 2000. pp. 287-295.
Ozeki T. et al., "Control of medicine release from solid dispersion composed of the poly(ethylene oxide)-carboxyviylpolymer interpolymer complex by varying molecular wight of poly(ethylene oxide)"Journal of Controlled Release 58, pp. 87-95, 1999.
PCT International Search Report and Written Opinion for PCT Application No. PCT/EP2010/004459 dated Dec. 1, 2010.
PCT International Search Report and Written Opinion for PCT Application No. PCT/EP2013/059728 dated Aug. 6, 2013.
PCT International Search Report and Written Opinion for PCT Application No. PCT/EP2009/003290 dated Jul. 9, 2009.
PCT International Search Report and Written Opinion for PCT Application No. PCT/EP2013/053894 dated Mar. 22, 2013.
PCT International Search Report and Written Opinion for PCT Application No. PCT/EP2013/057851 dated Jun. 12, 2013.
PCT International Search Report and Written Opinion for PCT Application No. PCT/EP2014/064830 dated Aug. 6, 2014.
PCT International Search Report and Written Opinion for PCT Application No. PCT/EP2014/075618 dated Feb. 11, 2015.
PCT International Search Report and Written Opinion for PCT Application No. PCT/EP2014/0777748 dated Feb. 12, 2015.
PCT Second Written Opinion for PCT Application No. PCT/EP2013/053893 dated Feb. 21, 2014.
PCT Second Written Opinion for PCT Application No. PCT/EP2013/057851 dated Apr. 15, 2014.
Pentoxifylline 400 mg Extended Release Tablets, Lubrizol Advanced Materials, Inc., Mar. 3, 2011, Previous Edition Nov. 19, 2009.
Perez-Marcos, B., Usefulness of certain varieties of Carbomer in the formulation of hydrophilic furosemide matrices, International Journal of Pharmaceutics, 67 (1991) 113-121.
Pharm. Research, Official Journal of the American Association of Pharmaceutical Scientists, Sep. 1989, 6(9), S-98.
Pharm. Research, Official Journal of the American Association of Pharmaceutical Scientists, Oct. 1991, 8(10), S-192.
Phillips, G. Briggs. Sterilization. Chapter 79. pp. 1443-1454, In Remington's Pharmaceutical Sciences, 17th Ed, 1985.
Physico-mechanical Characterization of Polyox for Table Manufacture, Colorcon Jul. 2009.
Pillay V. et al. A novel approach for constant rate delivery of highly soluble bioactives from a simple monolithic system. Journal of Controlled Release. 2000, vol. 67, pp. 67-78.
Pinto, Joao F. et al.,"Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).
Piringer, O.G.and A.L. Baner, Plastic Packaging: Interactions with Food and Pharmaceuticals, Wiley VCH, 2nd Completely Revised Edition, Feb. 13, 2008, (Table of Contents only).
Polyox water soluble resins 2003. http://www.dow.com/webapps/lit/litorder.asp?filepath=polyox/pdfs/noreg/326-00002.pdf.
Polyox water-soluble resins (DOW Mar. 2002); see http://msdssearch.dow.com/PublishedLiteratureDOWCOM/dh_0031/0901b80380031a4a.pdf?filepath=326-00001.pdf&fromPage=GetDoc).
Polyox WSR-303, retrieved Mar. 10, 2014 from URL http://www.dow.com/dowwolff/en/industrial_solutions/polymers/polyethylene.
Polyox, Colorcon, Application Data (Apr. 2009) downloaded from http://www.colorcon.com/literature/marketing/mr/Extended%20Release/POLYOX/English/ads_PEO_Antioxidant.pdf.
Pontier, C. et al, "Use of cycles of compression to characterize the behavior of apatitic phosphate powders," Journal of the European Ceramic Society 22 (2002), 1205-1216.
Porter, S. Coating of Pharmaceutical Dosage Forms. Chapter 91. pp. 1633-1643 In Remington's Pharmaceutical Sciences, 17th Ed. 1985.
Prapaitrakul W. et al, "Release of Chlorpheniramine Maleate from Fatty Acid Ester Matrix disks Prepared by Melt-extrusion" J. Pharm. Pharmacol. 43, pp. 377-381, 1991.
Proeschel, P.A. et al., "Task-dependence of activity / bite-force Relations and its impact on estimation of chewing force from EMG"; J. Dent. Res., vol. 81, No. 7, pp. 464-468, 2002.
Purdue News, "Purdue Pharma Provides Update on Development of New Abuse-Resistant Pain Medications; FDA Cites Patient Needs As First Priority; New Drug Application Delayed," www.headaches.about.com, Jun. 18, 2002, pp. 1-6.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.
Tablet, www.docstoc.com (2011).
Third Party Observations filed with EPO for Patent EP658055B1, Feb. 2, 2009, pp. 1-8.
Thoma V.K. et al. "Bestimmung der In-vitro-Freigabe von schwach basischen Wirkstoffen aus Ratardarzneiformen", pp. 299-301, Pharm. Ind. 51, Nr, 3, 1989.
Tikhonov, A. et al, Biopharmacy. The Manual for Students of Pharmaceutical Universities and Departments, 2003, pp. 40-41, Kharkov, Ukraine (Full English translation attached).
Tipler, et al, Physics for Scientists and Engineers, vol. I, 6th Edition, pp. 234-235, 2003.
Tompkins et al., "Human abuse liability assessment of oxycodone combined with ultra-low-dose natrexone," Psychopharma., 210: 471-480 (2010).
Tramadol Hydrochloride 100 mg Extended Release Tablets, Lubrizol Advanced Materials, Inc., Sep. 2010.
Tranquilan-Aranilla et al., "Kappa-carrageenan-polyethylene oxide hydrogel blends prepared by gamma irradiation," Radiation Physics and Chemistry vol. 55, pp. 127-131, 1999.
Turco et al. Intravenous Admixtures. Chapter 86. pp. 1542-1552, In Remington's Pharmaceutical Sciences, 17th Ed. 1985.
US Pharmacopoeia, Chapter 1217, Aug. 12, 2008.
Varma et al, Factors Affecting Mechanism and Kinetics of Drug Release from Matrix-Based Oral Controlled Drug Delivery Systems, Am. J. Drug Deliv. 2004: 2 (1): 43-57.
Vippagunta et al. Crystalline Solids, Advanced Drug Delivery Review 48 (2001), 3-26.
Wade and Weller, "Handbook of Pharmaceutical Excipients: 2nd Edition", The American Pharmaceutical Association and the Pharmaceutical Press, Washington and London, Table of Contents pp. v-vi, 1994.
Wagner, Pharmazeutische Biologie—Drogen und ihre Inhaltsstoffe—Scharfstoffdrogen, 2nd., revised edition, Gustav Fischer Verlag, Stuttgart—N.Y., 1982, pp. 82-92 (Full English Translation attached).
Wagner, Pharmazeutische Biologie—Drogen und ihre Inhaltsstoffe—Scharfstoffdrogen, 2nd., revised edition Gustav Fischer Verlag, Stuttgart—N.Y., 1982,Table of Content.
Waltimo, et al, "A novel force recorder and maximal isometric bite force values for healthy young adults", Scandinavian Journal of Dental Research 1993; 101: 171-175.
Waltimo, et al, "Maximal bite force and its association with signs and symptoms of craniomandibular disorders in young Finnish non-patients", ACTA Odontol Scand 53 (1995): 254-258.
Waterman et al., "Stabilization of Pharmaceuticals to Oxidative Degradation", Pharmaceutical Development and Technology, vol. 7(1), pp. 1-32, (2002).

(56) References Cited

OTHER PUBLICATIONS

Waters et al., "Intravenous Ouetiapine-Cocaine Use ("Q-Ball")", Letter to the Editor, Am. J. Psychiatry, 164(1): pp. 173-174 (2007).
Weiss, U., "Derivatives of Morphine. I 14-Dihydroxydihydromorphinone," J. Am. Chem. Soc. 77, pp. 5891-5892, Nov. 20, 1955.
Wikipedia—Dextromethorphan Aug. 12, 2013 (and attached related English-language entry dated Dec. 11, 2013).
Woodburn, K.R. et al., Vascular complications of injecting drug misuse, Br. J. of Surgery, vol. 83, 1996, pp. 1329-1334.
Wu N, et al. Mathematical modeling and in vitro study of controlled drug release via a highly swellable and dissolvable polymer matrix: polyethylene oxide with high molecular weights, J Control Release. Feb. 16, 2005;102(3):569-581.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.
Yang, et al; "Characterization of Compressibility and Compactibility of Poly(ethylene oxide) Polymers for Modified Release Application by Compaction Simulator"; Journal of Pharmaceutical Sciences, vol. 85, No. 10, pp. 1085-1090, Oct. 1996.
Yarbrough et al, Letters to Nature "Extraordinary effects of mortar- and -pestle grinding on microstructure of sintered alumina gel", Nature 322, pp. 347-349 (Abstract only) (Jul. 24, 1986).
Yeh et al., Stability of Morphine in Aqueous Solution III: Kinetics of Morphine Degradation in Aqueous Solution, Wiley Subscription Services, Inc., Journal of Pharmaceutical Sciences, 50(1): 35-42 (1961).
Zeeshan, F and N. Bukhari, "Development and Evaluation of a Novel Modified-Release Pellet-Based Tablet System for the Delivery of Loratadine and Pseudophedrine Hydrochloride as Model Drugs." AAPS PharmaSciTech 11(2):910-916 (available on-line May 22, 2010).
Zhang et al., "Properties of Sustained-Release Tablets Prepared by Hot-Melt Extrustion" Pharmaceutical Development and Technology, 1999, 4(2), 241-250.
Cuesov, 1999, pp. 351-352.
Sidhu et al., "Watch for nonpsychotropics causing psychiatric side effects," Current Psychiatry, vol. 7, No. 4, 2008, 61-74.
Verhoeven et al., "Influence of polyethylene glycol/polyethylene oxide on the release characteristics of sustained-release ethylcellulose mini-matrices produced by hot-melt extrusion: in vitro and in vivo evaluations," European Journal of Pharmaceutics and Biopharmaceutics 72 (2009) 463-470.
Vynckier et al.,"Hot-melt co-extrusion for the production of fixed-dose combination products with a controlled release ethylcellulose matrix core," International Journal of Pharmaceutics 464 (2014), 65-74.
Chibuzor et al. "Formulation Development and Evaluation of Drug Release Kinetics from Colon-Targeted Ibuprofen Tablets Based on Eudragit RL 100-Chitosan Interpolyelectrolyte Complexes" Hindawi Publ. Corporation ISRN Pharmaceutics, vol. 2013, Article ID 838403.
Satish et al. "Formulation and Characterization of Matrix and Triple Layer Matrix Tablets for Controlled Delivery of Tramadol Hydrochloride," International Journal of Pharmaceutical Sciences; 5(4) (2013) 458-464.
Verhoeven, et al. "Xanthan gum to tailor drug release of sustained-release ethylcellulose mini-matrices prepared via hotmelt extrusion: in vitro and in vivo evaluation," European Journal of Pharmaceutics and Biopharmaceutics, 63 (2006) 320-330.
Alekseeva et al, Chemical-Pharmaceutical Journal, vol. 41, No. 9, 2007, 49-52. (English abstract included.).
Extended European Search Report and Opinion for Application No. EP 15184634.2-1455, Mar. 3, 2016.
Saleem et al. "Formulation and Evaluation of Tramadol hydrochloride Rectal Suppositories," Indian J. Pharm Sci. Sep.-Oct. 2008; 70(5), 640-644.

Borquist et al., "Simulation of the release from a multiparticulate system validated by single pellet and dose release experiements," J. Controlled Release, 97: 453-465 (2004).
The Merck Index, 14th Ed. (2006) No. 0006360 Nalefene.
The Merck Index, 14th Ed. (2006) No. 0006362 Naloxone.
The Merck Index, 14th Ed. (2006) No. 0006363 Naltrexone.
The Merck Index, 14th Ed. (2006) No. 0006959 Oxycodone.
Alekseeva et al, Chemical-Pharmaceutical Journal, vol. 41, No. 9, 2007, 49-52. (Full translation attached.).
Cuesov, Drug Production Technology, Khar'kov, 1999, pp. 351-352. (Full translation attached).
Efentakis et al, Effects of Excipients on Swellin and Drug Release from Compressed Matrices, in Drug Development and Industrial Pharmacy 23(1):107-112, Jan. 1997, Abstract.
Tennant, "Simultaneous Use of Stimulants and Opioids," 2011 [online] retrieved on Jul. 7, 2016 from: http://www.practicalpainmanagement.com/treatments/pharmacological/opioids/simultaneous-use-stimulants-opioids; 7 pages.
Cuesov, Drug Production Technology, Khar'kov, 1999, pp. 351-352.
Linz et al. "Cebranopadol: A Novel Potent Analgesic Nociception/Orphanin FQ Peptide and Opioid Receptor Agonist," J Pharmacol. Exp. Ther. 2014; 349: 535-548; available online Apr. 8, 2014.
Fathima, N. et al. "Drug-excipient interaction and its importance in dosage form development," Journal of Applied Pharmaceutical Science 01 (06); 2011, pp. 66-71.
Starch 1500, Partially Pregelatinized Maize Starch, technical data from Colorcon, Feb. 2016, 6 pages.
Remington, Chapter 45, pp. 996-1035.
Extended European Search Report for Application No. EP 16183922.0-1460, dated Oct. 31, 2016.
Meyer et al., "Awareness Topic: Mitigating the Risks of Ethanol Induced Dose Dumping from Oral Sustained/Controlled Release Dosage Forms," FDA ACPS Meeting, Oct. 2005, 1-4.
Schilling, et al., "Novel application of hot-melt extrusion for the preparation of monolithic matrices containing enteric-coated particles." International Journal of Pharmaceutics 400 (2010) 34-31.
Decision of the United States District Court for the Southern District of New York, in In re *Endo Pharmaceuticals Inc. and Grunenthal GmbH v. Amneal Pharmaceuticals, LLC et al.*, Findings of Fact and Conclusions of Law, District Judge Thomas P. Griesa, New York, New York, Jan. 14, 2015.
Decision of the United States District Court for the Southern District of New York, in In re *Oxycontin Antitrust Litigation, Purdue Pharma LP v. Teva Pharmaceuticals*, Findings of Fact and Conclusions of Law, District Judge Sidney H. Stein, New York, New York, Jan. 14, 2014.
U.S. Court of Appeals, Federal Circuit, *Purdue Pharma L.P. v. Epic Pharma, LLC*, 117 USPQ2d 1733 (Fed. Cir. 2016).
Al-Angari, A. et al. "The compaction properties of polyethylene glycols," J Pharm. Pharmacol. (1985) 37:151-153.
Al-Nasassrah et al. , "The effect of an increase in chain length on the mechanical properties of polyethylene glycols," European Journal of Pharmaceutics and Biopharmaceutics 46 (1998) 31-38.
Anderson, S.L. et al., "A Model for Antiplasticization in Polystyrene," Macromolecules 28:2944-54 (1995).
Rack, D.M.et al., "Ethylene Oxide Polymers", in Kirk-Othmer Encyclopedia of Chemical Technology. 2000, John Wiley & Sons, Inc., vol. 10, 673-696.
Bailey, F.E., et al., "High Molecular Weight Polymers of Ethylene Oxide" Solution Properties Industrial and Engineering Chemistry, 1958. 50(1): 8-11.
Balogh, E., "Tastes in and Tastes of Paprika," in Taste: Proceedings of the Oxford Symposium on Food and Cookery 28 (Tom Jaine Ed.) 1988, pp. 25-40.
Baumann, T., "Pain Management," Pharmacotherapy: A Pathophysiologic Approach (J.T. DiPiro et al. eds., McGraw-Hill 4th ed. 1999), Ch. 56, 1014-1026.
Baumrucker, S.J., "OxyContin, the Media, and Law Enforcement", American Journal of Hospice & Palliative Care, 18:3 (May/Jun. 2001), 154-156.

(56) References Cited

OTHER PUBLICATIONS

Choi, S., et al., "Development of a Directly Compressible Poly(Ethylene Oxide) Matrix for the Sustained-Release of Dihydrocodeine Bitartrate", Drug Development and Industrial Pharmacy, vol. 29, No. 10, pp. 1045-1052, 2003.
Choi, S., et al., "Hydrophilic Matrix Formulations of Dihydrocodeine Bitartrate with Polyethylene Oxide by Direct Compression," Proceedings of the $29^{th}$ Annual Meeting of the Controlled Release Society, in collaboration with the Korea Society for Biomaterials, Minneapolis, $1^{st}$ Edition, 2002, 984-985.
Ciccone, P. E., "Attempted Abuse of Concerta," Letters to the Editor, J. Am. Acad. Child Adolesc. Psychiatry, 41:7 (Jul. 2002).
Controversies in ADHD: A Breakfast Symposium—Concerto.
Crowley, M. et al., Pharmaceutical Applications of Hot-Melt Extrusion: Part I. Drug Dev. & Indus. Pharmacy (2007) 33:909-926.
Crowley, M. et al., "Properties of Hot-Melt Extruded CPM Tablets Using Hydrophilic Polymers," poster presentation, (2000).
Crowley, M., "Physicochemical and Mechanical Characterization of Hot-Melt Extruded Dosage Forms." Dissertation presented to the Faculty of the Graduate School of the University of Texas at Austin. (May 2003).
Crowley, M., et al., "Evaluation of a Hot Melt Extrusion Technique using a Hydrophilic Thermal Polymer and Retardant for the Preparation of Extended Release Chlorpheniramine Maleate Tablets," in American Association of Pharmaceutical Scientists: Indianapolis, IN (2000).
Crowley0000001—Crowley0000127.
Davies, N. "Sustained Release and Enteric Coated NSAIDs: Are They Really GI Safe?" J. Pharm. & Pharmaceut. Sci., 2(1):5-14, 1999.
Declaration of Dr. James W. McGinity, dated Oct. 28, 2009; online, retrieved from: http://www.accessdata.fda.gov/dmgsatfda_docs/labeV2013/021121s032lbl.pdf.
Dimitrov, M, et al., "Study of Verapamil hydrochloride release from compressed hydrophilic Polyox-Wsr tablets." Int'l J Pharmaceutics (1999) 189:105-111.
Dittmer, D.K., et al., "Glue-Sniffing Neuropathies," Canadian Family Physician 39:1965-1971 (1993).
Donnelly, C.L., "ADHD Medications: Past and Future," Behavioral Health Management, May/Jun. 2002, 28 & 30.
Dow, "Material Safety Data Sheet: Polyox(TM) WSR 30" (effective date: Sep. 18, 2001).
Dow, "Polyox Water-Soluble Resins: Degradation of Water-Soluble Resins," Technical Data (Oct. 2002).
Drug Bank "Oxymorphone," 2015; online, available at: www.dmgbank.ca/chugs/db01192 printed Jul. 1, 2015.
*Endo Pharmaceuticals Inc.* v. *Teva Pharmaceuticals USA, Inc.* (S.D.N.Y 2015)—Redacted Version.
FDA News Release, "FDA approves abuse-deterrent labeling for reformulated OxyContin," Apr. 16, 2013, available at http://www.fda.gov/NewsEvents/Newsroom/Press.Announcements/ucm348252.htm.
FDA, "Notice of Determination that OxyContin Drug Products Covered by NDA 20-553 Were Withdrawn From Sale for Reasons of Safety or Effectiveness." Federal Register, vol. 78, No. 75, Apr. 18, 2013, 23273-23274.
Final Draft Labeling for Concerta Extended-Release Tablets Attachment to Approval Letter (2000); available at: http://www.accessdata.fda.gov/drugsatfda_docs/label/2000/21121lbl.pdf.
Greenhill, L.L., et al., "Practice Parameter for the Use of Stimulant Medications in the Treatment of Children, Adolescents, and Adults," J. Am. Acad. Child Adolesc. Psychiatry, 41:2 Supplement, 26S-49S (Feb. 2002).
Griffith, D., "Potential new ADHD drug creating lots of big hopes," Sacramento Bee (California), Oct. 30, 2002.
Huang, H. et al., "Preparation of Controlled Release Oral Dosage Forms by Low Temperature Melt Extrusion," AAPS PharmSci. 2000 2(S1).
Jaffe, S.L., "Failed Attempts At Intranasal Abuse of Concerta," Letters to the Editor, J. Am. Acad. Child Adolesc. Psychiatry, 41:1 (Jan. 2002).
Jannsen Pharmaceuticals, Inc. Concerta Labeling Revisioins, Dec. 12, 2013; online, retrieved from: http://www.accessdata.fda.gov/dmgsatfda_docs/labeV2013/021121s032lbl.pdf.
Joint Claim Construction and Prehearing Statement, dated Jul. 11, 2014. *Janssen Pharmaceuticals, Inc. and Grünenthal Gmbh* v. *Actavis Elizabeth LLC and Alkem Laboratories Limited*, Civil Action No. 2:13-cv-04507 CCC-MF (D.N.J.), *Janssen Pharmaceuticals, Inc. and Grünenthal GMBH* v. *Roxane Laboratories, Inc.*, Civil Action No. 2:13-cv-06929 CCC-MF (D.N.J.), and *Janssen Pharmaceuticals, Inc. and Grünenthal GMBH* v. *Alkem Laboratories Limited*, Civil Action No. 2:13-cv-07803 CCC-MF (D.N.J.).
Kibbe, Coloring Agents, in Handbook of Pharmaceutical Excipients (3d ed. 2000).
Kidokoro, M. et al. ,"Properties of Tablets Containing Granulations of Ibuprofen and Acrylic Copolymers Prepared by Thermal Processes," Pharm Dev. and Tech. , 6:263- 275 (2001).
Kinjo, N. et al, "Antiplasticization in the Slightly Plasticized Poly(vinyl chloride)," Polymer Journal 4(2):143-153 (1973).
Larhib, H. et al., "Compressing polyethyelene glycols: the effect of compression pressure and speed," Int 'l J Pharmaceutics (1997) 147: 199-205.
Lieberman, H., et al., Pharmaceutical Dosage Forms: Tablets, vol. 2, Ch. 5: Granulation Technology and Tablet Characterization (1990), Table of contents and 245-348.
Lyons et al., "Twitch Interpolation in the Assessment of the Maximum Force-Generating Capacity of the Jaw-Closing Muscles in Man," Arch, Oral. Biol. 41:12, 1161-1168 (1996).
Makki, A, et. al., Eds., A Dictionary of American Idioms, 4th Ed. Barron's, New York (2004), 342-343.
Markovitz, H., et al. "Calculations of Entanglement Coupling Spacings in Linear Polymers." Journal of Physical Chemistry, 1962. 66(8): 1567-1568.
McCrum, N., et al., Principles of Polymer Engineering. 2nd ed., New York: Oxford University Press. 447(1997), Chapter 7, 296-351.
McGinity, J.W. et al., "Melt-Extruded Controlled-Release Dosage Forms" in Pharmaceutical Extrusion Technology, Ghebre-Sellassie, I. and Martin, C., Eds., Marcel Dekker, Inc., New York, 2003, Chaster 10, 183-208.
McQuay, H. et a. "Methods of Therapeutic Trials," Textbook of Pain 1125-1138 (P.D. Wall & R. Melzack eds., Elsevier 4th ed. 1999), Table of Contents and 1125-1138.
Miura et al., "Comparison of Maximum Bite Force and Dentate Status Between Healthy and Frail Elderly Persons," J. Oral Rehabilitation, vol. 28 (2001), pp. 592-595.
Miyagawa, Y. et al., "Controlled-release of diclofenac sodium from wax matrix granulate," Int 'l J. Pharmaceutics (1996) 138:215-224.
National Drug Intelligence Center Information Bulletin "OxyContin Diversion and Abuse" Jan. 2001.
Payne, H. et al., Denatonium Benzoate as a Bitter Aversive Additive in Ethylene Glycol and Methanol-Based Automotive Products, SAE Technical Paper 930589, Abstract (1993).
Pilpel, N., et al. "The effect of temperature on the tensile strength and disintegration of paracetamol and oxytetracylcine tablets," J Pharm Pharmac., 29:389-392 (1977).
Polyox Water-Soluble Resins NF in Pharmaceutical Applications, Dow Chemical Company, Aug. 2002.
Purdue Pharma LP Material Safety Data Sheet, OxyContin Tablets, 10 mg, 15 mg, 20 mg, 30 mg, 40 mg, 60 mg, Version 16—Sep. 10; available at www.purduephruma.com/msdss/oxycontin_msds.pdf.
Rauwendaal, Chris, PHD, Responsive Expert Report of Chris Rauwendaal, Ph.D. Regarding Expert Report of Michael M. Crowley, Ph.D., dated Jul. 17, 2015.
Repka, M. et al. Pharmaceutical Applications of Hot-Melt Extrusion: Part II. Drug Dev. & Indus. Pharmacy (2007) 33:1043-1057.
Saravanan, M. et al., "The Effect of Tablet Formulation and Hardness on in Vitro Release of Cephalexin from Eudragit L100 Based Extended Release Tablets," Biol. Pharm. Bull. (2002) 25(4):541-545.

(56) References Cited

OTHER PUBLICATIONS

Seitz, J.A.; et al., "Evaluation of the Physical Properties of Compressed Tablets 1: Tablet of Hardness and Friability," J. of Pharm. Sci. , 54:1353-1357 (1965).
Shah, et al., "Some Effects of Humidity and Heat on the Tableting Properties of Microcrystalline Cellulose Formulations 1," J. of Pharm. Sci., 57:181-182 (1967).
Singhal, et al., Handbook of Indices of Food Quality and Authenticity (1997), "Capsicum" p. 398-299.
Smith, K.L. et al. "High Molecular Weight Polymers of Ethylene Oxide—Plastic Properties." Industrial and Engineering Chemistry, 1958. 50(1): 12-16.
Tapentadol Pre-Review Report, Expert Committee on Drug Dependency Thirty-Fifth Meeting Hammamet, Tunisia, Jun. 4-8, 2012, available at http://www.who.int/medicines/areas/quality_safety/5.2Tapentadolpre-review.pdf.
Tiwari, D., et al., "Evaluation of polyoxyethylene homopolymers for buccal bioadhesive drug delivery device formulations." AAPS Pharmsci, 1999. 1(3): Article 13.
Wilkins, J.N., "Pharmacotherapy of Schizophrenia Patients with Comorbid Substance Abuse," Schizophrenia Bulletin, 23:215-228 (1997).
World Health Org., Cancer Pain Relief With a Guide to Opioid Availability (2d ed. 1996).
Yin, T.P., et al., "Viscoelastic Properties of Polyethylene Oxide in Rubber-Like State." Journal of Physical Chemistry, 1961. 65(3): 534-538.
Zacny, J. et al. Drug & Alcohol Dependence (2003) 69:215-232.
Zhang, F., "Hot-Melt Extrusion as a Novel Technology to Prepare Sustained-Release Dosage Forms," Dissertation University of Texas at Austin, Dec. 1999.
Baxter, J.L. et al., "Hydrodynamics-induced variability in the USP apparatus II dissolution test," International Journal of Pharmaceutics 292 (2005) 17-28.
Bellmann et al., "Development of an advanced in vitro model of the stomach and its evaluation versus human gastric psychology." Food Research International 88 (2016) 191-198.
Koziolek, M. et al., "Development of a bio-relevant dissolution test device simulating mechanical aspects present in the fed stomach," European Journal of Pharmaceutical Sciences 57 (2014) 250-256.
Remington, Chapter 45, pp. 996-1035. (Full Translation Attached).
Bingwen et al, 2008, p. 367. (full translation attached).
Extended European Search Report and Opinion for Application No. EP 15153679.4-1455, dated Jun. 30, 2015.
Monolithic: retrieved from internet: http:/merriam-webster.com/dictionary/monolithic, Retrieved on Sep. 2, 2015.
PCT International Search Report and Written Opinion for PCT Application No. PCT/EP2015/060377 dated Jul. 23, 2015.
PCT International Search Report and Written Opinion for PCT Application No. PCT/EP2015/061343 dated Jul. 21, 2015.
West, Anthony R., Solid state chemistry and its applications, Wiley, New York, 1988, pp. 358 and 365.
Dabbagh, et al "Release of Propranolol Hydrochloride from Matrix Tablets Containing Sodium Carboxymethylcellulose and Hydroxypropylmethylcellulose"; 1999; Pharmaceutical Development and Technology, 4(3), 313-324.
USP Expert Council, US Pharmacopoeia, Chapter 1092, 2007, 1-15.
Remington, Chapter 45, pp. 996-1035. (2000) (Full Translation Attached).
M. Xu et al., "Evaluation of the coat quality of sustained release pellets by individual pellet dissolution methodology," Int. J. Pharm. 478 (2015) 318-327.
Bannwarth, Bernard, "Will Abuse-Deterrent Formulations of Opioid Analgesics be Successful in Achieving Their Purpose?", Drugs, 2012, vol. 72, pp. 1713-1723.
COMPAP 90 technical data sheet Mar. 2014; 1 page.
Extended European Search Report for Application No. EP 16182124.4-1455, dated Jan. 17, 2017.

Furu et al. "use of ADHD drugs in the Nordic countries: a population-based comparison study," Acta Psychiatrica Scandinavia, May 2010.
Nickerson, B., Sample Preparation of Pharmaceutical Dosage Forms, Springer New York (2011); Chapter 1, pp. 3-48.
PCT International Search Report and Written Opinion for PCT Application No. PCT/EP2016/052046 dated Apr. 12, 2016.
PCT International Search Report and Written Opinion for PCT Application No. PCT/EP2017/070396 dated Sep. 8, 2017.
Polyox Water-Soluble Resins in Pharmaceutical Applications. Dow Chemicals. Published 2004.
U.S. Appl. No. 60/287,509, filed Dec. 2, 2002, Joshi et al.
U.S. Appl. No. 60/288,211, filed Sep. 2, 2004, Oshlack et al.
U.S. Appl. No. 60/310,514, filed Apr. 3, 2003, Oshlack et al.
U.S. Appl. No. 60/310,534, filed Apr. 10, 2003, Wright et al.
U.S. Appl. No. 60/376,470, filed Jan. 15, 2004, Ayer et al.
U.S. Appl. No. 60/384,442, filed Dec. 4, 2003, Fink et al.
European Pharmacopoeia 3.0, 2.9.8 "Resistance to Crushing of Tablets", 1997, p. 135.
Goodman and Gilman, 1985, 7th edition, chapter 29, 674-715.
King, Remington's Pharmaceutical Sciences 17th ed., Chapter 78, pp. 1418-1419 (1985).
Quadros, E. et al., "Evaluation of novel colonic delivery device in vivo," STP Pharma Sci. 5, 77-82 (1995).
Theeuwes, Felix et al., Osmotic Systems for Colon-Targeted Drug Delivery in Colonic Drug Absorption and Metabolism (Peter R. Bieck ed., 1993).
Wooten, Marvin R. et al., Intracerebral Hemorrhage and Vasculitis Related to Ephedrine Abuse; 13 Annals of Neurology 337 (1983).
De Brabander C., et al., "Development and evaluation of sustained release mini-matrices prepared via hot melt extrusion," Journal of Controlled Release 89 (2003), 235-247.
Pharma Tips ([online] retrieved on Mar. 22, 2018 from http://ww.pharmatips.in/Articles/Pharmaceutics/Tablet/Co-Processed-Directly-Compressed-Adjutants.aspx May 2011: 10 pages).
Patrick, K., et al., "Pharmacology of Methylphenidate, Amphetamine Enantiomers and Pemoline in Attention-Deficit Hyperactivity Disorder," Human Psychopharmacology, vol. 12, 527-546 (199).
"Low Substituted Hydroxypropyl Celluslose", Drugs.com, from https://www.drugs.com/inactive/low-susbstitute-hydroxypropyl-cellulose-581.html (2018).
Agarwal, G, et al, "Oral Sustained Release Tablets: An Overview with a Special Emphasis on Matrix Tablet," American Journal of Advanced Drug Delivery, 2017.
Brzeclo, W.,et al., "The Advent of a new Pseudoephedrine Product to Combat Methampetamine Abuse," Am J Drug Alcohol Abuse, 2013: 39(5): 284-290.
Extended European Search Report for Application No. 17173240.7 dated Nov. 28, 2017.
Jamini, M., et al, "Sustained Release Matrix Type Drug Delivery System: A Review," Journal of Drug Delivery & Therapeutics; 2012, 2(6), 142-148.
Kelly, C. et al, "Methamphetamine Synthesis Inhibition: Dissolving Metal Reductions," Johns Hopkins Univ. Applied Physics Lab., 2015, 1-10.
Misal, R, et al., "Matrix Tablet: A Promising Technique for Controlled Drug Delivery," Indo American Journal of Pharmaceutical Research, 2013.
Presley, B. et al., "Efficiency of Extraction and Conversion of Pseudoephedrine to Methamphetamine from Tamper-Resistant and Non-Tamper-Resistant Formulations," Journal of Pharmaceutical and Biomedical Analysis , 2018, 16-22.
Definition Granule, Merriam-Webster, accessed online Jun. 28, 2018 (2018).
Houston, T.E., et al., "Bite Force and Bite Pressure: Comparison of Humans and Dogs," http://www.glapbta.com/BFBP.pdf, 2003, pp. 1-7.
Sigma-Aldrich entry for CAS No. 9010-88-2; www.sigmaaldrich.com/catalog/product/aldrich/182249?lang=en&region=US (downloaded Jun. 2018).
Extended European Search Report and Opinion for Application No. EP 15165064.5-1455, dated Oct. 16, 2015.

(56) References Cited

OTHER PUBLICATIONS

Extended European Search Report and Opinion for Application No. EP 15165065.2-1455, dated Nov. 2, 2015.
Extended European Search Report and Opinion for Application No. EP 15165067.8-1455, dated Nov. 2, 2015.
Extended European Search Report and Opinion for Application No. EP 15165069.4-1455, dated Nov. 2, 2015.
Extended European Search Report and Opinion for Application No. EP 15165070.2-1455, dated Nov. 2, 2015.
Sprockel, et. al, "A melt-extrusion process for manufacturing matrix drug delivery systems," Int. Journal of Parmaceutics 155 (1997) 191-199.
Sumitomo Seika Chemicals, Co., Ltd, "Certificate of Analysis," Product: Polyethylene Oxide; Grade: PEO-18NF; Feb. 2, 2016.
Sumitomo Seika Chemicals, Co., Ltd. "Certificate of Analysis," Product: Polyethylene Oxide; Grade: PEO-20NF; Feb. 3, 2016.
Sumitomo Seika Checmicals, Co., Ltd, "Certificate of Analysis," Product: Polyethylene Oxide; Grade: PEO-20NF; Jan. 23, 2012.
Sumitomo Seika Chemicals, Co., Ltd., "Certificate of Analysis," Product: Polyethylene Oxide; Grade: PEO-20NF; May 15, 2013.
Patel, et al., "Poloxamers: A pharmaceuticals excipient with therapeutic behaviors," PharmTech, vol. 1, No. 2, pp. 299-300 (Apr. 2009).
Targin(R) Product Monograph. Purdue Pharma. Revised Mar. 1, 2016.
Turkington, R., "Amphetamines," in Chemicals used for Illegal Purposes. A Guide for first Responders to Identify Explosives, Recreational Drugs, and Poisons, 2010, p. 247.
Vezin, W. et al, "Adjustment of precompression force to reduce mixing-time dependence of tablet tensile strength," J. Pharm. Pharmacol. 1983, 35: 555-558 (Mar. 28, 1983).
Qi et al, "An Investigation into the Crystallisation Behavior of an Amorphous Cryomilled Pharmaceutical Material Above and Below the Glass Transition Temperature," Journal of Pharmaceutical Sciences, 2009, 196-208.
Patel, et. al., "Poloxamers: A pharmaceutical excipient with therapeutic behaviors," PharmTech, vol. 1, No. 2, pp. 299-300 (Apr. 2009).
Weinhold, et al. "Buprenorphine alnoe and in combination with naloxone in non-dependent humans." Drug & Alcohol Dependence 30.3 (1992): 263-274.
Befort et al., "The Conserved Asparatate Residue in the Third Putative transmember Domain." Molecular Pharmacology 1996: 49:216-223 (1996).
BASF the chemical company, Kollicoat IR Technical information. Feb. 2013, p. 1-14 (2013).
Domino E.F. (1991) Nicotine: A Unique Psychoactive Drug, In: Adikofer F., Thurau K. (eds.) Effects of Nicotine on Biological Systems. APS Advances in Pharmacological Sciences. Birkhaeuser Basel (1991).
Fitzpatrick, J. "The influence of Superdisintegrants on Immediate Release," By Pharmaceutical Technology Editions [online] retrieved from http://www.pharmatech.com/influence-superdisintegrants-immediate-release; vol. 21, issue 6 (Jun. 1. 2011).
Kolar et al., "Treatmen of adults with attention-deficit/hyperactivity disorder," Neuropsychiatric Disease and Treatment 2008:4(3):389-403.
Rasmussen, N. "America's First Amphetamine Epidemic 1929-1971," American Journal of Public Health 2008:98(6): 974-985.
Suzuki, T, "Blood-brain barrier transport of opioid analgesics," Abstract, Yakugaki Zasshi; 131(10):1445-51 (2011).

* cited by examiner

TAMPER RESISTANT DOSAGE FORM COMPRISING INORGANIC SALT

This application is a continuation of U.S. application Ser. No. 13/781,957, filed Mar. 1, 2013, which is a continuation of International Patent Application No. PCT/EP2011/004406, filed Sep. 1, 2011, and claims priority of U.S. Provisional Patent Application No. 61/379,513, filed on Sep. 2, 2010, and European Patent Application No. 10009121.4, filed on Sep. 2, 2010, the entire contents of which patent applications are incorporated herein by reference.

The invention relates to a pharmaceutical dosage form exhibiting a breaking strength of at least 500 N, said dosage form containing a pharmacologically active ingredient (A); an inorganic salt (B); and a polyalkylene oxide (C) having a weight average molecular weight of at least 200,000 g/mol, wherein the content of the polyalkylene oxide (C) is at least 20 wt.-%, based on the total weight of the dosage form; wherein the pharmacologically active ingredient (A) is present in a controlled-release matrix comprising the inorganic salt (B) and the polyalkylene oxide (C) and wherein, under in vitro conditions, the release profile of the pharmacologically active ingredient (A) from said matrix comprises at least a time interval during which the release follows zero order kinetics.

Many pharmacologically active ingredients have a potential of being abused and thus, are advantageously provided in form of tamper resistant pharmaceutical dosage forms. Prominent examples of such pharmacologically active ingredients are opioids.

It is known that abusers crush conventional tablets, which contain opioids, to defeat the time-release "micro-encapsulation" and then ingest the resulting powder orally, intranasally, rectally, or by injection.

Various concepts for the avoidance of pharmacologically active ingredient abuse have been developed. One concept relies on the mechanical properties of the pharmaceutical dosage forms, particularly an increased breaking strength (resistance to crushing). The major advantage of such pharmaceutical dosage forms is that comminuting, particularly pulverization, by conventional means, such as grinding in a mortar or fracturing by means of a hammer, is impossible or at least substantially impeded.

Such pharmaceutical dosage forms are useful for avoiding pharmacologically active ingredient abuse of the pharmacologically active ingredient contained therein, as they may not be powdered by conventional means and thus, cannot be administered in powdered from, e.g. nasally. The mechanical properties, particularly the high breaking strength of these pharmaceutical dosage forms renders them tamper resistant. In the context of such tamper resistant pharmaceutical dosage forms it can be referred to, e.g., WO 2005/016313, WO 2005/016314, WO 2005/063214, WO 2005/102286, WO 2006/002883, WO 2006/002884, WO 2006/002886, WO 2006/082097, WO 2006/082099, WO 2008/107149, and WO 2009/092601.

The release kinetics of the pharmacologically active ingredients from such tamper resistant dosage forms is an important factor. It is well known that depending on how a pharmaceutically active ingredient is formulated into a tablet its release pattern can be modified.

On the one hand, formulations providing immediate release upon oral administration have the advantage that they lead to a fast release of the pharmacologically active ingredient in the gastrointestinal tract. As a result, a comparatively high dose of the pharmacologically active ingredient is quickly absorbed leading to high plasma levels within a short period of time and resulting in a rapid onset of medicinal action, i.e. medicinal action begins shortly after administration. At the same time, however, a rapid reduction in the medicinal action is observed, because metabolization and/or excretion of the pharmacologically active ingredient cause a decrease of plasma levels. For that reason, formulations providing immediate release of pharmacologically active ingredients typically need to be administered frequently, e.g. six times per day. This may cause comparatively high peak plasma pharmacologically active ingredient concentrations and high fluctuations between peak and trough plasma pharmacologically active ingredient concentrations which in turn may deteriorate tolerability.

Controlled release (e.g. delayed release, prolonged release, sustained release, and the like) may be based upon various concepts such as coating the pharmaceutical dosage form with a controlled release membrane, embedding the pharmacologically active ingredient in a matrix, binding the pharmacologically active ingredient to an ion-exchange resin, forming a complex of the pharmacologically active ingredient, and the like. In this context it can be referred to, e.g., W. A. Ritschel, Die Tablette, 2. Auflage, Editio Cantor Verlag Aulendorf, 2002.

In comparison to formulations providing immediate release, formulations providing prolonged release upon oral administration have the advantage that they need to be administered less frequently, typically once daily or twice daily. This can reduce peak plasma pharmacologically active ingredient concentrations and fluctuations between peak and trough plasma pharmacologically active ingredient concentrations which in turn may improve tolerability.

The ideal goal in designing a prolonged-release system is to deliver the pharmacologically active ingredient to the desired site at a rate according to the needs of the body. In the absence of feed-back control, one is left with a simple prolonging effect, where the pivotal question is at what rate a pharmacologically active ingredient should be delivered to maintain a constant blood pharmacologically active ingredient level. This constant rate should be the same as that achieved by continuous intravenous infusion where a pharmacologically active ingredient is provided to the patient at a constant rate just equal to its rate of elimination. This implies that the rate of delivery must be independent from the amount of pharmacologically active ingredient remaining in the dosage form and constant over time.

A perfectly invariant pharmacologically active ingredient blood or tissue level versus time profile is the ideal starting goal of a prolonged-release system. The way to achieve this, in the simplest case, is use of a maintenance dose that releases its pharmacologically active ingredient by zero-order kinetics.

U.S. Pat. No. 5,082,668 discloses an osmotically driven dosage form, namely a device comprising a wall that surrounds a compartment. The compartment comprises a beneficial agent composition and a push composition. A passageway in the wall connects the compartment with the exterior of the device for delivering the beneficial agent at a rate governed, in combination, by the wall, the beneficial agent composition and the push composition through the passageway of the device over time.

U.S. Pat. No. 7,300,668 relates to a dosage form comprising: a three-dimensionally printed innermost region comprising a first regional concentration of at least one active pharmaceutical ingredient; and plural three-dimensionally printed non-innermost regions in nested arrangement and comprising: a) one or more nested internal regions, wherein an internal region completely surrounds and is in contact with the innermost regions, and any other internal region present completely surrounds another internal region located to the interior thereof; and b) an outermost region completely surrounding an internal region, wherein the internal and outermost regions are in nested arrangement, wherein the at least one active pharmaceutical ingredient is released in approximately a zero-order release.

WO 2008/086804 discloses abuse resistant polyglycol-based pharmaceutical compositions. The composition contains one or more polyglycols and one or more active substances and it is resistant to crushing, melting and/or extraction. Moreover, such compositions have the same or lower solubility in ethanolic-aqueous medium, i.e. they are not subject to ethanol-induced dose dumping effect.

WO 2008/148798 discloses a layered pharmaceutical composition suitable for oral use in the treatment of diseases where absorption takes place over a large part of the gastrointestinal tract.

WO 03/024426 discloses a controlled release pharmaceutical composition for oral use comprising a solid dispersion of: i) at least one therapeutically, prophylactically and/or diagnostically active substance, which at least partially is in an amorphous form, ii) a pharmaceutically acceptable polymer that has plasticizing properties, and iii) optionally, a stabilizing agent, the at least one active substance having a limited water solubility, and the composition being designed to release the active substance with a substantially zero order release. Zero order release is provided by a coating that remains intact during the release phase and covers the matrix composition in such a manner that only a specific surface area is subject to erosion. Thereby the surface area from which the active substance is released is kept substantially constant during the time period.

WO 2010/057036 discloses a solid composition and methods for making and using the solid composition are provided. The solid composition comprises: (a) at least one active agent with a solubility of less than about 0.3 mg/ml in an aqueous solution with a pH of at most about 6.8 at a temperature of about 37° C.; and (b) a hydrophilic polymer matrix composition comprising: i) a hydrophilic polymer selected from the group consisting of METHOCEL®, POLYOX® WSR 1105 and combinations thereof; and optionally ii) a hydrophobic polymer selected from the group consisting of Ethocel 20 premium; and (c) an alkalizer selected from the group consisting of calcium carbonate, magnesium oxide heavy and sodium bicarbonate; wherein the composition provides at least about 70% release of the active between about 7 to about 12 hours following oral administration.

V. Pillay et al., Journal of Controlled Release, 67 (2000) 67-78 discloses an approach for constant rate delivery of highly soluble bioactives from a simple monolithic system prepared by direct compression at ambient conditions.

M. E. McNeill et al., J Biomater Sci Polym 1996, 7(11), 953-63 relates to properties controlling the diffusion and release of water-soluble solutes from poly(ethylene oxide) hydrogels. Part 4 deals with extended constant rate release from partly-coated spheres.

D. Henrist et al. relates to in vitro and in vivo evaluation of starch-based hot stage extruded double matrix systems. The objective of developing a double matrix system consisting of a hot stage extruded starch pipe surrounding a hot stage extruded and drug-containing starch core, was to obtain a monolithic matrix system applicable in the domain of sustained drug release. The behaviour of the systems was evaluated through dissolution testing and through a randomised crossover bioavailability study on nine male volunteers. All double matrix systems showed in vitro a nearly constant drug release profile after an initial slower release phase of 4 h. This initial slower release phase was avoided by loading the starch pipe with a small amount of drug.

L. Yang et al., J. Pharm. Sciences, 85(2), 1996, 170-173 relates to zero-order release kinetics from a self-correcting floatable asymmetric configuration drug delivery system.

It is an object of the invention to provide pharmaceutical dosage forms having advantages compared to pharmaceutical dosage forms of the prior art.

This object has been achieved by the subject-matter described hereinbelow.

It has been surprisingly found that comparatively low amounts of inorganic salts contained in a polymer matrix provide a further delay of the release of the pharmacologically active ingredients from tamper resistant dosage forms without leading to a substantial increase of the overall weight. Further, it has been surprisingly found that the incorporation of the inorganic salt into the polymer matrix does not substantially alter the mechanical properties of the tamper resistant dosage form which are based upon the polymer matrix, especially the breaking strength. Still further, it has been surprisingly found that the release profile follows zero order kinetics and does not depend upon the pH value of the release medium.

BRIEF DESCRIPTION OF THE DRAWINGS

The invention will now be described in greater detail with reference to the drawings, wherein.

Figure 1:
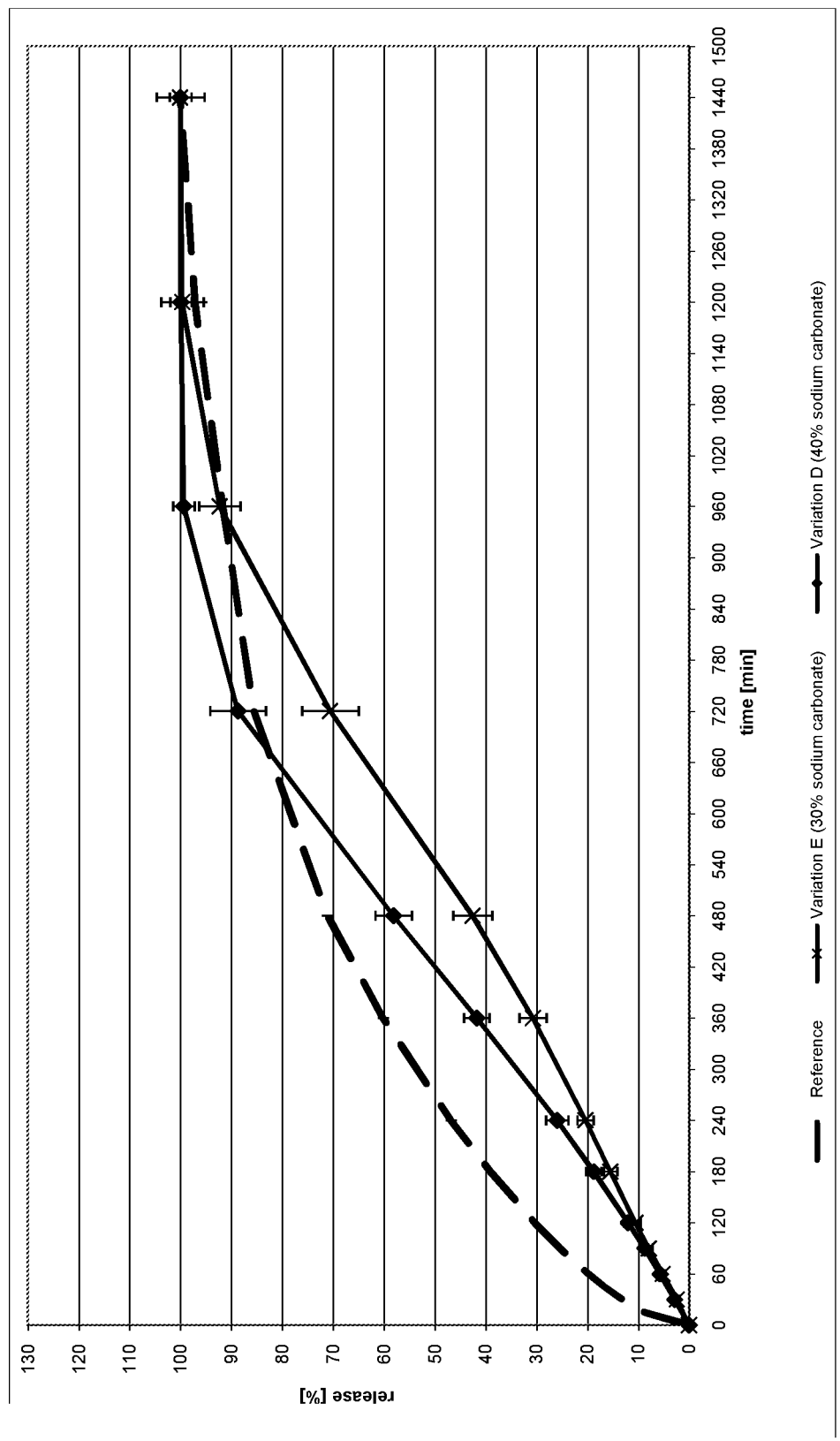
FIG. 1 shows the in vitro release profile of a pharmaceutical dosage form according to the invention containing 30 wt.-% (Variation E) and 40 wt.-% (Variation F), respectively, of sodium carbonate in comparison to the reference tablets.

A first aspect of the invention relates to a pharmaceutical dosage form exhibiting a breaking strength of at least 500 N, said dosage form containing
  a pharmacologically active ingredient (A);
  an inorganic salt (B); and
  a polyalkylene oxide (C) having a weight average molecular weight of at least 200,000 g/mol, wherein the content of the polyalkylene oxide (C) is at least 20 wt.-%, based on the total weight of the dosage form;
wherein the pharmacologically active ingredient (A) is present in a controlled-release matrix comprising the inorganic salt (B) and the polyalkylene oxide (C), and wherein, under in vitro conditions, the release profile of the pharmacologically active ingredient (A) from said matrix comprises at least a time interval during which the release follows zero order kinetics.

The dosage form according to the invention contains one or more pharmacologically active ingredients (A).

There are generally no limitations as to the pharmacologically active ingredient (A) (pharmacologically active compound) which can be incorporated into the tablet of the invention.

In a preferred embodiment, the pharmaceutical dosage form contains only a single pharmacologically active ingredient (A). In another preferred embodiment, the pharmaceutical dosage form contains a combination of two or more pharmacologically active ingredients (A).

Preferably, pharmacologically active ingredient (A) has potential for being abused. Active ingredients with potential for being abused are known to the person skilled in the art and comprise e.g. tranquilizers, stimulants, barbiturates, narcotics, opioids or opioid derivatives.

Preferably, the pharmacologically active ingredient (A) exhibits psychotropic action.

Preferably, the pharmacologically active ingredient (A) is selected from the group consisting of opiates, opioids, stimulants, tranquilizers, and other narcotics.

Particularly preferably, the pharmacologically active ingredient (A) is an opioid. According to the ATC index, opioids are divided into natural opium alkaloids, phenylpiperidine derivatives, diphenylpropylamine derivatives, benzomorphan derivatives, oripavine derivatives, morphinan derivatives and others.

The following opiates, opioids, tranquilizers or other narcotics are substances with a psychotropic action, i.e. have a potential of abuse, and hence are preferably contained in the pharmaceutical dosage form according to the invention: alfentanil, allobarbital, allylprodine, alphaprodine, alprazolam, amfepramone, amphetamine, amphetaminil, amobarbital, anileridine, apocodeine, axomadol, barbital, bemidone, benzylmorphine, bezitramide, bromazepam, brotizolam, buprenorphine, butobarbital, butorphanol, camazepam, carfentanil, cathine/D-norpseudoephedrine, chlordiazepoxide, clobazam clofedanol, clonazepam, clonitazene, clorazepate, clotiazepam, cloxazolam, cocaine, codeine, cyclobarbital, cyclorphan, cyprenorphine, delorazepam, desomorphine, dextromoramide, dextropropoxyphene, dezocine, diampromide, diamorphine, diazepam, dihydrocodeine, dihydromorphine, dihydromorphone, dimenoxadol, dimepheptanol, dimethylthiambutene, dioxaphetylbutyrate, dipipanone, dronabinol, eptazocine, estazolam, ethoheptazine, ethylmethylthiambutene, ethyl loflazepate, ethylmorphine, etonitazene, etorphine, faxeladol, fencamfamine, fenethylline, fenpipramide, fenproporex, fentanyl, fludiazepam, flunitrazepam, flurazepam, halazepam, haloxazolam, heroin, hydrocodone, hydromorphone, hydroxypethidine, isomethadone, hydroxymethylmorphinan, ketazolam, ketobemidone, levacetylmethadol (LAAM), levomethadone, levorphanol, levophenacylmorphane, levoxemacin, lisdexamfetamine dimesylate, lofentanil, loprazolam, lorazepam, lormetazepam, mazindol, medazepam, mefenorex, meperidine, meprobamate, metapon, meptazinol, metazocine, methylmorphine, metamphetamine, methadone, methaqualone, 3-methylfentanyl, 4-methylfentanyl, methylphenidate, methylphenobarbital, methyprylon, metopon, midazolam, modafinil, morphine, myrophine, nabilone, nalbuphene, nalorphine, narceine, nicomorphine, nimetazepam, nitrazepam, nordazepam, norlevorphanol, normethadone, normorphine, norpipanone, opium, oxazepam, oxazolam, oxycodone, oxymorphone, *Papaver somniferum*, papaveretum, pernoline, pentazocine, pentobarbital, pethidine, phenadoxone, phenomorphane, phenazocine, phenoperidine, piminodine, pholcodeine, phenmetrazine, phenobarbital, phentermine, pinazepam, pipradrol, piritramide, prazepam, profadol, proheptazine, promedol, properidine, propoxyphene, remifentanil, secbutabarbital, secobarbital, sufentanil, tapentadol, temazepam, tetrazepam, tilidine (cis and trans), tramadol, triazolam, vinylbital, N-(1-methyl-2-piperidinoethyl)-N-(2-pyridyl)propionamide, (1R,2R)-3-(3-dimethylamino-1-ethyl-2-methyl-propyl)phenol, (1R,2R,4S)-2-(dimethylamino)methyl-4-(p-fluorobenzyloxy)-1-(m-methoxyphenyl)cyclohexanol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethylamino-3(3-methoxyphenyl)-2-methyl-pentan-3-ol, (1RS,3RS,6RS)-6-dimethylaminomethyl-1-(3-methoxyphenyl)-cyclohexane-1,3-diol, preferably as racemate, 3-(2-dimethylaminomethyl-1-hydroxy-cyclohexyl)phenyl 2-(4-isobutyl-phenyl)propionate, 3-(2-dimethylaminomethyl-1-hydroxy-cyclohexyl)phenyl 2-(6-methoxy-naphthalen-2-yl)propionate, 3-(2-dimethylaminomethyl-cyclohex-1-enyl)-phenyl 2-(4-isobutyl-phenyl)propionate, 3-(2-dimethylaminomethyl-cyclohex-1-enyl)-phenyl 2-(6-methoxy-naphthalen-2-yl) propionate, (RR—SS)-2-acetoxy-4-trifluoromethyl-benzoic acid 3-(2-dimethylaminomethyl-1-hydroxy-cyclohexyl)-phenyl ester, (RR—SS)-2-hydroxy-4-trifluoromethyl-benzoic acid 3-(2-dimethylaminomethyl-1-hydroxy-cyclohexyl)-phenyl ester, (RR—SS)-4-chloro-2-hydroxybenzoic acid 3-(2-dimethylaminomethyl-1-hydroxy-cyclohexyl)-phenyl ester, (RR—SS)-2-hydroxy-4-methyl-benzoic acid 3-(2-dimethylaminomethyl-1-hydroxy-cyclohexyl)-phenyl ester, (RR—SS)-2-hydroxy-4-methoxy-benzoic acid 3-(2-dimethylaminomethyl-1-hydroxy-cyclohexyl)-phenyl ester, (RR—SS)-2-hydroxy-5-nitro-benzoic acid 3-(2-dimethylaminomethyl-1-hydroxy-cyclohexyl)-phenyl ester, (RR—SS)-2',4'-difluoro-3-hydroxy-biphenyl-4-carboxylic acid 3-(2-dimethylaminomethyl-1-hydroxy-cyclohexyl)-phenyl ester, and corresponding stereoisomeric compounds, in each case the corresponding derivatives thereof, physiologically acceptable enantiomers, stereoisomers, diastereomers and racemates and the physiologically acceptable derivatives thereof, e.g. ethers, esters or amides, and in each case the physiologically acceptable compounds thereof, in particular the acid or base addition salts thereof and solvates, e.g. hydrochlorides.

In a preferred embodiment the pharmaceutical dosage form according to the invention contains an opioid selected from the group consisting of DPI-125, M6G (CE-04-410), ADL5859, CR-665, NRP290 and sebacoyl dinalbuphine ester.

In a preferred embodiment, the pharmaceutical dosage form according to the invention contains one pharmacologically active ingredient (A) or more pharmacologically active ingredients (A) selected from the group consisting of oxymorphone, hydromorphone, morphine and the physiologically acceptable salts thereof.

In another preferred embodiment, the pharmacologically active ingredient (A) is selected from the group consisting of tapentadol, faxeladol, axomadol and the physiologically acceptable salts thereof.

In still another preferred embodiment, the pharmacologically active ingredient (A) is selected from the group consisting of 1,1-(3-dimethylamino-3-phenylpentamethylene)-6-fluoro-1,3,4,9-tetrahydropyrano[3,4-b]indole, particularly its hemicitrate; 1,1-[3-dimethylamino-3-(2-thienyl)-pentamethylene]-1,3,4,9-tetrahydropyrano[3,4-b]indole, particularly its citrate; and 1,1-[3-dimethylamino-3-(2-thienyl)pentamethylene]-1,3,4,9-tetrahydropyrano[3,4-b]-6-fluoroindole, particularly its hemicitrate. These compounds are known from, e.g., WO 2004/043967, WO 2005/066183.

The pharmacologically active ingredient (A) may be present in form of a physiologically acceptable salt, e.g. physiologically acceptable acid addition salt.

Physiologically acceptable acid addition salts comprise the acid addition salt forms which can conveniently be obtained by treating the base form of the active ingredient with appropriate organic and inorganic acids. Active ingredients containing an acidic proton may be converted into their non-toxic metal or amine addition salt forms by treatment with appropriate organic and inorganic bases. The term addition salt also comprises the hydrates and solvent addition forms which the active ingredients are able to form. Examples of such forms are e.g. hydrates, alcoholates and the like.

The pharmacologically active ingredient (A) is present in the dosage form in a therapeutically effective amount. The amount that constitutes a therapeutically effective amount varies according to the active ingredients being used, the condition being treated, the severity of said condition, the patient being treated, and whether the dosage form is designed for an immediate or retarded release. The amount of active ingredient(s) used in the present invention preferably ranges from about 0.01 wt.-% to about 95 wt.-%, more preferably from about 0.1 wt.-% to about 80 wt.-%, even more preferably from about 1.0 wt.-% to about 50 wt.-%, yet more preferably from about 1.5 wt.-% to about 30 wt.-%, and most preferably from about 2.0 wt.-% to 20 wt.-%, based on the total weight of the pharmaceutical dosage form.

The content of the pharmacologically active ingredient (A) in the pharmaceutical dosage form is not limited. The dose of the pharmacologically active ingredient (A) which is adapted for administration preferably is in the range of 0.1 mg to 500 mg, more preferably in the range of 1.0 mg to 400 mg, even more preferably in the range of 5.0 mg to 300 mg, and most preferably in the range of 10 mg to 250 mg. In a preferred embodiment, the total amount of the pharmacologically active ingredient (A) that is contained in the pharmaceutical dosage form is within the range of from 0.01 to 200 mg, more preferably 0.1 to 190 mg, still more preferably 1.0 to 180 mg, yet more preferably 1.5 to 160 mg, most preferably 2.0 to 100 mg and in particular 2.5 to 80 mg.

Preferably, the content of the pharmacologically active ingredient (A) is within the range of from 0.01 to 80 wt.-%, more preferably 0.1 to 50 wt.-%, still more preferably 1 to 25 wt.-%, based on the total weight of the pharmaceutical dosage form. In a preferred embodiment, the content of pharmacologically active ingredient (A) is within the range of from 7±6 wt.-%, more preferably 7±5 wt.-%, still more preferably 5±4 wt.-%, 7±4 wt.-% or 9±4 wt.-%, most preferably 5±3 wt.-%, 7±3 wt.-% or 9±3 wt.-%, and in particular 5±2 wt.-%, 7±2 wt.-% or 9±2 wt.-%, based on the total weight of the pharmaceutical dosage form. In another preferred embodiment, the content of pharmacologically active ingredient (A) is within the range of from 11±10 wt.-%, more preferably 11±9 wt.-%, still more preferably 9±6 wt.-%, 11±6 wt.-%, 13±6 wt.-% or 15±6 wt.-%, most preferably 11±4 wt.-%, 13±4 wt.-% or 15±4 wt.-%, and in particular 11±2 wt.-%, 13±2 wt.-% or 15±2 wt.-%, based on the total weight of the pharmaceutical dosage form. In a further preferred embodiment, the content of pharmacologically active ingredient (A) is within the range of from 20±6 wt.-%, more preferably 20±5 wt.-%, still more preferably 20±4 wt.-%, most preferably 20±3 wt.-%, and in particular 20±2 wt.-%, based on the total weight of the pharmaceutical dosage form.

In a preferred embodiment, the pharmacologically active ingredient (A) is contained in the pharmaceutical dosage form in an amount of 7.5±5 mg, 10±5 mg, 20±5 mg, 30±5 mg, 40±5 mg, 50±5 mg, 60±5 mg, 70±5 mg, 80±5 mg, 90±5 mg, 100±5 mg, 110±5 mg, 120±5 mg, 130±5, 140±5 mg, 150±5 mg, 160±5 mg, 170±5 mg, 180±5 mg, 190±5 mg, 200±5 mg, 210±5 mg, 220±5 mg, 230±5 mg, 240±5 mg, or 250±5 mg. In another preferred embodiment, the pharmacologically active ingredient (A) is contained in the pharmaceutical dosage form in an amount of 5±2.5 mg, 7.5±2.5 mg, 10±2.5 mg, 15±2.5 mg, 20±2.5 mg, 25±2.5 mg, 30±2.5 mg, 35±2.5 mg, 40±2.5 mg, 45±2.5 mg, 50±2.5 mg, 55±2.5 mg, 60±2.5 mg, 65±2.5 mg, 70±2.5 mg, 75±2.5 mg, 80±2.5 mg, 85±2.5 mg, 90±2.5 mg, 95±2.5 mg, 100±2.5 mg, 105±2.5 mg, 110±2.5 mg, 115±2.5 mg, 120±2.5 mg, 125±2.5 mg, 130±2.5 mg, 135±2.5 mg, 140±2.5 mg, 145±2.5 mg, 150±2.5 mg, 155±2.5 mg, 160±2.5 mg, 165±2.5 mg, 170±2.5 mg, 175±2.5 mg, 180±2.5 mg, 185±2.5 mg, 190±2.5 mg, 195±2.5 mg, 200±2.5 mg, 205±2.5 mg, 210±2.5 mg, 215±2.5 mg, 220±2.5 mg, 225±2.5 mg, 230±2.5 mg, 235±2.5 mg, 240±2.5 mg, 245±2.5 mg, or 250±2.5 mg.

Preferably, the pharmaceutically dosage form provides a release of the pharmacologically active ingredient (A) after 1 hour of preferably at most 60%, more preferably at most 40%, yet more preferably at most 30%, still more preferably at most 20% and most preferably at most 17%; after 2 hours preferably at most 80%, more preferably at most 60%, yet more preferably at most 50%, still more preferably at most 40% and most preferably at most 32%; after 3 hours preferably at most 85%, more preferably at most 65%, yet more preferably at most 55%, still more preferably at most 48% and most preferably at most 42%; after 4 hours preferably at most 90%, more preferably at most 75%, yet more preferably at most 65%, still more preferably at most 55% and most preferably at most 49%; after 7 hours preferably at most 95%, more preferably at most 85%, yet more preferably at most 80%, still more preferably at most 70% and most preferably at most 68%; after 10 hours preferably at most 99%, more preferably at most 90%, yet more preferably at most 88%, still more preferably at most 83% and most preferably at most 80%; and after 13 hours preferably at most 99%, more preferably at most 95%, yet more preferably at most 93%, still more preferably at most 91% and most preferably at most 89%.

In a particularly preferred embodiment, the pharmacologically active ingredient (A) is tapentadol, preferably its HCl salt, and the pharmaceutical dosage form is adapted for administration once daily or twice daily. In this embodiment, the pharmacologically active ingredient (A) is preferably contained in the pharmaceutical dosage form in an amount of from 25 to 250 mg.

In another particularly preferred embodiment, the pharmacologically active ingredient (A) is oxymorphone, preferably its HCl salt, and the pharmaceutical dosage form is adapted for administration twice daily. In this embodiment, the pharmacologically active ingredient (A) is preferably contained in the pharmaceutical dosage form in an amount of from 5 to 40 mg. In another particularly preferred embodiment, the pharmacologically active ingredient (A) is oxymorphone, preferably its HCl, and the pharmaceutical dosage form is adapted for administration once daily. In this embodiment, the pharmacologically active ingredient (A) is preferably contained in the pharmaceutical dosage form in an amount of from 10 to 80 mg.

In another particularly preferred embodiment, the pharmacologically active ingredient (A) is oxycodone, preferably its HCl salt, and the pharmaceutical dosage form is adapted for administration twice daily. In this embodiment, the pharmacologically active ingredient (A) is preferably contained in the pharmaceutical dosage form in an amount of from 5 to 80 mg. In another particularly preferred embodiment, the pharmacologically active ingredient (A) is oxycodone, preferably its HCl, and the pharmaceutical dosage form is adapted for administration once daily. In this embodiment, the pharmacologically active ingredient (A) is preferably contained in the pharmaceutical dosage form in an amount of from 10 to 320 mg.

In still another particularly preferred embodiment, the pharmacologically active ingredient (A) is hydromorphone, preferably its HCl, and the pharmaceutical dosage form is adapted for administration twice daily. In this embodiment, the pharmacologically active ingredient (A) is preferably contained in the pharmaceutical dosage form in an amount of from 2 to 52 mg. In another particularly preferred embodiment, the pharmacologically active ingredient (A) is hydromorphone, preferably its HCl, and the pharmaceutical dosage form is adapted for administration once daily. In this embodiment, the pharmacologically active ingredient (A) is preferably contained in the pharmaceutical dosage form in an amount of from 4 to 104 mg.

The pharmaceutical dosage form according to the invention is characterized by excellent durability of the pharmacologically active ingredient (A). Preferably, after storage for 4 weeks at 40° C. and 75% rel. humidity, the content of pharmacologically active ingredient (A) amounts to at least 98.0%, more preferably at least 98.5%, still more preferably at least 99.0%, yet more preferably at least 99.2%, most preferably at least 99.4% and in particular at least 99.6%, of its original content before storage. Suitable methods for measuring the content of the pharmacologically active ingredient (A) in the pharmaceutical dosage form are known to the skilled artisan. In this regard it is referred to the Eur. Ph. or the USP, especially to reversed phase HPLC analysis. Preferably, the pharmaceutical dosage form is stored in closed, preferably sealed containers, preferably as described in the experimental section, most preferably being equipped with an oxygen scavenger, in particular with an oxygen scavenger that is effective even at low relative humidity.

The dosage form according to the invention contains the pharmacologically active ingredient (A) in a controlled-release matrix comprising inorganic salt (B), wherein, under in vitro conditions, the release profile of the pharmacologically active ingredient (A) from said matrix comprises at least a time interval during which the release follows a zero order kinetics.

A skilled person knows which requirements need to be satisfied with in order to qualify the in vitro release profile of a pharmaceutical dosage form as being of zero order. Pharmacologically active ingredient dissolution from solid dosage forms has been described by kinetic models in which the dissolved amount of pharmacologically active ingredient (Q) is a function of the test time, t or Q=f(t). Some analytical definitions of the Q(t) function are commonly used, such as zero order, first order, Hixson-Crowell, Weibull, Higuchi, BakerLonsdale, Korsmeyer-Peppas and Hopfenberg models. Other release parameters, such as dissolution time (tx %), assay time (tx min), dissolution efficacy (ED), difference factor (f1), similarity factor (f2) and Rescigno index (xi1 and xi2) can be used to characterize pharmacologically active ingredient dissolution/release profiles.

For the purpose of specification the term "zero order kinetics" is preferably defined by the equation $W_0-W_t=K\,t$, where $W_0$ is the initial amount of pharmacologically active ingredient (A) in the pharmaceutical dosage form, $W_t$ is the amount of pharmacologically active ingredient (A) in the pharmaceutical dosage form at time t and K is a proportionality constant. Dividing this equation by $W_0$ and simplifying $f_t=K_0\,t$, where $f_t=1-(W_t/W_0)$ and $f_t$ represents the fraction of pharmacologically active ingredient (A) dissolved in time t and $K_0$ the apparent dissolution rate constant or zero order release constant. In this way, a graphic of the pharmacologically active ingredient-dissolved fraction versus time will be linear. This relation can be used to describe the dissolution of several types of modified release pharmaceutical dosage forms, as in the case of matrix tablets with low soluble pharmacologically active ingredients, coated forms, osmotic systems, etc. The pharmaceutical dosage forms following this profile release the same amount of pharmacologically active ingredient by unit of time and it is the ideal method of pharmacologically active ingredient release in order to achieve a pharmacological prolonged action. The following relation can, in a simple way, express this model: $Q_1=Q_0+K_0\,t$, where $Q_t$ is the amount of pharmacologically active ingredient dissolved in time t, $Q_0$ is the initial amount of pharmacologically active ingredient in the solution (most times, $Q_0=0$) and $K_0$ is the zero order release constant (cf. e.g., P. Costa et al., Eur J Pharm Sci. 2001, 13(2), 123-33).

It is evident to the skilled artisan that in praxis pharmaceutical dosage forms usually do not provide exact zero order release, particularly not over the full length of the release period, i.e. from the very beginning until the release of 100% of the pharmacologically active ingredient (A) that was originally contained in the pharmaceutical dosage form. Rather, in praxis in vitro release profiles can be described with a substantial degree of accuracy by these mathematical models, particularly when not considering the initial phase as well as the end phase of the release.

Preferably, the in vitro release profile of the pharmacologically active ingredient (A) from the pharmaceutical dosage form according to the invention comprises a time interval during which the release follows substantially a zero order kinetics, which time interval is preferably the time needed in order to release 50±5%, more preferably 50±10%, still more preferably 50±15%, yet more preferably 50±20%, even more preferably 50±25%, most preferably 50±30%, and in particular 50±35%, of the pharmacologically active ingredient (A). For example, the time needed in order to release 50±30% of the pharmacologically active ingredient (A) commences with the release of 20% (e.g. after 2.5 hours) and terminates with the release of 80% (e.g. after 10.5 hours) of the pharmacologically active ingredient (A). During such time interval, the in vitro release profile of the pharmacologically active ingredient (A) from the pharmaceutical dosage form follows substantially zero order kinetics, i.e. is substantially linear.

In a preferred embodiment, the kinetics for the in vitro release of the pharmacologically active ingredient (A) from the pharmaceutical dosage form is approximated by the equation $M_t/M_0=k\,t^n$ where t is time, $M_t$ is the amount of the pharmacologically active ingredient (A) which has been released at time t, $M_0$ is the total amount of the pharmacologically active ingredient (A) originally contained in the dosage form, i.e. before exposing the pharmaceutical dosage form to the release medium, k is a constant, and n is the release kinetics exponent. Preferably, the in vitro release profile of the pharmaceutical dosage form according to the invention provides a curve which defines the retarded release in percent to the time. For a defined time period, preferably from the beginning or from a point in time after the beginning, e.g. from the time where 20% have been released, to the time where 95% of the pharmacologically active ingredient (A) have been released from the dosage form according to the invention, the release profile is substantially linear.

Preferably, the time interval during which the release follows zero order kinetics, e.g. where the second derivative of the graph is substantially linear, is at least 20%, more preferably at least 30%, still more preferably at least 40%, yet more preferably at least 50%, even more preferably at least 60%, most preferably at least 70% and in particular at least 80% of the total release time needed for a release of 95 wt.-% of the pharmacologically active ingredient (A) that was originally contained in the pharmaceutical dosage form.

Preferably, the margins (limits) of "substantially linear" can be assessed based on the second derivative of the curve fitted to the measuring points. Ideally, said second derivative is zero. Preferably, however, a certain degree of deviation is also within the meaning of "substantially linear" according to the invention. Preferably, said deviations from the ideal linear behavior can be quantified by a Chi-square-test, which is known to a person skilled in the art. Preferably, the value determined according to the Chi-square-test is at most 2.5, more preferably at most 1.75, still more preferably at most 1.0, yet more preferably at most 0.75, even more preferably at most 0.5, most preferably at most 0.25, and in particular at most 0.1.

Preferably, the zero-order in vitro release kinetics can adequately be described by $M_t/M_\infty = k_0 \, t^n$, where $M_t$ and $M_\infty$ are the amounts of drug released at time t and the overall amount released, respectively, n is a release exponent indicative of profile shape, and $k_0$ is the zero-order release rate constant.

In a preferred embodiment, when fitting the relevant portion of the overall in vitro release profile that shows zero-order release kinetics to the equation $M_t/M_\infty = k_0 \, t$ (i.e. where n=1), the correlation coefficient of the fit is preferably at least 0.75, more preferably at least 0.80, still more preferably at least 0.85, yet more preferably at least 0.90, even more preferably at least 0.925, most preferably at least 0.95 and in particular at least 0.975.

In a preferred embodiment, the zero-order release rate constant $k_0$ is within the range of $0.030 \pm 0.028 \, h^{-1}$, more preferably $0.030 \pm 0.026 \, h^{-1}$, still more preferably $0.030 \pm 0.024 \, h^{-1}$, yet more preferably $0.030 \pm 0.020 \, h^{-1}$, even more preferably $0.030 \pm 0.015 \, h^{-1}$, most preferably $0.030 \pm 0.010 \, h^{-1}$, and in particular $0.030 \pm 0.005 \, h^{-1}$. In another preferred embodiment, the zero-order release rate constant $k_0$ is within the range of $0.040 \pm 0.035 \, h^{-1}$, more preferably $0.040 \pm 0.030 \, h^{-1}$, still more preferably $0.040 \pm 0.025 \, h^{-1}$, yet more preferably $0.040 \pm 0.020$ even more preferably $0.040 \pm 0.015 \, h^{-1}$, most preferably $0.040 \pm 0.010 \, h^{-1}$, and in particular $0.040 \pm 0.005 \, h^{-1}$. In still another preferred embodiment, the zero-order release rate constant $k_0$ is within the range of $0.050 \pm 0.035 \, h^{-1}$, more preferably $0.050 \pm 0.030 \, h^{-1}$, still more preferably $0.050 \pm 0.025 \, h^{-1}$, yet more preferably $0.050 \pm 0.020 \, h^{-1}$, even more preferably $0.050 \pm 0.015 \, h^{-1}$, most preferably $0.050 \pm 0.010 \, h^{-1}$, and in particular $0.050 \pm 0.005 \, h^{-1}$. In yet another preferred embodiment, the zero-order release rate constant $k_0$ is within the range of $0.060 \pm 0.035 \, h^{-1}$, more preferably $0.060 \pm 0.030 \, h^{-1}$, still more preferably $0.060 \pm 0.025 \, h^{-1}$, yet more preferably $0.060 \pm 0.020 \, h^{-1}$, even more preferably $0.060 \pm 0.015 \, h^{-1}$, most preferably $0.060 \pm 0.010 \, h^{-1}$, and in particular $0.060 \pm 0.005 \, h^{-1}$. In a further preferred embodiment, the zero-order release rate constant $k_0$ is within the range of $0.070 \pm 0.035 \, h^{-1}$, more preferably $0.070 \pm 0.030 \, h^{-1}$, still more preferably $0.070 \pm 0.025 \, h^{-1}$, yet more preferably $0.070 \pm 0.020$ even more preferably $0.070 \pm 0.015 \, h^{-1}$, most preferably $0.070 \pm 0.010 \, h^{-1}$, and in particular $0.070 \pm 0.005 \, h^{-1}$. In a still further preferred embodiment, the zero-order release rate constant $k_0$ is within the range of $0.080 \pm 0.035 \, h^{-1}$, more preferably $0.080 \pm 0.030 \, h^{-1}$, still more preferably $0.080 \pm 0.025 \, h^{-1}$, yet more preferably $0.080 \pm 0.020 \, h^{-1}$, even more preferably $0.080 \pm 0.015 \, h^{-1}$, most preferably $0.080 \pm 0.010 \, h^{-1}$, and in particular $0.080 \pm 0.005 \, h^{-1}$. In a yet further preferred embodiment, the zero-order release rate constant $k_0$ is within the range of $0.090 \pm 0.035 \, h^{-1}$, more preferably $0.090 \pm 0.030 \, h^{-1}$, still more preferably $0.090 \pm 0.025 \, h^{-1}$, yet more preferably $0.090 \pm 0.020 \, h^{-1}$, even more preferably $0.090 \pm 0.015 \, h^{-1}$, most preferably $0.090 \pm 0.010 \, h^{-1}$, and in particular $0.090 \pm 0.005 \, h^{-1}$. In another preferred embodiment, the zero-order release rate constant $k_0$ is within the range of $0.100 \pm 0.035 \, h^{-1}$, more preferably $0.100 \pm 0.030 \, h^{-1}$, still more preferably $0.100 \pm 0.025 \, h^{-1}$, yet more preferably $0.100 \pm 0.020$ even more preferably $0.100 \pm 0.015 \, h^{-1}$, most preferably $0.100 \pm 0.010 \, h^{-1}$, and in particular $0.100 \pm 0.005^{-1}$.

In a preferred embodiment, release exponent n is at least 0.65, more preferably at least 0.70, still more preferably at least 0.75, yet more preferably at least 0.80, even more preferably at least 0.85, most preferably at least 0.90 and in particular at least 0.95.

The zero-order release kinetics of the pharmaceutical dosage form according to the invention preferably does not rely on a coating that remains intact during the release phase and covers the matrix composition in such a manner that only a specific surface area is subject to erosion. Thus, the surface area of the pharmaceutical dosage form according to the invention from which the active substance is released is preferably not kept substantially constant by means of such a coating. On the contrary, the zero-order release kinetics of the pharmaceutical dosage form according to the invention is preferably based on the properties of the matrix in which the pharmacologically active ingredient (A) is embedded so that inert coatings can be completely omitted. Thus, while the pharmaceutical dosage form according to the invention may be coated with conventional coating materials such as polyvinyl alcohol, it is preferably not coated with inert coating materials that serve the purpose of permanently covering a substantial portion of the outer surface of the dosage form in order to allow drug release only through a predetermined, uncoated portion. Thus, in a preferred embodiment, the pharmaceutical dosage form according to the invention is uncoated, or it is coated with a coating material that substantially covers the complete outer surface of the dosage form, but does not leave a certain portion uncoated.

The pharmaceutical dosage form according to the invention comprises an inorganic salt (B).

In a preferred embodiment, the pharmaceutical dosage form comprises a single inorganic salt (B).

In another preferred embodiment, the pharmaceutical dosage form comprises a mixture of two or more inorganic salts (B). When the pharmaceutical dosage form according to the invention contains two different inorganic salts (B), e.g. pentasodium triphosphate and sodium carbonate, the relative weight ratio thereof is preferably within the range of from 8:1 to 1:8, more preferably 7:1 to 1:7, still more preferably 6:1 to 1:6, yet more preferably 5:1 to 1:5, even more preferably 4:1 to 1:4, most preferably 3:1 to 1:3, and in particular 2:1 to 1:2.

In another preferred embodiment, the pharmaceutical dosage form comprises a mixture of two inorganic salts (B). When the pharmaceutical dosage form according to the invention contains two different inorganic salts (B), e.g. pentasodium triphosphate and sodium carbonate, the storage stability at 5° C. and 25° C. is significantly increased. Concerning this matter the decrease of the content of Vitamin E contained in the pharmaceutical dosage form is more slowly in contrast to the pharmaceutical dosage form containing only one inorganic salt, e.g. sodium carbonate, and the release profile of the pharmacologically active ingredient (A) does not change in comparison to the release profile which is recorded before the storage stability was tested.

Preferably, inorganic salt (B) is salt, preferably an alkali metal or earth alkali metal salt, of a strong inorganic acid having a $pK_A$ value of at most 3, preferably at most 2, more preferably at most 1, still more preferably at most 0 and in particular at most −1. If said inorganic acid is a multi-protonic acid, preferably at least the first proton satisfies the above requirement.

Preferably, the inorganic salt (B) is a salt of carbonic acid ($H_2CO_3$), phosphoric acid ($H_3PO_4$), phosphorous acid ($H_3PO_3$), pyrophosphoric acid ($H_4P_2O_7$), or triphosphoric acid ($H_5P_3O_{10}$), preferably an alkali and/or earth alkali and/or hydrogenate salt thereof.

Preferably, the inorganic salt (B) is selected from the group consisting of alkali carbonates (e.g., $Na_2CO_3$, $K_2CO_3$, $NaKCO_3$), earth alkali carbonates (e.g., $MgCO_3$, $CaCO_3$), alkali hydrogen carbonates (e.g., $NaHCO_3$, $KHCO_3$), earth alkali hydrogen carbonates (e.g., $Mg(HCO_3)_2$, $Ca(HCO_3)_2$), alkali phosphates (e.g., $Na_3PO_4$, $Na_2KPO_4$, $NaK_2PO_4$, $K_3PO_4$), earth alkali phosphates (e.g., $Mg_3(PO_4)_2$, $Ca_3(PO_4)_2$), alkali pyrophosphates (e.g., $Na_4P_2O_7$, $Na_3KP_2O_7$, $Na_2K_2P_2O_7$, $NaK_3P_2O_7$, $K_4P_2O_7$) earth alkali pyrophosphates (e.g., $Mg_2P_2O_7$, $CaMgP_2O_7$, $Ca_2P_2O_7$), pentaalkali tri(poly)phosphates (alkali triphosphate tribasic) (e.g., $Na_5P_3O_{10}$, $Na_4KP_3O_{10}$, $Na_3K_2P_3O_{10}$, $Na_2K_3P_3O_{10}$, $NaK_4P_3O_{10}$, $K_5P_3O_{10}$, $Na_4KP_3O_{10}$), alkali hydrogen phosphates (e.g., $Na_2HPO_4$, $NaKHPO_4$, $K_2HPO_4$), earth alkali hydrogen phosphates (e.g., $MgHPO_4$, $CaHPO_4$), alkali dihydrogen phosphates (e.g., $NaH_2PO_4$, $KH_2PO_4$), earth alkali dihydrogen phosphates (e.g., $Mg(H_2PO_4)_2$, $Ca(H_2PO_4)_2$).

Preferably, the inorganic salt (B) is sodium carbonate or pentasodium triphosphate or mixtures thereof.

It has been surprisingly found that the inorganic salt (B) may further extend the release profile of the pharmaceutical dosage form compared to a comparative dosage form not containing inorganic salt (B).

In a preferred embodiment, the content of inorganic salt (B) amounts to 1 to 80 wt.-%, more preferably 5 to 70 wt.-%, still more preferably 12 to 60 wt.-%, yet more preferably 17 to 50 wt.-% and most preferably 25 to 45 wt.-% and in particular 29 to 41 wt.-%, based on the total weight of the pharmaceutical dosage form.

In a preferred embodiment, the content of inorganic salt (B) is within the range of 30±9 wt.-%, more preferably 30±8 wt.-%, still more preferably 30±7 wt.-%, yet more preferably 30±6 wt. %, most preferably 30±5 wt.-%, and in particular 30±2.5 wt.-%, based on the total weight of the pharmaceutical dosage form.

In another preferred embodiment, the content of inorganic salt (B) is within the range of 40±9 wt.-%, more preferably 40±8 wt.-%, still more preferably 40±7 wt.-%, yet more preferably 40±6 wt.-%, most preferably 40±5 wt.-%, and in particular 40±2.5 wt.-%, based on the total weight of the pharmaceutical dosage form.

It has been surprisingly found that the mechanical properties of the (tamper-resistant) pharmaceutical dosage form according to the invention, particularly its increased breaking strength are not diminished when adding substantial amounts of inorganic salt (B). This is particularly surprising, as one would expect that a high breaking strength can only be achieved by means of suitable polymers in suitable amounts and processed under appropriate conditions (typically pressure and heat). Inorganic salt (B), however, is no polymer.

Still further, it has been surprisingly found that inorganic salt (B) can influence the release characteristics of a controlled release matrix comprising a polyalkylene oxide (C), although in case of the pharmaceutical dosage forms according to the invention said polyalkylene oxide (C) provides a breaking strength of at least 500 N to the overall pharmaceutical dosage form. There is indication that in conventional hydrophilic monolithic polymeric matrices not exhibiting a breaking strength of at least 500 N, matrix swelling, matrix stiffening, matrix scaffolding via electrolyte interaction and constantly changing peripheral densification play a central role in electrolyte-induced compositional heterogeneity. Surprisingly, such processes also appear to take place in the dosage forms according to the invention, although one would expect a completely different behavior due to the specific mechanical properties.

Furthermore said pharmaceutical dosage form can be produced with a significantly reduced amount of process steps without losing the tamper resistant abilities.

Furthermore, it has been surprisingly found that the in vitro release profile of the pharmaceutical dosage form can be substantially independent from the pH value. Preferably, the in vitro release profile of the pharmaceutical dosage form follows zero order kinetics within the range of from pH 1 to pH 7.

In a preferred embodiment, inorganic salt (B) is homogeneously distributed in the pharmaceutical dosage form according to the invention. Preferably, the pharmacologically active ingredient (A) and inorganic salt (B) are intimately homogeneously distributed in the pharmaceutical dosage form so that the pharmaceutical dosage form does not contain any segments where either pharmacologically active ingredient (A) is present in the absence of inorganic salt (B) or where inorganic salt (B) is present in the absence of pharmacologically active ingredient (A).

When the pharmaceutical dosage form is film coated, the inorganic salt (B) is preferably homogeneously distributed in the core of the pharmaceutical dosage form, i.e. the film coating preferably does not contain inorganic salt (B).

The pharmaceutical dosage form according to the invention contains a polyalkylene oxide (C). The active ingredient (A) is present, preferably embedded in a controlled-release matrix comprising said polyalkylene oxide as well as inorganic salt (B).

Preferably, the polyalkylene oxide (C) is selected from polymethylene oxide, polyethylene oxide and polypropylene oxide, or copolymers or mixtures thereof.

The polyalkylene oxide (C) has a weight average molecular weight ($M_W$), preferably also a viscosity average molecular weight ($M_\eta$) of at least 200,000 g/mol or at least 500,000 g/mol, preferably at least 1,000,000 g/mol or at least 2,500,000 g/mol, more preferably in the range of about 1,000,000 g/mol to about 15,000,000 g/mol, and most preferably in the range of about 5,000,000 g/mol to about 10,000,000 g/mol.

Suitable methods to determine $M_W$ and $M_n$ are known to a person skilled in the art. $M_n$ is preferably determined by rheological measurements, whereas $M_W$ can be determined by gel permeation chromatography (GPC).

Preferably, the content of the polyalkylene oxide (C) is within the range of from 20 to 99 wt. %, more preferably 25 to 95 wt.-%, still more preferably 30 to 90 wt.-%, yet more preferably 30 to 85 wt.-%, most preferably 30 to 80 wt.-% and in particular 30 to 75 wt.-% or 45 to 70 wt.-%, based on the total weight of the pharmaceutical dosage form. The content of the polyalkylene oxide is at least 20 wt.-%, preferably at least 25 wt.-%, more preferably at least 30 wt.-%, still more preferably at least 35 wt.-% and in particular at least 40 wt.-%, based on the total weight of the pharmaceutical dosage form.

In a preferred embodiment, the overall content of polyalkylene oxide (C) is within the range of 25±5 wt.-%. In another preferred embodiment, the overall content of polyalkylene oxide (C) is within the range of 35±15 wt.-%, more preferably 35±10 wt.-%, and in particular 35±5 wt.-%. In still another preferred embodiment, the overall content of polyalkylene oxide (C) is within the range of 45±20 wt.-%, more preferably 45±15 wt.-%, most preferably 45±10 wt.-%, and in particular 45±5 wt.-%. In yet another preferred embodiment, the overall content of polyalkylene oxide (C) is within the range of 55±20 wt.-%, more preferably 55±15 wt.-%, most preferably 55±10 wt.-%, and in particular 55±5 wt.-%. In a further preferred embodiment, the overall content of polyalkylene oxide (C) is within the range of 65±20 wt.-%, more preferably 65±15 wt.-%, most preferably 65±10 wt.-%, and in particular 65±5 wt.-%. In still a further a preferred embodiment, the overall content of polyalkylene oxide (C) is within the range of 75±20 wt.-%, more preferably 75±15 wt.-%, most preferably 75±10 wt.-%, and in particular 75±5 wt.-%. In a still further a preferred embodiment, the overall content of polyalkylene oxide (C) is within the range of 80±15 wt.-%, more preferably 80±10 wt.-%, and most preferably 80±5 wt.-%.

Polyalkylene oxide (C) may comprise a single polyalkylene oxide having a particular average molecular weight, or a mixture (blend) of different polymers, such as two, three, four or five polymers, e.g., polymers of the same chemical nature but different average molecular weight, polymers of different chemical nature but same average molecular weight, or polymers of different chemical nature as well as different molecular weight.

For the purpose of the specification, a polyalkylene glycol has a molecular weight of up to 20,000 g/mol whereas a polyalkylene oxide has a molecular weight of more than 20,000 g/mol. In a preferred embodiment, the weight average over all molecular weights of all polyalkylene oxides that are contained in the pharmaceutical dosage form is at least 200,000 g/mol. Thus, polyalkylene glycols, if any, are preferably not taken into consideration when determining the weight average molecular weight of polyalkylene oxide (C).

In a preferred embodiment, polyalkylene oxide (C) is homogeneously distributed in the pharmaceutical dosage form according to the invention. Preferably, the pharmacologically active ingredient (A) and polyalkylene oxide (C) are intimately homogeneously distributed in the pharmaceutical dosage form so that the pharmaceutical dosage form does not contain any segments where either pharmacologically active ingredient (A) is present in the absence of polyalkylene oxide (C) or where polyalkylene oxide (C) is present in the absence of pharmacologically active ingredient (A).

When the pharmaceutical dosage form is film coated, the polyalkylene oxide (C) is preferably homogeneously distributed in the core of the pharmaceutical dosage form, i.e. the film coating preferably does not contain polyalkylene oxide (C). Nonetheless, the film coating as such may of course contain one or more polymers, which however, preferably differ from the polyalkylene oxide (C) contained in the core.

The polyalkylene oxide (C) may be combined with one or more different polymers selected from the group consisting of polyalkylene oxide, preferably polymethylene oxide, polyethylene oxide, polypropylene oxide; polyethylene, polypropylene, polyvinyl chloride, polycarbonate, polystyrene, polyvinylpyrrolidone, poly(alk)acrylate, poly(hydroxy fatty acids), such as for example poly(3-hydroxybutyrate-co-3-hydroxyvalerate) (Biopol®), poly(hydroxyvaleric acid); polycaprolactone, polyvinyl alcohol, polyesteramide, polyethylene succinate, polylactone, polyglycolide, polyurethane, polyamide, polylactide, polyacetal (for example polysaccharides optionally with modified side chains), polylactide/glycolide, polylactone, polyglycolide, polyorthoester, polyanhydride, block polymers of polyethylene glycol and polybutylene terephthalate (Polyactive®), polyanhydride (Polifeprosan), copolymers thereof, block-copolymers thereof, and mixtures of at least two of the stated polymers, or other polymers with the above characteristics.

Preferably, the molecular weight dispersity $M_W/M_n$ of polyalkylene oxide (C) is within the range of 2.5±2.0, more preferably 2.5±1.5, still more preferably 2.5±1.0, yet more preferably 2.5±0.8, most preferably 2.5±0.6, and in particular 2.5±0.4.

The polyalkylene oxide (C) preferably has a viscosity at 25° C. of 30 to 17,600 cP, more preferably 55 to 17,600 cP, still more preferably 600 to 17,600 cP and most preferably 4,500 to 17,600 cP, measured in a 5 wt.-% aqueous solution using a model RVF Brookfield viscosimeter (spindle no. 2/rotational speed 2 rpm); of 400 to 4,000 cP, more preferably 400 to 800 cP or 2,000 to 4,000 cP, measured on a 2 wt.-% aqueous solution using the stated viscosimeter (spindle no. 1 or 3/rotational speed 10 rpm); or of 1,650 to 10,000 cP, more preferably 1,650 to 5,500 cP, 5,500 to 7,500 cP or 7,500 to 10,000 cP, measured on a 1 wt. % aqueous solution using the stated viscosimeter (spindle no. 2/rotational speed 2 rpm).

In a preferred embodiment, the relative weight ratio of polyalkylene oxide (C) to inorganic salt (B) is within the range of from 20:1 to 0.1:1, more preferably 15:1 to 0.25:1, still more preferably 10:1 to 0.4:1, yet more preferably 5:1 to 0.5:1, most preferably 3:1 to 0.75:1 and in particular 1.6:1 to 0.85:1. In a preferred embodiment, the content of polyalkylene oxide (C) in the pharmaceutical dosage form exceeds the content of inorganic salt (B). In another preferred embodiment, the content of inorganic salt (B) in the pharmaceutical dosage form exceeds the content of polyalkylene oxide (C).

Preferably, the relative weight ratio of the polyalkylene oxide (C) to the pharmacologically active ingredient (A) is at least 0.5:1, more preferably at least 1:1, at least 2:1, at least 3:1, at least 4:1, at least 5:1, at least 6:1, at least 7:1, at least 8:1 or at least 9:1; still more preferably at least 10:1 or at least 15:1, yet more preferably at least 20:1, most preferably at least 30:1 and in particular at least 40:1. In a preferred embodiment, the relative weight ratio of the polyalkylene oxide (C) to the pharmacologically active ingredient (A) is within the range of from 3:1 to 50:1, more preferably 3:1 to 40:1 and in particular 3:1 to 30:1.

Besides the pharmacologically active ingredient (A), the inorganic salt (B) and the polyalkylene oxide (C), the pharmaceutical dosage form according to the invention may contain further ingredients, e.g. one or more conventional pharmaceutical excipient(s), e.g. fillers, glidants, binding agents, granulating agents, anti-caking agents, lubricants, flavours, dyes, and/or preservatives.

Preferably, the pharmaceutical dosage form further comprises a plasticizer. The plasticizer improves the processability of the polyalkylene oxide (C) and optionally, also of the inorganic salt (B). A preferred plasticizer is polyalkylene glycol, like polyethylene glycol, triacetin, fatty acids, fatty acid esters, waxes and/or microcrystalline waxes. Particularly preferred plasticizers are polyethylene glycols, such as PEG 6000.

Preferably, the content of the plasticizer is within the range of from 0.1 to 25 wt.-%, more preferably 0.5 to 22.5 wt.-%, still more preferably 1.0 to 20 wt.-%, yet more preferably 2.5 to 17.5 wt.-%, most preferably 5.0 to 15 wt.-% and in particular 7.5 to 12.5 wt.-%, based on the total weight of the pharmaceutical dosage form.

In a preferred embodiment, the plasticizer is a polyalkylene glycol having a content within the range of 10±8 wt.-%, more preferably 10±6 wt.-%, still more preferably 10±5 wt.-%, yet more preferably 10±4 wt.-%, most preferably 10±3 wt.-%, and in particular 10±2 wt.-%, based on the total weight of the pharmaceutical dosage form.

In another preferred embodiment, the plasticizer is a polyalkylene glycol having a content within the range of 15±8 wt.-%, more preferably 15±6 wt.-%, still more preferably 15±5 wt.-%, yet more preferably 15±4 wt.-%, most preferably 15±3 wt.-%, and in particular 15±2 wt.-%, based on the total weight of the pharmaceutical dosage form.

In a preferred embodiment, the relative weight ratio of the polyalkylene oxide (C) to the polyalkylene glycol is within the range of 4.2±2:1, more preferably 4.2±1.5:1, still more preferably 4.2±1:1, yet more preferably 4.2±0.5:1, most preferably 4.2±0.2:1, and in particular 4.2±0.1:1. This ratio satisfies the requirements of relative high polyalkylene oxide (C) content and good extrudability.

When manufacturing the dosage forms from slices that are obtained by cutting the extrudate strand, the weight of the slices determines the weight of the resulting dosage form. Pronounced variation in weight of these slices results in an accordant weight deviation of dosage forms from the target weight. The weight variation of slices depends strongly on the surface properties of the extrudate strand. A strand with a thoroughly smooth surface allows the generation of slices exhibiting a low weight variation. In contrast, a wavy or shark skinning strand results in slices exhibiting a higher weight variation thereby increasing the number of rejects. It has been surprisingly found that the surface properties of the extrudate strand can be triggered by the polyalkylene oxide:polyalkylene glycol weight ratio.

Preferably, the pharmaceutical dosage form further comprises an anti-oxidant. Suitable antioxidants include ascorbic acid, butylated hydroxyanisole (BHA), butylated hydroxytoluene (BHT), salts of ascorbic acid, monothioglycerol, phosphorous acid, vitamin C, vitamin E and the derivatives thereof, coniferyl benzoate, nordihydroguajaretic acid, gallus acid esters, sodium bisulfite, particularly preferably butylhydroxytoluene or butylhydroxyanisole and α-tocopherol. The antioxidant is preferably used in quantities of 0.01 to 10 wt.-%, preferably of 0.03 to 5 wt.-%, relative to the total weight of the pharmaceutical dosage form.

In a preferred embodiment, the pharmaceutical dosage form further comprises an acid, preferably citric acid. The amount of acid is preferably in the range of 0.01 to about 20 wt.-%, more preferably in the range of 0.02 to about 10 wt.-%, and most preferably in the range of 0.05 to about 5 wt.-%.

In a preferred embodiment, the pharmaceutical dosage form contains a natural, semisynthetic or synthetic wax. Waxes with a softening point of at least 50° C., more preferably 60° C. are preferred. Carnauba wax and beeswax are particularly preferred, especially carnauba wax.

In a preferred embodiment, the pharmaceutical dosage form further comprises another polymer which is preferably selected from cellulose esters and cellulose ethers, in particular hydroxypropyl methylcellulose (HPMC). The amount of the further polymer, preferably hydroxypropyl methylcellulose, preferably ranges from 0.1 wt.-% to about 30 wt.-%, more preferably in the range of 1.0 wt.-% to about 20 wt.-%, and most preferably in the range of 2.0 wt.-% to about 15 wt.-%.

In another preferred embodiment, the pharmaceutical dosage form according to the invention does not contain any further polymer besides the polyalkylene oxide (C) and optionally, the polyethylene glycol.

The pharmaceutical dosage form according to the invention is preferably an oral dosage form, particularly a tablet. It is also possible, however, to administer the pharmaceutical dosage form via different routes and thus, the pharmaceutical dosage form may alternatively be adapted for buccal, lingual, rectal or vaginal administration. Implants are also possible.

Preferably, the pharmaceutical dosage form is monolithic. Preferably, the pharmaceutical dosage form is neither in film form, nor multi-particulate.

In a preferred embodiment, the pharmaceutical dosage form according to the invention is a round tablet. Tablets of this embodiment preferably have a diameter in the range of about 1 mm to about 30 mm, in particular in the range of about 2 mm to about 25 mm, more in particular about 5 mm to about 23 mm, even more in particular about 7 mm to about 13 mm; and a thickness in the range of about 1.0 mm to about 12 mm, in particular in the range of about 2.0 mm to about 10 mm, even more in particular from 3.0 mm to about 9.0 mm, even further in particular from about 4.0 mm to about 8.0 mm.

In another preferred embodiment, the pharmaceutical dosage form according to the invention is an oblong tablet. Tablets of this embodiment preferably have a lengthwise extension (longitudinal extension) of about 1 mm to about 30 mm, in particular in the range of about 2 mm to about 25 mm, more in particular about 5 mm to about 23 mm, even more in particular about 7 mm to about 20 mm; and a thickness in the range of about 1.0 mm to about 12 mm, in particular in the range of about 2.0 mm to about 10 mm, even more in particular from 3.0 mm to about 9.0 mm, even further in particular from about 4.0 mm to about 8.0 mm.

The pharmaceutical dosage form according to the invention has preferably a weight in the range of 0.01 to 1.5 g, more preferably in the range of 0.05 to 1.2 g, still more preferably in the range of 0.1 g to 1.0 g, yet more preferably in the range of 0.2 g to 0.9 g, and most preferably in the range of 0.25 g to 0.8 g.

The pharmaceutical dosage form according to the invention is preferably prepared by thermoforming, preferably by hot-melt extrusion, although also other methods of thermoforming may be used in order to manufacture the pharmaceutical dosage form according to the invention such as press-molding at elevated temperature or heating of tablets that were manufactured by conventional compression in a first step and then heated above the softening temperature of the polymer in the tablet in a second step to form hard tablets. In this regards, thermoforming means the forming or molding of a mass after the application of heat. In a preferred embodiment, the pharmaceutical dosage form is thermoformed by hot-melt extrusion.

In a preferred embodiment, the pharmaceutical dosage form is prepared by hot melt-extrusion, preferably by means of a twin-screw-extruder. Melt extrusion preferably provides a melt-extruded strand that is preferably cut into monoliths, which are then compressed and formed into tablets. In this regard, the term "tablets" is preferably not to be understood as dosage forms being made by compression of powder or granules (compressi) but rather, as shaped extrudates. Preferably, compression is achieved by means of a die and a punch, preferably from a monolithic mass obtained by melt extrusion. If obtained via melt extrusion, the compressing step is preferably carried out with a monolithic mass exhibiting ambient temperature, that is, a temperature in the range from 20 to 25° C. The strands obtained by way of extrusion can either be subjected to the compression step as such or can be cut prior to the compression step. This cutting can be performed by usual techniques, for example using rotating knives or compressed air. Alternatively, the shaping can take place as described in EP-A 240 906 by the extrudate being passed between two counter-rotating calendar rolls and being shaped directly to tablets. It is of course also possible to subject the extruded strands to the compression step or to the cutting step when still warm, that is more or less immediately after the extrusion step. The extrusion is preferably carried out by means of a twin-screw extruder.

The pharmaceutical dosage form of the invention can optionally be provided, partially or completely, with a conventional coating. The dosage forms of the present invention are preferably film coated with conventional film coating compositions. Particularly preferably, the dosage forms according to the invention are either not coated at all or completely coated, but preferably not partially coated.

Suitable coating materials are commercially available, e.g. under the trademarks Opadry® and Eudragit®.

Examples of suitable materials include cellulose esters and cellulose ethers, such as methylcellulose (MC), hydroxypropylmethylcellulose (HPMC), hydroxypropylcellulose (HPC), hydroxyethylcellulose (HEC), sodium carboxymethylcellulose (Na-CMC), ethylcellulose (EC), cellulose acetate phthalate (CAP), hydroxypropylmethylcellulose phthalate (HPMCP); poly(meth)acrylates, such as aminoalkylmethacrylate copolymers, ethylacrylate methylmethacrylate copolymers, methacrylic acid methylmethacrylate copolymers, methacrylic acid methylmethacrylate copolymers; vinyl polymers, such as polyvinylpyrrolidone, polyvinyl-acetatephthalate, polyvinyl alcohol, polyvinylacetate; and natural film formers, such as shellack.

In a particularly preferred embodiment, the coating is water-soluble. In a preferred embodiment, the coating is based on polyvinyl alcohol, such as polyvinyl alcohol-part. Hydrolyzed, and may additionally contain polyethylene glycol, such as macrogol 3350, and/or pigments. In another preferred embodiment, the coating is based on hydroxypropylmethylcellulose, preferably hypromellose type 2910 having a viscosity of 3 to 15 mPas.

The coating can be resistant to gastric juices and dissolve as a function of the pH value of the release environment. By means of this coating, it is possible to ensure that the pharmaceutical dosage form according to the invention passes through the stomach undissolved and the active ingredient is only released in the intestines. The coating which is resistant to gastric juices preferably dissolves at a pH value of between 5 and 7.5. Corresponding materials and methods for the delayed release of active ingredients and for the application of coatings which are resistant to gastric juices are known to the person skilled in the art, for example from "Coated Pharmaceutical dosage forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers.

The coating can also be applied e.g. to improve the aesthetic impression and/or the taste of the dosage forms and the ease with which they can be swallowed. Coating the dosage forms of the present invention can also serve other purposes, e.g. improving stability and shelf-life. Suitable coating formulations comprise a film forming polymer such as, for example, polyvinyl alcohol or hydroxypropyl methylcellulose, e.g. hypromellose, a plasticizer such as, for example, a glycol, e.g. propylene glycol or polyethylene glycol, an opacifier, such as, for example, titanium dioxide, and a film smoothener, such as, for example, talc. Suitable coating solvents are water as well as organic solvents. Examples of organic solvents are alcohols, e.g. ethanol or isopropanol, ketones, e.g. acetone, or halogenated hydrocarbons, e.g. methylene chloride. Optionally, the coating can contain a therapeutically effective amount of one or more active ingredients to provide for an immediate release of said active ingredient (A) and thus for an immediate relief of the symptoms treated by said active ingredient (A). Coated dosage forms of the present invention are preferably prepared by first making the cores and subsequently coating said cores using conventional techniques, such as coating in a coating pan.

According to the invention, the active ingredient (A) is present, preferably embedded in a controlled-release matrix comprising inorganic salt (B) and polyalkylene oxide (C).

Controlled release of an active ingredient from an oral dosage form is known to a person skilled in the art. For the purpose of the specification, controlled release encompasses delayed release, retarded release, sustained release, extended release, prolonged release, and the like.

Controlled or prolonged release is understood according to the invention preferably to mean a release profile in which the pharmacologically active ingredient (A) is released over a relatively long period with reduced intake frequency with the purpose of extended therapeutic action. Preferably, the meaning of the term "prolonged release" is in accordance with the European guideline on the nomenclature of the release profile of pharmaceutical dosage forms (CHMP). This is achieved in particular with peroral administration. The expression "at least partially delayed or prolonged release" covers according to the invention any pharmaceutical dosage forms which ensure modified release of the opioids (A) contained therein. The pharmaceutical dosage forms preferably comprise coated or uncoated pharmaceutical dosage forms, which are produced with specific auxiliary substances, by particular processes or by a combination of the two possible options in order purposefully to change the release rate or location of release.

In the case of the pharmaceutical dosage forms according to the invention, the release time profile of a controlled release form may be modified e.g. as follows: extended release, repeat action release, prolonged release and sustained release.

For the purpose of the specification "controlled release" preferably means a product in which the release of active ingredient over time is controlled by the type and composition of the formulation. For the purpose of the specification "extended release" preferably means a product in which the release of active ingredient is delayed for a finite lag time, after which release is unhindered. For the purpose of the specification "repeat action release" preferably means a product in which a first portion of active ingredient is released initially, followed by at least one further portion of active ingredient being released subsequently. For the purpose of the specification "prolonged release" preferably means a product in which the rate of release of active ingredient from the formulation after administration has been reduced over time, in order to maintain therapeutic activity, to reduce toxic effects, or for some other therapeutic purpose. For the purpose of the specification "sustained release" preferably means a way of formulating a medicine so that it is released into the body steadily, over a long period of time, thus reducing the dosing frequency. For further details, reference may be made, for example, to K. H. Bauer, Lehrbuch der Pharmazeutischen Technologie, 6th edition, W V G Stuttgart, 1999; and Eur. Ph.

Preferably, under physiological conditions the pharmaceutical dosage form according to the invention has released after 30 minutes 0.1 to 75%, after 240 minutes 0.5 to 95%, after 480 minutes 1.0 to 100% and after 720 minutes 2.5 to 100% of the pharmacologically active ingredient (A). Further preferred release profiles $R_1$ to $R_6$ are summarized in the table here below [all data in wt.-% of released pharmacologically active ingredient (A)]:

| time | $R_1$ | $R_2$ | $R_3$ | $R_4$ | $R_5$ | $R_6$ |
|---|---|---|---|---|---|---|
| 60 min | 0-30 | 0-50 | 0-50 | 15-25 | 20-30 | 20-50 |
| 120 min | 0-40 | 0-75 | 0-75 | 25-40 | 35-50 | 40-75 |
| 240 min | 3-55 | 3-95 | 10-95 | 40-70 | 55-75 | 60-95 |
| 480 min | 10-65 | 10-100 | 35-100 | 60-90 | 80-95 | 80-100 |
| 720 min | 20-75 | 20-100 | 55-100 | 70-100 | 90-100 | 90-100 |
| 960 min | 30-88 | 30-100 | 70-100 | >80 | 95-100 | |
| 1440 min | 50-100 | 50-100 | >90 | | | |
| 2160 min | >80 | >80 | | | | |

Further preferred release profiles $R_1$ to $R_6$ are summarized in the table here below [all data in wt.-% of released pharmacologically active ingredient (A)]:

| time | $R_7$ | $R_8$ | $R_9$ | $R_{10}$ | $R_{11}$ | $R_{12}$ |
|---|---|---|---|---|---|---|
| 30 min | 17.5 ± 7.5 | 17.5 ± 6.5 | 17.5 ± 5.5 | 17.5 ± 4.5 | 17.5 ± 3.5 | 17.5 ± 2.5 |
| 60 min | 27.0 ± 8.0 | 27.0 ± 7.0 | 27.0 ± 6.0 | 27.0 ± 5.0 | 27.0 ± 4.0 | 27.0 ± 3.0 |
| 120 min | 41.5 ± 9.5 | 41.5 ± 8.5 | 41.5 ± 7.5 | 41.5 ± 6.5 | 41.5 ± 5.5 | 41.5 ± 4.5 |
| 240 min | 64.5 ± 12.5 | 64.5 ± 11.5 | 64.5 ± 10.5 | 64.5 ± 9.5 | 64.5 ± 8.5 | 64.5 ± 7.5 |
| 480 min | 88.0 ± 12.0 | 88.0 ± 11.0 | 88.0 ± 10.0 | 88.0 ± 9.0 | 88.0 ± 8.0 | 88.0 ± 7.0 |
| 720 min | 96.0 ± 9.0 | 96.0 ± 8.0 | 96.0 ± 7.0 | 96.0 ± 6.0 | 96.0 ± 5.0 | 96.0 ± 4.0 |
| 840 min | 97.5 ± 7.5 | 97.5 ± 6.5 | 97.5 ± 5.5 | 97.5 ± 4.5 | 97.5 ± 3.5 | 97.5 ± 2.5 |

Preferably, the release profile of the pharmaceutical dosage form according to the present invention is stable upon storage, preferably upon storage at elevated temperature, e.g. 40° C., for 3 months in sealed containers. In this regard "stable" means that when comparing the initial release profile with the release profile after storage, at any given time point the release profiles deviate from one another by not more than 20%, more preferably not more than 15%, still more preferably not more than 10%, yet more preferably not more than 7.5%, most preferably not more than 5.0% and in particular not more than 2.5%.

Preferably, under in vitro conditions the pharmaceutical dosage form has released after 0.5 h 1.0 to 35 wt.-%, after 1 h 5.0 to 45 wt.-%, after 2 h 10 to 60 wt.-%, after 4 h at least 15 wt.-%, after 6 h at least 20 wt.-%, after 8 h at least 25 wt.-% and after 12 h at least 30 wt.-% of the pharmacologically active ingredient (A) that was originally contained in the pharmaceutical dosage form.

Suitable in vitro conditions are known to the skilled artisan. In this regard it can be referred to, e.g., the Eur. Ph. Preferably, the release profile is measured under the following conditions: Paddle apparatus equipped with sinker, 75 rpm, 37±5° C., 600 mL simulated intestinal fluid pH 6.8 (phosphate buffer) or pH 4.5. In a preferred embodiment, the rotational speed of the paddle is increased to 100 rpm.

In a preferred embodiment, the pharmaceutical dosage form according to the invention is adapted for administration once daily. In another preferred embodiment, the pharmaceutical dosage form according to the invention is adapted for administration twice daily. In still another preferred embodiment, the pharmaceutical dosage form according to the invention is adapted for administration thrice daily.

For the purpose of the specification, "twice daily" means equal or nearly equal time intervals, i.e., about every 12 hours, or different time intervals, e.g., 8 and 16 hours or 10 and 14 hours, between the individual administrations.

For the purpose of the specification, "thrice daily" means equal or nearly equal time intervals, i.e., about every 8 hours, or different time intervals, e.g., 6, 6 and 12 hours; or 7, 7 and 10 hours, between the individual administrations.

Preferably, the pharmaceutical dosage form according to the invention releases after 5 h at most 99%, more preferably at most 90%, still more preferably at most 75%, and most preferably at most 60% of the active ingredient (A).

The inorganic salt (B) is preferably hydrophilic, meaning that a matrix comprising inorganic salt (B) and polyalkylene oxide (C) tends to swell upon contact with aqueous fluids following administration, and preferably results in a viscous, pharmacologically active ingredient release regulating gel layer.

In a preferred embodiment, the matrix comprising the inorganic salt (B) and the polyalkylene oxide (C) contains inorganic salt (B) in such a quantity that under in vitro conditions the release of the active ingredient (A) is additionally retarded, and the release profile of the pharmacologically active ingredient (A) from said matrix comprises at least a time interval during which the release follows a zero order kinetics, compared to a thus identical, comparative pharmaceutical dosage form wherein the inorganic salt (B) is substituted with the corresponding amount of hydroxylpropyl methyl cellulose (HPMC) or lactose.

In a particular preferred embodiment,
 the pharmaceutical dosage form is thermoformed, preferably by hot melt-extrusion; and/or
 the pharmaceutical dosage form exhibits a breaking strength of at least 1500 N; and/or
 the pharmaceutical dosage form is adapted for administration once-daily, twice daily or thrice-daily; and/or the pharmacologically active ingredients (A) is selected from the group of opioids and opiates; and or the content of inorganic salt (B) ranges from 2.0 wt.-% to 50 wt.-%; and/or the polyalkylene oxide (C) is selected from polymethylene oxide, polyethylene oxide and polypropylene oxide, or copolymers or mixtures thereof; having a weight average molecular weight ($M_W$) of at least 500,000 g/mol, more preferably within the range of from 1,000,000 g/mol to 10,000,000 g/mol; and/or the content of polyalkylene oxide (C) is at least 30 wt.-%, based on the total weight of the dosage form.

In a preferred embodiment, the pharmaceutical dosage form according to the invention contains no substances which irritate the nasal passages and/or pharynx, i.e. substances which, when administered via the nasal passages and/or pharynx, bring about a physical reaction which is either so unpleasant for the patient that he/she does not wish to or cannot continue administration, for example burning, or physiologically counteracts taking of the corresponding active ingredient, for example due to increased nasal secretion or sneezing. Further examples of substances which irritate the nasal passages and/or pharynx are those which cause burning, itching, urge to sneeze, increased formation of secretions or a combination of at least two of these stimuli. Corresponding substances and the quantities thereof which are conventionally to be used are known to the person skilled in the art. Some of the substances which irritate the nasal passages and/or pharynx are accordingly based on one or more constituents or one or more plant parts of a hot substance pharmacologically active ingredient. Corresponding hot substance pharmacologically active ingredients are known per se to the person skilled in the art and are described, for example, in "Pharmazeutische Biologie—Drogen und ihre Inhaltsstoffe" by Prof. Dr. Hildebert Wagner, 2nd., revised edition, Gustav Fischer Verlag, Stuttgart-New York, 1982, pages 82 et seq. The corresponding description is hereby introduced as a reference and is deemed to be part of the disclosure.

The pharmaceutical dosage form according to the invention furthermore preferably contains no antagonists for the pharmacologically active ingredient (A), preferably no antagonists against psychotropic substances, in particular no antagonists against opioids (A). Antagonists suitable for a given pharmacologically active ingredient (A) are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no antagonists selected from among the group comprising naloxone, naltrexone, nalmefene, nalide, nalmexone, nalorphine or naluphine, in each case optionally in the form of a corresponding physiologically acceptable compound, in particular in the form of a base, a salt or solvate; and no neuroleptics, for example a compound selected from among the group comprising haloperidol, promethacine, fluphenazine, perphenazine, levomepromazine, thioridazine, perazine, chlorpromazine, chlorprothixine, zuclopenthixol, flupentixol, prothipendyl, zotepine, benperidol, pipamperone, melperone and bromperidol.

The pharmaceutical dosage form according to the invention furthermore preferably contains no emetic. Emetics are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no emetic based on one or more constituents of ipecacuanha (ipecac) root, for example based on the constituent emetine, as are, for example, described in "Pharmazeutische Biologie—Drogen und ihre Inhaltsstoffe" by Prof. Dr. Hildebert Wagner, 2nd, revised edition, Gustav Fischer Verlag, Stuttgart, New York, 1982. The corresponding literature description is hereby introduced as a reference and is deemed to be part of the disclosure. The pharmaceutical dosage form according to the invention preferably also contains no apomorphine as an emetic.

Finally, the pharmaceutical dosage form according to the invention preferably also contains no bitter substance. Bitter substances and the quantities effective for use may be found in US-2003/0064099 A1, the corresponding disclosure of which should be deemed to be the disclosure of the present application and is hereby introduced as a reference. Examples of bitter substances are aromatic oils, such as peppermint oil, *eucalyptus* oil, bitter almond oil, menthol, fruit aroma substances, aroma substances from lemons, oranges, limes, grapefruit or mixtures thereof, and/or denatonium benzoate.

The pharmaceutical dosage form according to the invention accordingly preferably contains neither substances which irritate the nasal passages and/or pharynx, nor antagonists for the pharmacologically active ingredient (A), nor emetics, nor bitter substances.

The pharmaceutical dosage form according to the invention has a breaking strength of at least 500 N.

The pharmaceutical dosage form according to the invention is preferably tamper-resistant. Preferably, tamper-resistance is achieved based on the mechanical properties of the pharmaceutical dosage form so that comminution is avoided or at least substantially impeded. According to the invention, the term comminution means the pulverization of the pharmaceutical dosage form using conventional means usually available to an abuser, for example a pestle and mortar, a hammer, a mallet or other conventional means for pulverizing under the action of force. Thus, tamper-resistance preferably means that pulverization of the pharmaceutical dosage form using conventional means is avoided or at least substantially impeded.

Preferably, the mechanical properties of the pharmaceutical dosage form according to the invention, particularly its breaking strength, substantially rely on the presence and spatial distribution of inorganic salt (B) and polyalkylene oxide (C), although their mere presence does typically not suffice in order to achieve said properties. The advantageous mechanical properties of the pharmaceutical dosage form according to the invention may not automatically be achieved by simply processing pharmacologically active ingredient (A), inorganic salt (B), polyalkylene oxide (C), and optionally further excipients by means of conventional methods for the preparation of pharmaceutical dosage forms. In fact, usually suitable apparatuses must be selected for the preparation and critical processing parameters must be adjusted, particularly pressure/force, temperature and time. Thus, even if conventional apparatuses are used, the process protocols usually must be adapted in order to meet the required criteria.

In general, the dosage forms exhibiting the desired properties may be obtained only if, during preparation of the dosage form, suitable components in suitable amounts are exposed to
a sufficient pressure
at a sufficient temperature
for a sufficient period of time.

Thus, regardless of the apparatus used, the process protocols must be adapted in order to meet the required criteria. Therefore, the breaking strength is separable from the composition.

The pharmaceutical dosage form according to the invention has a breaking strength of at least 500 N, preferably at least 600 N, more preferably at least 700 N, still more preferably at least 800 N, yet more preferably at least 1000 N, most preferably at least 1250 N and in particular at least 1500 N.

The "breaking strength" (resistance to crushing) of a pharmaceutical dosage form is known to the skilled person. In this regard it can be referred to, e.g., W. A. Ritschel, Die Tablette, 2. Auflage, Editio Cantor Verlag Aulendorf, 2002; H Liebermann et al., Pharmaceutical dosage forms: Tablets, Vol. 2, Informa Healthcare; 2 edition, 1990; and Encyclopedia of Pharmaceutical Technology, Informa Healthcare; 1 edition.

For the purpose of the specification, the breaking strength is preferably defined as the amount of force that is necessary in order to fracture the pharmaceutical dosage form (=breaking force). Therefore, for the purpose of the specification the pharmaceutical dosage form does preferably not exhibit the desired breaking strength when it breaks, i.e., is fractured into at least two independent parts that are separated from one another. In another preferred embodiment, however, the pharmaceutical dosage form is regarded as being broken if the force decreases by 25% (threshold value) of the highest force measured during the measurement (see below).

The pharmaceutical dosage forms according to the invention are distinguished from conventional pharmaceutical dosage forms in that, due to their breaking strength, they cannot be pulverized by the application of force with conventional means, such as for example a pestle and mortar, a hammer, a mallet or other usual means for pulverization, in particular devices developed for this purpose (tablet crushers). In this regard "pulverization" means crumbling into small particles that would immediately release the pharmacologically active ingredient (A) in a suitable medium. Avoidance of pulverization virtually rules out oral or parenteral, in particular intravenous or nasal abuse.

Conventional tablets typically have a breaking strength well below 200 N in any direction of extension. The breaking strength of conventional round tablets may be estimated according to the following empirical formula: Breaking Strength [in N]=10×Diameter Of The Tablet [in mm]. Thus, according to said empirical formula, a round tablet having a breaking strength of at least 300 N would require a diameter of at least 30 mm). Such a tablet, however, could not be swallowed. The above empirical formula preferably does not apply to the pharmaceutical dosage forms of the invention, which are not conventional but rather special.

Further, the actual mean chewing force is about 220 N (cf., e.g., P. A. Proeschel et al., J Dent Res, 2002, 81(7), 464-468). This means that conventional tablets having a breaking strength well below 200 N may be crushed upon spontaneous chewing, whereas the pharmaceutical dosage forms according to the invention may not.

Still further, when applying a gravitational acceleration of about 9.81 m/s$^2$, 500 N correspond to a gravitational force of more than 50 kg, i.e. the pharmaceutical dosage forms according to the invention can preferably withstand a weight of more than 50 kg without being pulverized.

Methods for measuring the breaking strength of a pharmaceutical dosage form are known to the skilled artisan. Suitable devices are commercially available.

For example, the breaking strength (resistance to crushing) can be measured in accordance with the Eur. Ph. 5.0, 2.9.8 or 6.0, 2.09.08 "Resistance to Crushing of Tablets". The test is intended to determine, under defined conditions, the resistance to crushing of tablets, measured by the force needed to disrupt them by crushing. The apparatus consists of 2 jaws facing each other, one of which moves towards the other. The flat surfaces of the jaws are perpendicular to the direction of movement. The crushing surfaces of the jaws are flat and larger than the zone of contact with the tablet. The apparatus is calibrated using a system with a precision of 1 Newton. The tablet is placed between the jaws, taking into account, where applicable, the shape, the break-mark and the inscription; for each measurement the tablet is oriented in the same way with respect to the direction of application of the force (and the direction of extension in which the breaking strength is to be measured). The measurement is carried out on 10 tablets, taking care that all fragments of tablets have been removed before each determination. The result is expressed as the mean, minimum and maximum values of the forces measured, all expressed in Newton.

A similar description of the breaking strength (breaking force) can be found in the USP. The breaking strength can alternatively be measured in accordance with the method described therein where it is stated that the breaking strength is the force required to cause a tablet to fail (i.e., break) in a specific plane. The tablets are generally placed between two platens, one of which moves to apply sufficient force to the tablet to cause fracture. For conventional, round (circular cross-section) tablets, loading occurs across their diameter (sometimes referred to as diametral loading), and fracture occurs in the plane. The breaking force of tablets is commonly called hardness in the pharmaceutical literature; however, the use of this term is misleading. In material science, the term hardness refers to the resistance of a surface to penetration or indentation by a small probe. The term crushing strength is also frequently used to describe the resistance of tablets to the application of a compressive load. Although this term describes the true nature of the test more accurately than does hardness, it implies that tablets are actually crushed during the test, which is often not the case.

Alternatively, the breaking strength (resistance to crushing) can be measured in accordance with WO 2005/016313, WO 2005/016314, and WO 2006/082099, which can be regarded as a modification of the method described in the Eur. Ph. The apparatus used for the measurement is preferably a "Zwick Z 2.5" materials tester, $F_{max}$=2.5 kN with a maximum draw of 1150 mm, which should be set up with one column and one spindle, a clearance behind of 100 mm and a test speed adjustable between 0.1 and 800 mm/min together with testControl software. Measurement is performed using a pressure piston with screw-in inserts and a cylinder (diameter 10 mm), a force transducer, $F_{max}$. 1 kN, diameter=8 mm, class 0.5 from 10 N, class 1 from 2 N to ISO 7500-1, with manufacturers test certificate M according to DIN 55350-18 (Zwick gross force $F_{max}$=1.45 kN) (all apparatus from Zwick GmbH & Co. KG, Ulm, Germany) with Order No BTC-FR 2.5 TH. D09 for the tester, Order No BTC-LC 0050N. P01 for the force transducer, Order No BO 70000 S06 for the centering device.

In a preferred embodiment of the invention, the breaking strength is measured by means of a breaking strength tester e.g. Sotax®, type HT100 or type HT1 (Allschwil, Switzerland). Both, the Sotax® HT100 and the Sotax® HT1 can measure the breaking strength according to two different measurement principles: constant speed (where the test jaw is moved at a constant speed adjustable from 5-200 mm/min) or constant force (where the test jaw increases force linearly adjustable from 5-100 N/sec). In principle, both measurement principles are suitable for measuring the breaking strength of the pharmaceutical dosage form according to the invention. Preferably, the breaking strength is measured at constant speed, preferably at a constant speed of 120 mm/min.

In a preferred embodiment, the pharmaceutical dosage form is regarded as being broken if it is fractured into at least two separate pieces.

The pharmaceutical dosage form according to the invention preferably exhibits mechanical strength over a wide temperature range, in addition to the breaking strength (resistance to crushing) optionally also sufficient hardness, impact resistance, impact elasticity, tensile strength and/or modulus of elasticity, optionally also at low temperatures (e.g. below −24° C., below −40° C. or in liquid nitrogen), for it to be virtually impossible to pulverize by spontaneous chewing, grinding in a mortar, pounding, etc. Thus, preferably, in direction of extension $E_1$ the comparatively high breaking strength of the pharmaceutical dosage form according to the invention is maintained even at low or very low temperatures, e.g., when the pharmaceutical dosage form is initially chilled to increase its brittleness, for example to temperatures below −25° C., below −40° C. or even in liquid nitrogen.

The pharmaceutical dosage form according to the invention is characterized by a certain degree of breaking strength. This does not mean that the pharmaceutical dosage form must also exhibit a certain degree of hardness. Hardness and breaking strength are different physical properties. Therefore, the tamper resistance of the pharmaceutical dosage form does not necessarily depend on the hardness of the pharmaceutical dosage form. For instance, due to its breaking strength, impact strength, elasticity modulus and tensile strength, respectively, the pharmaceutical dosage form can preferably be deformed, e.g. plastically, when exerting an external force, for example using a hammer, but cannot be pulverized, i.e., crumbled into a high number of fragments. In other words, the pharmaceutical dosage form according to the invention is characterized by a certain degree of breaking strength, but not necessarily also by a certain degree of form stability.

Therefore, in the meaning of the specification, a pharmaceutical dosage form that is deformed when being exposed to a force in a particular direction of extension but that does not break (plastic deformation or plastic flow) is preferably to be regarded as having the desired breaking strength in said direction of extension.

In a preferred embodiment the invention relates to a tamper-resistant pharmaceutical dosage form having a retarded release profile, especially a tamper-resistant oral dosage form having a retarded release profile, particularly a tamper-resistant tablet having a retarded release profile comprising at least one pharmaceutically active ingredient (A) (pharmacologically active compound) with potential for abuse.

The pharmaceutical dosage form according to the invention may be produced by different processes, the particularly preferred of which are explained in greater detail below.

Several suitable processes have already been described in the prior art. In this regard it can be referred to, e.g., WO 2005/016313, WO 2005/016314, WO 2005/063214, WO 2005/102286, WO 2006/002883, WO 2006/002884, WO 2006/002886, WO 2006/082097, and WO 2006/082099.

The present invention also relates to pharmaceutical dosage forms that are obtainable by any of the processes described here below.

In general, the process for the production of the pharmaceutical dosage form according to the invention preferably comprises the following steps:
(a) mixing all ingredients;
(b) optionally pre-forming the mixture obtained from step (a), preferably by applying heat and/or force to the mixture obtained from step (a), the quantity of heat supplied preferably not being sufficient to heat the polyalkylene oxide (C) up to its softening point;
(c) hardening the mixture by applying heat and force, it being possible to supply the heat during and/or before the application of force and the quantity of heat supplied being sufficient to heat the polyalkylene oxide (C) at least up to its softening point;
(d) optionally singulating the hardened mixture;
(e) optionally shaping the pharmaceutical dosage form; and
(f) optionally providing a film coating.

Heat may be supplied directly, e.g. by contact or by means of hot gas such as hot air, or with the assistance of ultrasound. Force may be applied and/or the pharmaceutical dosage form may be shaped for example by direct tabletting or with the assistance of a suitable extruder, particularly by means of a screw extruder equipped with two screws (twin-screw-extruder) or by means of a planetary gear extruder.

Preferably, hot-melt extrusion is performed in the absence of additional water.

The final shape of the pharmaceutical dosage form may either be provided during the hardening of the mixture by applying heat and force (step (c)) or in a subsequent step (step (e)). In both cases, the mixture of all components is preferably in the plastified state, i.e. preferably, shaping is performed at a temperature at least above the softening point of the polyalkylene oxide (C). However, extrusion at lower temperatures, e.g. ambient temperature, is also possible and may be preferred.

Shaping can be performed, e.g., by means of a tabletting press comprising die and punches of appropriate shape.

A particularly preferred process for the manufacture of the pharmaceutical dosage form of the invention involves hot-melt extrusion. In this process, the pharmaceutical dosage form according to the invention is produced by thermoforming with the assistance of an extruder, preferably without there being any observable consequent discoloration of the extrudate.

This process is characterized in that
a) all components are mixed,
b) the resultant mixture is heated in the extruder at least up to the softening point of the polyalkylene oxide (C) and extruded through the outlet orifice of the extruder by application of force,
c) the still plastic extrudate is singulated and formed into the pharmaceutical dosage form or
d) the cooled and optionally reheated singulated extrudate is formed into the pharmaceutical dosage form.

Mixing of the components according to process step a) may also proceed in the extruder.

The components may also be mixed in a mixer known to the person skilled in the art. The mixer may, for example, be a roll mixer, shaking mixer, shear mixer or compulsory mixer.

The, preferably molten, mixture which has been heated in the extruder at least up to the softening point of polyalkylene oxide (C) is extruded from the extruder through a die with at least one bore.

The extrusion process according to the invention requires the use of suitable extruders, preferably screw extruders. Screw extruders which are equipped with two screws (twin-screw-extruders) are particularly preferred.

The extrusion is preferably performed so that the expansion of the strand due to extrusion is not more than 30%, i.e. that when using a die with a bore having a diameter of e.g. 6 mm, the extruded strand should have a diameter of not more than 8 mm. More preferably, the expansion of the strand is not more than 25%, still more preferably not more than 20%, most preferably not more than 15% and in particular not more than 10%.

Preferably, extrusion is performed in the absence of water, i.e., no water is added. However, traces of water (e.g., caused by atmospheric humidity) may be present.

The extruder preferably comprises at least two temperature zones, with heating of the mixture at least up to the softening point of the polyalkylene oxide (C) proceeding in the first zone, which is downstream from a feed zone and optionally mixing zone. The throughput of the mixture is preferably from 1.0 kg to 15 kg/hour. In a preferred embodiment, the throughput is from 1 to 3.5 kg/hour. In another preferred embodiment, the throughput is from 4 to 15 kg/hour.

In a preferred embodiment, the die head pressure is within the range of from 25 to 100 bar. The die head pressure can be adjusted inter alia by die geometry, temperature profile and extrusion speed.

The die geometry or the geometry of the bores is freely selectable. The die or the bores may accordingly exhibit a round, oblong or oval cross-section, wherein the round cross-section preferably has a diameter of 0.1 mm to 15 mm and the oblong cross-section preferably has a maximum lengthwise extension of 21 mm and a crosswise extension of 10 mm. Preferably, the die or the bores have a round cross-section. The casing of the extruder used according to the invention may be heated or cooled. The corresponding temperature control, i.e. heating or cooling, is so arranged that the mixture to be extruded exhibits at least an average temperature (product temperature) corresponding to the softening temperature of the polyalkylene oxide (C) and does not rise above a temperature at which the pharmacologically active ingredient (A) to be processed may be damaged. Preferably, the temperature of the mixture to be extruded is adjusted to below 180° C., preferably below 150° C., but at least to the softening temperature of polyalkylene oxide (C). Typical extrusion temperatures are 120° C. and 130° C.

In a preferred embodiment, the extruder torque is within the range of from 30 to 95%. Extruder torque can be adjusted inter alia by die geometry, temperature profile and extrusion speed.

After extrusion of the molten mixture and optional cooling of the extruded strand or extruded strands, the extrudates are preferably singulated. This singulation may preferably be performed by cutting up the extrudates by means of revolving or rotating knives, water jet cutters, wires, blades or with the assistance of laser cutters.

Preferably, intermediate or final storage of the optionally singulated extrudate or the final shape of the pharmaceutical dosage form according to the invention is performed under oxygen-free atmosphere which may be achieved, e.g., by means of oxygen-scavengers.

The singulated extrudate may be press-formed into tablets in order to impart the final shape to the pharmaceutical dosage form.

The application of force in the extruder onto the at least plasticized mixture is adjusted by controlling the rotational speed of the conveying device in the extruder and the geometry thereof and by dimensioning the outlet orifice in such a manner that the pressure necessary for extruding the plasticized mixture is built up in the extruder, preferably immediately prior to extrusion. The extrusion parameters which, for each particular composition, are necessary to give rise to a pharmaceutical dosage form with desired mechanical properties, may be established by simple preliminary testing.

For example but not limiting, extrusion may be performed by means of a twin-screw-extruder type ZSE 18 or ZSE27 (Leistritz, Nürnberg, Germany), screw diameters of 18 or 27 mm. Screws having eccentric ends may be used. A heatable die with a round bore having a diameter of 7, 8, or 9 mm may be used. The extrusion parameters may be adjusted e.g. to the following values: rotational speed of the screws: 120 Upm; delivery rate 2 kg/h for a ZSE 18 or 8 kg/h for a ZSE27; product temperature: in front of die 125° C. and behind die 135° C.; and jacket temperature: 110° C.

Preferably, extrusion is performed by means of twin-screw-extruders or planetary-gear-extruders, twin-screw extruders (co-rotating or contra-rotating) being particularly preferred.

The pharmaceutical dosage form according to the invention is preferably produced by thermoforming with the assistance of an extruder without any observable consequent discoloration of the extrudates.

The process for the preparation of the pharmaceutical dosage form according to the invention is preferably performed continuously. Preferably, the process involves the extrusion of a homogeneous mixture of all components. It is particularly advantageous if the thus obtained intermediate, e.g. the strand obtained by extrusion, exhibits uniform properties. Particularly desirable are uniform density, uniform distribution of the active ingredient, uniform mechanical properties, uniform porosity, uniform appearance of the surface, etc. Only under these circumstances the uniformity of the pharmacological properties, such as the stability of the release profile, may be ensured and the amount of rejects can be kept low.

A further aspect of the invention relates to the use of a pharmacologically active ingredient (A) for the manufacture of the pharmaceutical dosage form as described above for the treatment of pain.

A further aspect of the invention relates to the use of a pharmaceutical dosage form as described above for avoiding or hindering the abuse of the pharmacologically active ingredient (A) contained therein.

A further aspect of the invention relates to the use of a pharmaceutical dosage form as described above for avoiding or hindering the unintentional overdose of the pharmacologically active ingredient (A) contained therein.

In this regard, the invention also relates to the use of a pharmacologically active ingredient (A) as described above and/or a polyalkylene oxide (C) as described above for the manufacture of the pharmaceutical dosage form according to the invention for the prophylaxis and/or the treatment of a disorder, thereby preventing an overdose of the pharmacologically active ingredient (A), particularly due to comminution of the pharmaceutical dosage form by mechanical action.

Further, the invention relates to a method for the prophylaxis and/or the treatment of a disorder comprising the administration of the pharmaceutical dosage form according to the invention, thereby preventing an overdose of the pharmacologically active ingredient (A), particularly due to comminution of the pharmaceutical dosage form by mechanical action. Preferably, the mechanical action is selected from the group consisting of chewing, grinding in a mortar, pounding, and using apparatuses for pulverizing conventional pharmaceutical dosage forms.

The following examples further illustrate the invention but are not to be construed as limiting its scope:

In all examples the dosage forms were tablets assuming a round shape with a diameter of 12 mm.

General Procedure

Polyethylene oxide, α-tocopherol, tramadol hydrochloride and all other excipients were weighted and sieved to each other. The powder was mixed and dosed gravimetrically to an extruder. Hot-melt extrusion was performed by means of a twin screw extruder of type Micro 27 GL 40 D (Leistritz, Nürnberg, Germany) that was equipped with a heatable round die having a diameter of 10 mm.

The hot extrudate was cooled on a conveyor belt and the cooled extrusion strand was comminuted to cut pieces. The cut pieces were shaped by means of an excenter press.

The breaking strength of the pharmaceutical dosage forms was measured by means of a Sotax® HT100 at a constant speed of 120 mm/min and/or a Zwick Z 2.5 at a constant speed of 10 mm/min. A tablet was regarded as failing the breaking strength test when during the measurement the force dropped below the threshold value of 25% of the maximum force that was observed during the measurement, regardless of whether the dosage form was fractured into separate pieces or not. All values are given as mean of 3 measurements (Zwick; n=3) or as a mean of 10 measurements (Sotax, n=10).

EXAMPLE I

Tablets of the following composition containing tramadol were formed:

| Excipient | Reference | Variation D | Variation E | Variation F | Variation G |
|---|---|---|---|---|---|
| Tramadol-HCl | 80.0 mg | 80.0 mg | 80.0 mg | 80.0 mg | 80.0 mg |
| Polyethyleneoxide 7,000,000 | 365.8 mg | 211.0 mg | 259.5 mg | 259.5 mg | 211.0 mg |
| Polyethylene glycole 6,000 | 90.0 mg | 62.0 mg | 76.3 mg | 76.3 mg | 62.3 mg |
| Hypromellose 100,000 mPas | 60.0 mg | — | — | — | — |
| α-Tocopherol | 1.2 mg | 1.2 mg | 1.2 mg | 1.2 mg | 1.2 mg |
| Citric Acid | 3.0 mg | 3.0 mg | 3.0 mg | 3.0 mg | 3.0 mg |
| Sodium carbonate | — | 242.8 mg | 180.0 mg | 90.0 mg | 121.4 mg |
| Pentasodium phosphate | — | — | — | 90.0 mg | 121.4 mg |
| Sum | 600.0 mg | 600.0 mg | 600.0 mg | 600.0 mg | 600.0 mg |

For each composition, the in vitro release profile of the pharmacologically active ingredient was measured in 600 ml of artificial intestinal juice (pH 6.8, phosphate buffered) at temperature of 37° C. with sinker (type 4). The rotation speed of the paddle was adjusted to 75/min. The pharmacologically active ingredient was detected by means of a spectrometric measurement with a wavelength of 271 nm.

According to the preceding table, variation D and E were tested with sodium carbonate. Dissolution curves of the tablets with 30 wt.-% and 40 wt.-% sodium carbonate in comparison to the reference tablets are illustrated in FIG. 1. The retardant effect is more pronounced for the formulation with 30 wt.-% sodium carbonate.

Figure 2:
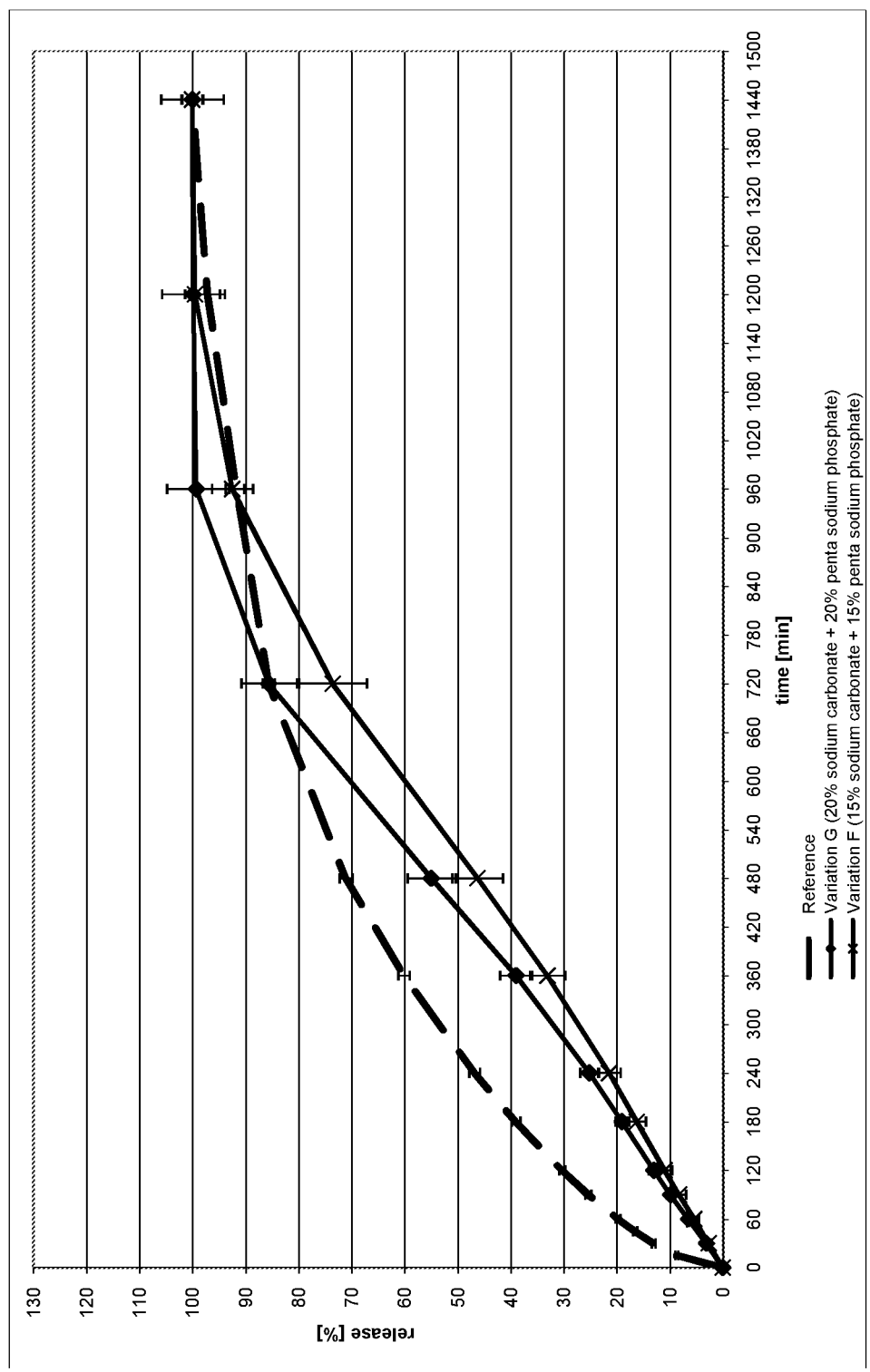
FIG. 2 shows the in vitro release profiles of a pharmaceutical dosage form according to the invention containing 15 wt.-% (Variation F) and 20 wt.-% (Variation G), respectively, each of sodium carbonate and pentasodium triphosphate in comparison to the reference tablets.

Variation F and G were tested with sodium carbonate and pentasodium triphosphate. The dissolution curves of the tablets with 20 wt.-% and 15 wt.-% of each sodium carbonate and pentasodium triphosphate in comparison to the reference are illustrated in FIG. 2. Again, the release profile shows a significantly retarded and linear release of the pharmacologically active ingredient. The release profile with the lower content of overall salts shows again the best results.

Figure 3:
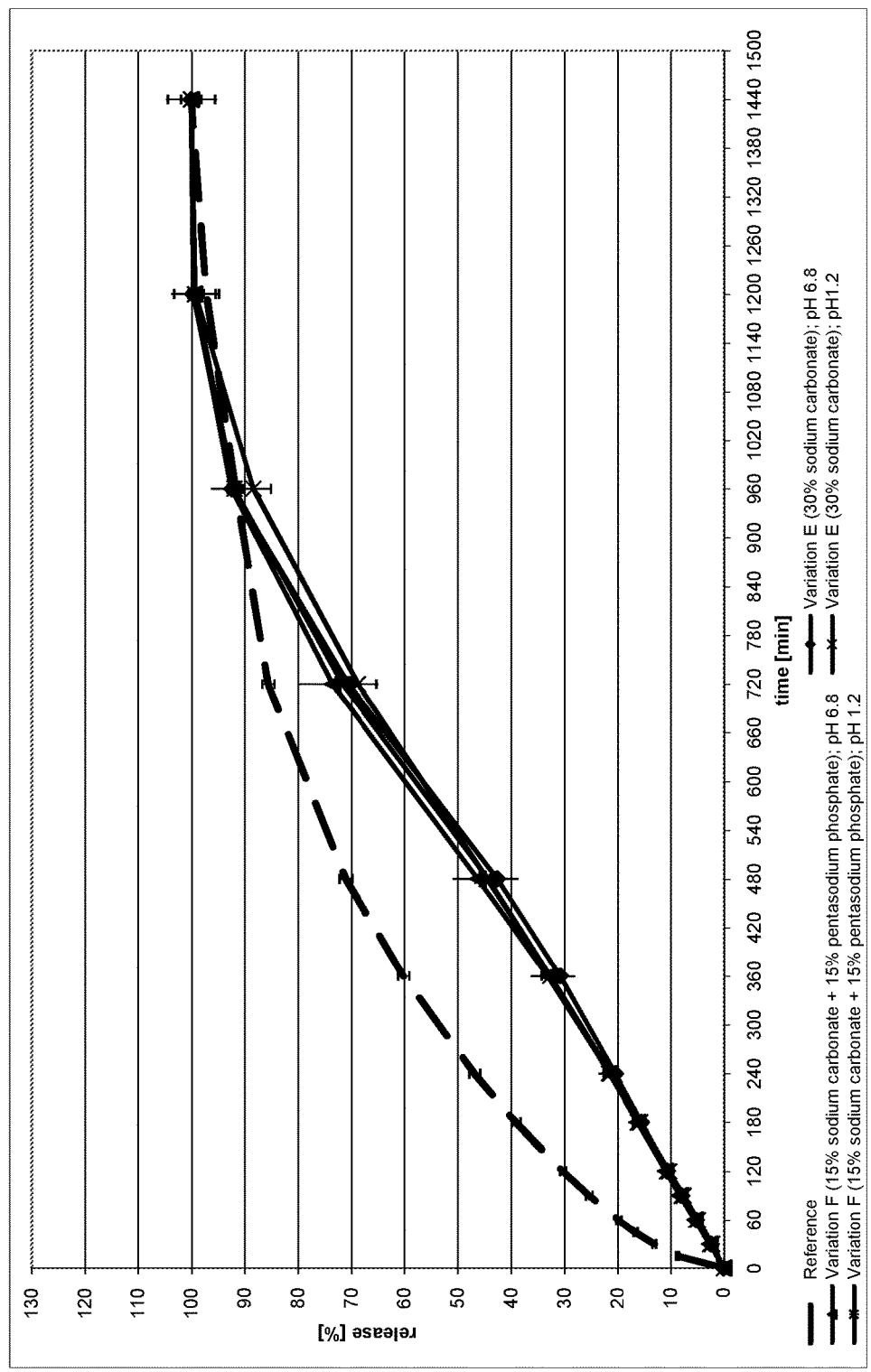
FIG. 3 shows the in vitro release profiles of a pharmaceutical dosage form according to the invention in an acidic medium, containing 30 wt.-% sodium carbonate (Variation E) and 15 wt.-% sodium carbonate with 15 wt.-% pentasodium triphosphate (Variation F) in comparison to the reference tablets.

A comparison of the dissolution in acidic medium with the dissolution curves of the tablets with 30 wt.-% sodium carbonate and 15 wt.-% of each sodium carbonate and pentasodium triphosphate in comparison to the reference tablets in illustrated in FIG. 3. The release profile of the 4 curves is comparable and hence does not depend on the pH-value.

EXAMPLE II

Tablets of the following composition containing oxymorphone were formed:

| Excipient | Per tablet [mg] | [wt.-%] |
|---|---|---|
| Oxymorphone HCL anhydrous | 80.0 | 11.1 |
| Polyethylene oxide 7,000,000 | 337.3 | 46.9 |
| Sodium Carbonate | 216.0 | 30.0 |
| Macrogol 6000 | 81.7 | 11.3 |
| α-Tocopherol | 1.4 | 0.2 |
| Citric Acid anhydrous | 3.6 | 0.5 |
| Sum | 720.0 | |

The in vitro release profile of the pharmacologically active ingredient was measured in 900 ml acidic medium (pH 1.2) and in 900 mL acetate buffered medium (pH 4.5), both at temperature of 37° C. with sinker (type 4). The rotation speed of the paddle was adjusted to 50/min. The pharmacologically active ingredient was detected by means of a spectrometric measurement with a wavelength of 271 nm.

Figure 4:
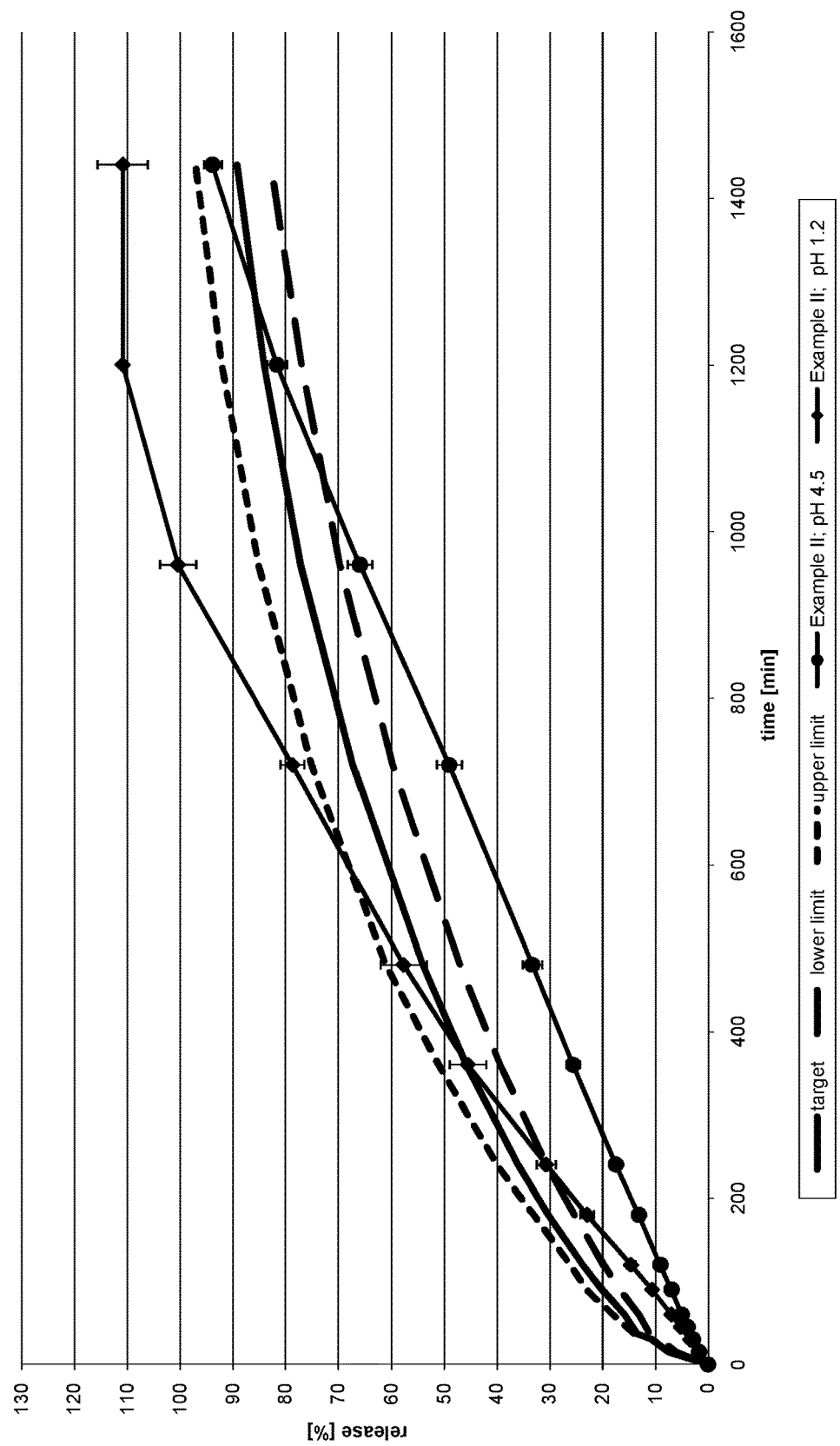
FIG. 4 shows the in vitro release profiles of a pharmaceutical dosage form according to the invention in an acidic medium (pH 1.2) and with phosphate buffer (pH 4.5), containing oxymorphone and 30 wt.-% sodium carbonate (Example II) in comparison to reference tablets.

According to the preceding table, the formulation was made with oxymorphone instead of tramadol. As illustrated in FIG. 4 the release profile shows a retarded and linear release of the pharmacologically active ingredient. In the acidic medium the release was accelerated in comparison to the release in the acetate buffered medium (pH 4.5).

EXAMPLE III

Tablets of the following composition were formed:

| Excipient | Per tablet [mg] | [wt.-%] |
|---|---|---|
| Oxymorphone HCL anhydrous | 80.0 | 11.1 |
| Polyethylene oxide 7,000,000 | 337.3 | 46.9 |
| Sodium Carbonate | 108.0 | 15.0 |
| Pentasodium phosphate | 108.0 | 15.0 |
| Macrogol 6000 | 81.7 | 11.3 |
| α-Tocopherol | 1.4 | 0.2 |
| Citric Acid anhydrous | 3.6 | 0.5 |
| Sum | 720.0 | |

According to Example II, the in vitro release profile of the pharmacologically active ingredient was measured in 900 ml acidic medium (pH 1.2) and in 900 mL acetate buffered medium (pH 4.5).

Figure 5:
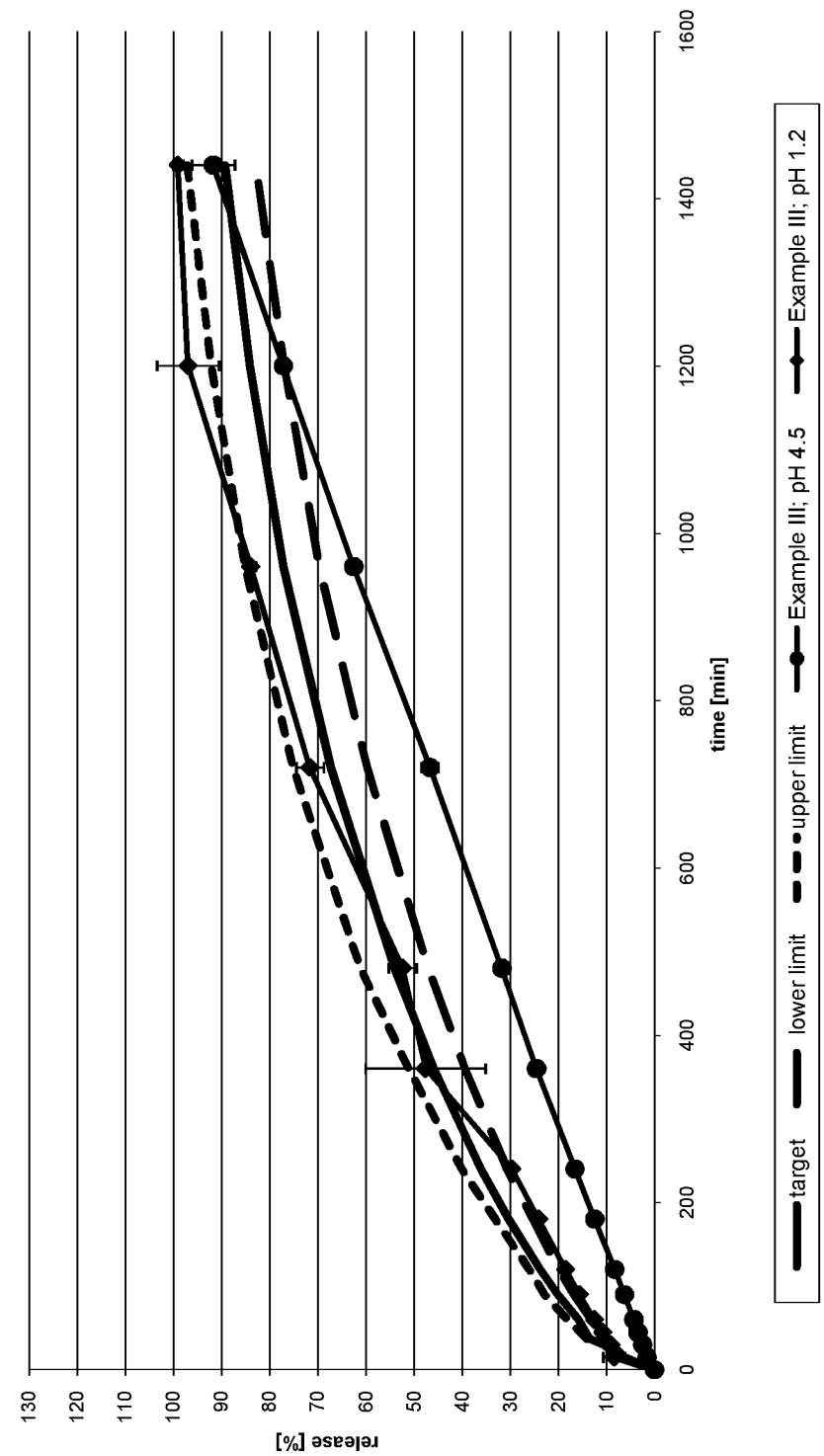
FIG. 5 shows the in vitro release profiles of a pharmaceutical dosage form according to the invention in an acidic medium (pH 1.2) and with phosphate buffer (pH 4.5), containing oxymorphone and 15 wt.-% each of sodium carbonate and pentasodium triphosphate (Example III) in comparison to reference tablets.

According to the preceding table the formulation was made with oxymorphone instead of tramadol. Moreover the formulation contains sodium carbonate and pentasodium triphosphate each 15 wt.-%. As illustrated in FIG. 5, the release profile shows a retarded and linear release of the pharmacologically active ingredient. In the acidic medium the release was accelerated in comparison to the release in the acetate buffered medium (pH 4.5).

The invention claimed is:

1. A pharmaceutical dosage form exhibiting a breaking strength of at least 500 N and comprising:
   a pharmacologically active ingredient (A);
   an inorganic salt (B), wherein the content of the inorganic salt (B) is from 29 to 70 wt.-%, based on the total weight of the dosage form;
   a polyalkylene oxide (C) having a weight average molecular weight of at least 200,000 g/mol, wherein the content of the polyalkylene oxide (C) is at least 30 wt.-%, based on the total weight of the dosage form;
   wherein the pharmacologically active ingredient (A) is embedded in a controlled release matrix comprising the inorganic salt (B) and the polyalkylene oxide (C), and wherein, under in vitro conditions, the release profile of the pharmacologically active ingredient (A) from said matrix comprises at least a time interval during which the release follows a zero order kinetics.

2. The pharmaceutical dosage form according to claim 1, wherein the time interval during which the release follows zero order kinetics is at least 20% of the total release time needed for a release of 95 wt.-% of the pharmacologically active ingredient (A) that was originally contained.

3. The pharmaceutical dosage form according to claim 1, wherein the release profile follows zero order kinetics within the range of from pH 1 to pH 7.

4. The pharmaceutical dosage form according to claim 1, which is prepared by hot-melt extrusion.

5. The pharmaceutical dosage form according to claim 1, which is a tablet.

6. The pharmaceutical dosage form according to claim 1, wherein the pharmacologically active ingredient (A) is an opioid selected from the group consisting of tapentadol, oxymorphone, hydromorphone, oxycodone, morphine and the physiologically acceptable salts thereof.

7. The pharmaceutical dosage form according to claim 1, wherein the inorganic salt (B) contains at least one component selected from the group consisting of alkali carbonates, earth alkali carbonates, alkali hydrogen carbonates, earth alkali hydrogen carbonates, alkali phosphates, earth alkali phosphates, alkali hydrogen phosphates, earth alkali hydrogen phosphates, alkali dihydrogen phosphates, earth alkali dihydrogen phosphates and pentaalkali tri(poly)phosphates.

8. The pharmaceutical dosage form according to claim 7, wherein the inorganic salt (B) is sodium carbonate or pentasodium triphosphate or a mixture thereof.

9. The pharmaceutical dosage form according to claim 1, wherein the polyalkylene oxide (C) has a molecular weight of at least 0.5 million g/mol.

10. The pharmaceutical dosage form according to claim 9, wherein the polyalkylene oxide (C) has a molecular weight of at least 1 million g/mol.

11. The pharmaceutical dosage form according to claim 10, wherein the polyalkylene oxide (C) has a molecular weight within the range of from 1 to 15 million g/mol.

12. The pharmaceutical dosage form according to claim 1, which comprises polyalkylene glycol.

13. The pharmaceutical dosage form according to claim 12, wherein the polyalkylene glycol has a molecular weight of at least 1000 g/mol.

14. A method of treating pain in a patient in need of such treatment, said method comprising administering to said patient a pharmaceutical dosage form according to claim 6.

15. The pharmaceutical dosage form according to claim 1, wherein the amount of the inorganic salt (B) in the pharmaceutical dosage form is within the range of from 29 to 41 wt.-%, based on the total weight of the pharmaceutical dosage form.

16. The pharmaceutical dosage form according to claim 1, which weighs between 250 mg to 1500 mg.

17. The pharmaceutical dosage form according to claim 16, which weighs at least 600 mg.

18. The pharmaceutical dosage form according to claim 16, wherein the time interval during which the release follows zero order kinetics is at least 60% of the total release time needed for a release of 95 wt.-% of the pharmacologically active ingredient (A) that was originally contained.

19. The pharmaceutical dosage form according to claim 18, wherein the time interval during which the release follows zero order kinetics is at least 70% of the total release time needed for a release of 95 wt.-% of the pharmacologically active ingredient (A) that was originally contained.

20. The pharmaceutical dosage form according to claim 19, wherein the time interval during which the release follows zero order kinetics is at least 80% of the total release time needed for a release of 95 wt.-% of the pharmacologically active ingredient (A) that was originally contained.

21. A pharmaceutical dosage form exhibiting a breaking strength of at least 500 N and comprising:
   a pharmacologically active ingredient (A) selected from the group consisting of tapentadol, oxymorphone, hydromorphone, oxycodone, morphine and the physiologically acceptable salts thereof;
   an inorganic salt (B), wherein the content of the inorganic salt (B) is from 29 to 70 wt.-%, based on the total weight of the dosage form;
   a polyalkylene oxide (C) having a weight average molecular weight of at least 200,000 g/mol, wherein the content of the polyalkylene oxide (C) is at least 30 wt.-%, based on the total weight of the dosage form;

wherein the pharmacologically active ingredient (A) is embedded in a controlled release matrix comprising the inorganic salt (B) and the polyalkylene oxide (C), wherein the pharmaceutical dosage form weighs between 250 mg and 1500 mg, and wherein, under in vitro conditions, the release profile of the pharmacologically active ingredient (A) from said matrix comprises at least a time interval during which the release follows a zero order kinetics, and the time interval during which the release follows zero order kinetics is at least 60% of the total release time needed for a release of 95 wt.-% of the pharmacologically active ingredient (A) that was originally contained in the pharmaceutical dosage form.

22. A pharmaceutical dosage form exhibiting a breaking strength of at least 500 N and comprising:

a pharmacologically active ingredient (A) selected from the group consisting of tapentadol, oxymorphone, hydromorphone, oxycodone, morphine and the physiologically acceptable salts thereof;

an inorganic salt (B), wherein the content of the inorganic salt (B) is from 29 to 70 wt.-%, based on the total weight of the dosage form;

a polyalkylene oxide (C) having a weight average molecular weight of at least 500,000 g/mol, wherein the content of the polyalkylene oxide (C) is at least 30 wt.-%, based on the total weight of the dosage form;

wherein the pharmacologically active ingredient (A) is embedded in a controlled release matrix comprising the inorganic salt (B) and the polyalkylene oxide (C), wherein the pharmaceutical dosage form weighs between 250 mg and 1500 mg, and wherein, under in vitro conditions, the release profile of the pharmacologically active ingredient (A) from said matrix comprises at least a time interval during which the release follows a zero order kinetics, and the time interval during which the release follows zero order kinetics is at least 60% of the total release time needed for a release of 95 wt.-% of the pharmacologically active ingredient (A) that was originally contained in the pharmaceutical dosage form.

* * * * *